United States Patent [19]

Suzuki et al.

[11] Patent Number: 5,053,408
[45] Date of Patent: Oct. 1, 1991

[54] HEXITOL DERIVATIVES HAVING VASODILATIVE ACTIVITY

[75] Inventors: Fumio Suzuki, Mishima; Hiroaki Hayashi, Shizuoka; Takeshi Kuroda, Shizuoka; Kazuhiro Kubo, Shizuoka; Junichi Ikeda, Mishima, all of Japan

[73] Assignee: Kyowa Hakko Kogyo Co., Ltd., Tokyo, Japan

[21] Appl. No.: 508,701

[22] Filed: Apr. 13, 1990

[30] Foreign Application Priority Data

Apr. 17, 1989 [JP] Japan .................. 1-97032
Nov. 10, 1989 [JP] Japan .................. 1-293125

[51] Int. Cl.$^5$ .................. A61K 31/495; C07D 487/00; C07D 239/02; C07D 401/00
[52] U.S. Cl. .................. 514/354; 514/218; 540/575; 544/263; 544/268; 544/295; 544/357; 544/362; 544/363; 544/364; 544/366; 544/368; 544/370; 544/373; 544/376
[58] Field of Search .................. 540/575; 514/218, 254; 544/263, 265, 268, 359, 362, 364, 366–373, 376–379, 295, 357, 363

[56] References Cited

PUBLICATIONS

Klessing et al., Chem. Abst. 96-218188w (1982).
Klessing et al., Chem. Abst. 97-110337a (1982).

Primary Examiner—Cecilia Shen
Attorney, Agent, or Firm—Fitzpatrick, Cella, Harper & Scinto

[57] ABSTRACT

Disclosed is a hexitol derivative represented by the formula (I):

wherein Q represents a formula selected from the group consisting of wherein
a represents NH, O or S;
each of b, c and d independently represents CH or N;
each of $R^1$, $R^2$, $R^3$ and $R^4$ independently represents hydrogen, lower alkyl, trifluoromethyl, aryl, lower alkanoyloxy, amino, lower alkylamino, lower alkanoylamino, lower alkanoyl, aroyl, halogen, nitro, $(CH_2)_mOR^7$, $(CH_2)_mSR^7$, $(CH_2)_mCO_2R^7$ where $R^7$ represents hydrogen or lower alkyl and m represents an integer of 0 to 3;
each of $R^5$ and $R^6$ independently represents hydrogen or lower alkyl;
U represents >N— or t,20
W represents a single bond, —O— or —S—;
X represents $$-(\overset{Y^1}{\underset{R^2}{C}})_l- \text{ or } -CY^3=CY^4-(\overset{Y^1}{\underset{Y^2}{C}})_l-$$

wherein
each of $Y^1$ and $Y^2$ independently represents hydrogen, lower alkyl, hydroxyl, lower alkanoyloxy, nitrile or phenyl; or $Y^1$ and $Y^2$ are combined together to form oxygen;
each of $Y^3$ and $Y^4$ independently represents hydrogen or lower alkyl; and l is an integer of 0 to 6, and where l is an integer of 2 to 6, each $$-\overset{Y^1}{\underset{Y^2}{C}}-$$

may be the same or different;
Z represents hydrogen or nitro; and, n is 2 or 3 or a pharmaceutically acceptable salt thereof. The compounds show prominent coronary vasodilative activities, and are useful in treating angina pectoris and myocardial infarction.

26 Claims, No Drawings

HEXITOL DERIVATIVES HAVING VASODILATIVE ACTIVITY

BACKGROUND OF THE INVENTION

The present invention relates to novel deoxy-1.4;3.6-dianhydrohexitols and nitric acid esters thereof having a vasodilative activity.

Organic nitrates, for example, nitroglycerine, have been clinically used for angina pectoris in sublingual administration, and it has not orally been administered. Hence, nitroglycerine was useless for preventive therapy for attacks of angina pectoris and the administration of nitroglycerine was limited to emergency care on attacks of angina pectoris.

On the other hand, it has been known that hexitol derivatives, e.g., isosorbide dinitrate are useful in preventing or relieving accute anginal attacks [The Merck Index. 10th edition, page 751 (1983)]. Nevertheless, therapeutic effects of isosorbide dinitrate for angina pectoris or coronary deficiency were not enough in view of the pharmacological activities and side effects such as headache, vomiting, etc. On industrial viewpoint, both organic nitrate and isosorbide dinitrate should be prepared and handled under strict regulation for prevention of disasters.

As an improved hexitol derivative, 5-(4-methylpiperazino)-5-deoxy-1.4;3.6-dianhydro-L-iditol 2-nitrate having a vasodilative activity was developed and disclosed in Japanese Published Unexamined Patent Application No. 58686/82 [U.S. Pat. No. 4,363,805 and EP-A No. 44940].

However, novel hexitol derivatives are desired for improvement in pharmacological activities and water solubility, as a medicine for angina pectoris.

SUMMARY OF THE INVENTION

An object of the present invention is to provide novel hexitol derivatives, based on the finding that substituted piperazino- or substituted homopiperazino-1.4;3.6-dianhydrohexitol and nitric acid esters thereof show prominent coronary vasodilative activities, and are useful for oral administration. The compounds are useful in treating angina pectoris and myocardial infarction.

In accordance with the present invention, there are provided an hexitol derivative represented by the formula (I);

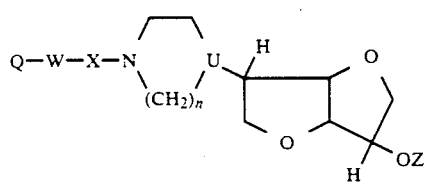
(I)

wherein: Q represents a formula selected from the group consisting of:

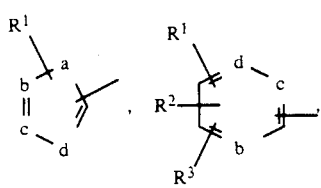

-continued

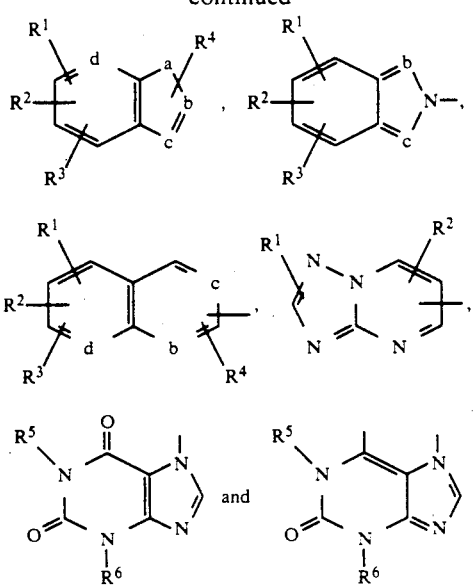

wherein
a represents NH, O or S;
each of b, c and d independently represents CH or N;
each of $R^1$, $R^2$, $R^3$ and $R^4$ independently represents hydrogen, lower alkyl, trifluoromethyl, aryl, lower alkanoyloxy, amino, lower alkylamino, lower alkanoylamino, lower alkanoyl, aroyl, halogen, nitro, $(CH_2)_mOR^7$, $(CH_2)_mSR^7$, $(CH_2)_mCO_2R^7$ where $R^7$ represents hydrogen or lower alkyl, and m represents an integer of 0 to 3;
each of $R^5$ and $R^6$ independently represents hydrogen or lower alkyl;
U represents >N— or

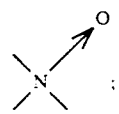

;

W represents a single bond, —O— or —S—;
X represents

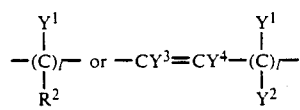

where
each of $Y^1$ and $Y^2$ independently represents hydrogen, lower alkyl, hydroxyl, lower alkanoyloxy, nitrile or phenyl; or $Y^1$ and $Y^2$ are combined together to form oxygen; each of $Y^3$ and $Y^4$ independently represents hydrogen or lower alkyl; and l is an integer of 0 to 6, and where l is an integer of 2 to 6, each

may be the same or different;
Z represents hydrogen or nitro; and n is 2 or 3 [hereafter the compounds represented by formula (I) are referred to as Compound (I)] or pharmaceutically acceptable salts thereof.

Compound (I) contains several asymmetrical carbons. Thus, optical isomers of compound (I) [Compound (Ia), (Ib), (Ic) and (Id)] are exemplified as follows.

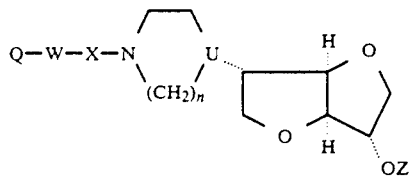
(Ia)

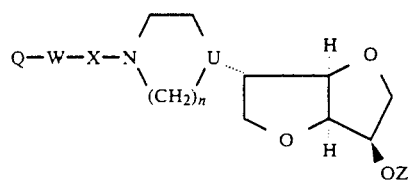
(Ib)

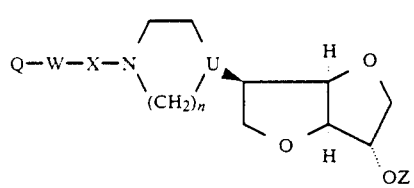
(Ic)

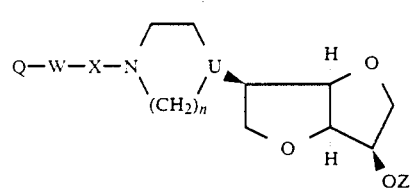
(Id)

wherein Q, U, W, X, Z and n have the same significances as described above.

The present invention includes all possible steric isomers including these optical isomers and mixtures thereof.

DETAILED DESCRIPTION OF THE INVENTION

In the definition of respective groups in formula (I), the lower alkyl and the alkyl moiety in the lower alkylamino mean a straight or branched alkyl having 1 to 6 carbon atoms, for example, methyl, ethyl, n-propyl, isopropyl, n-butyl, isobutyl, sec-butyl, tert-butyl, n-pentyl, neopentyl, n-hexyl, etc. The lower alkanoyl and the alkanoyl moiety in the lower alkanoyloxy and lower alkanoylamino mean a straight or branched alkanoyl having 1 to 6 carbon atoms, for example, formyl, acetyl, propionyl, butyryl, isobutyryl, valeryl, isovaleryl, pivaloyl, hexanoyl, etc. The aryl and the aryl moiety in the aroyl means phenyl, naphthyl, etc. The halogen includes for example, fluorine, chlorine, bromine and iodine.

The salts of Compound (I) mean pharmaceutically acceptable salts such as acid addition salts, metal salts, ammonium salts, organic amine addition salts, amino acid addition salts, etc.

The pharmaceutically acceptable acid addition salt of Compound (I) includes an inorganic acid salt such as hydrochloride, sulfate, phosphate, etc. and an organic acid salt such as acetate, maleate, fumarate, tartarate, citrate, etc. The pharmaceutically acceptable metal salt includes an alkali metal salt such as sodium salt, potassium salt, etc.; an alkaline earth metal salt such as magnesium salt, calcium salt, etc. and other metal salt such as aluminium salt and a zinc salt, etc. The pharmaceutically acceptable organic amine addition salt includes an addition salt of morpholine, piperidine, etc. The pharmaceutically acceptable amino acid addition salt includes an addition salt of lysine, glycine, phenylalanine and the like.

Processes for preparing Compounds (I) are set forth below.

When the defined groups are changed under the conditions of the following processes or are inadequate to proceeding of the following processes, processes can be readily carried out by a usual method in the organic synthetic chemistry, for example, by protection of functional groups, elimination of protecting groups.

Process 1

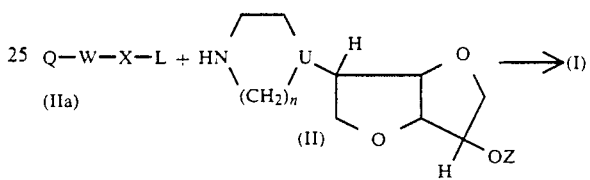

wherein Q, U, W, X, Z and n have the same significances as described above; and L represents a leaving group.

Compound (I) is obtained by reacting Compound (IIa) with Compound (III).

The leaving group denoted by L includes, for example, halogen such as chlorine, bromine, iodine, etc.; alkylsulfonyloxy such as methanesulfonyloxy, etc.; arylsulfonyloxy such as phenylsulfonyloxy, p-toluenesulfonyloxy, etc..

The reaction is performed in a solvent, preferably in the presence of a base. Any solvent is used so long as it is inert to the reaction. The solvent includes, for example, ethers such as tetrahydrofuran, dioxane, etc.; amides such as dimethylformamide, dimethylacetamide, etc.; ketones such as acetone, methyl ethyl ketone, etc.; alcohols such as methanol, ethanol, isopropyl alcohol, etc.; halogenated hydrocarbons such as methylene chloride, chloroform, dichloroethane, etc.; esters such as ethyl acetate, etc.; and dimethylsulfoxide, etc. These solvents are used alone or in combination. The base used includes, for example, alkali metal bicarbonate such as sodium bicarbonate, potassium bicarbonate, etc.; alkali metal carbonate such as sodium carbonate, potassium carbonate, etc.; alkali metal hydride such as sodium hydride, etc.; alkali metal alkoxide such as sodium methoxide, sodium ethoxide, etc.; ammonium salt such as trimethyl benzyl ammonium hydroxide (Triton B), etc.; organic base such as triethylamine, pyridine, etc. The reaction temperature is in the range of 0° to 180° C., preferably from room temperature to 150° C. The reaction time varies depending upon the reaction temperature and is usually from 30 minutes to 20 hours.

Compound (I-1) and Compound (IIb) are represented by the following formula (I-1) and formula (IIb), respectively.

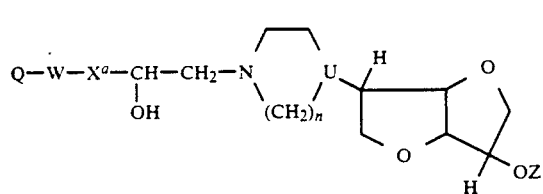 (I-1)

wherein Q, U, W, Z and n have the same significances as described above, and Xa represents same significance as X except for

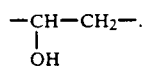

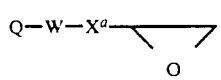 (IIb)

wherein Q, W and $X^a$ have the same significances as described above. Compound (I-1) is obtained by reacting Compounds (IIb) in place of Compound (IIa) with Compound (III) in the same manner as described above.

The starting Compounds (IIa), (IIb) and (III) are synthesized basically according to the methods described in Reference Examples. Compound (IIa) is obtained from notorious compounds or synthesized by notorious methods in J. Med. Chem., 30, 682 (1987); ibid., 30, 2216 (1987), etc. Compound (IIb) is synthesized from notorious compounds or by notorious methods in J. Med. Chem., 20, 371 (1977), etc.

Process 2

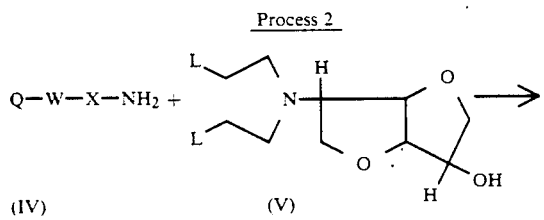

(IV)      (V)

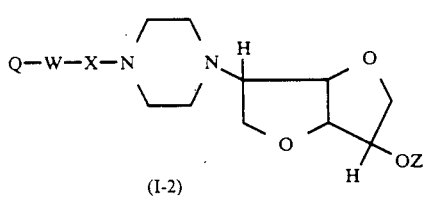

(I-2)

wherein Q, W, X, Z and L have the same significances as described above.

Compound (I-2) which is Compound (I) having a substituted piperazino group (U=>N—; n=2) is also obtained by reacting Compound (IV) with Compound (V).

The reaction proceeds basically under the same reaction conditions described in Process 1.

The starting Compounds (IV) and (V) are synthesized basically according to the procedures of Reference Examples.

Process 3

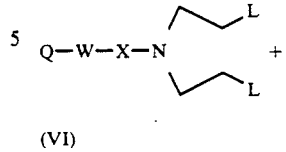

(VI)

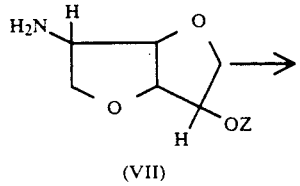

(VII)

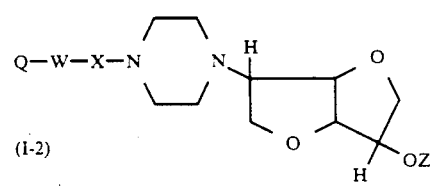

(I-2)

wherein Q, W, X, Z and L have the same significances as described above.

Compound (I-2) is obtained by reacting Compound (VI) with Compound (VII).

The reaction proceeds basically according to the reaction conditions in Process 1.

The starting Compounds (VI) and (VII) are synthesized basically according to the procedures of Reference Examples.

Process 4

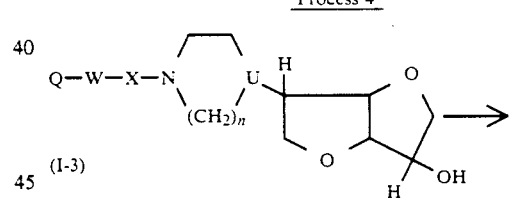

(I-3)

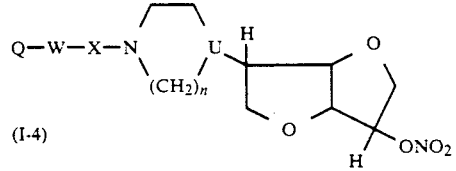

(I-4)

wherein Q, U, W, X and n have the same significances as described above.

Compound (I-3) and Compound (I-4) are compound (I) having hydroxyl (Z=H) or having nitric acid ester (Z=NO₂), respectively. Compound (I-4) is prepared from Compound (I-3).

The reaction is performed at −40° to 20° C. using a nitrating agent such as acetic anhydride-fuming nitric acid, fuming nitric acid, fuming nitric acid-conc. sulfuric acid, etc. in the presence or absence of a solvent. As the solvent, acetonitrile, chloroform, methylene chloride, acetic acid, etc. are preferably used.

Process 5

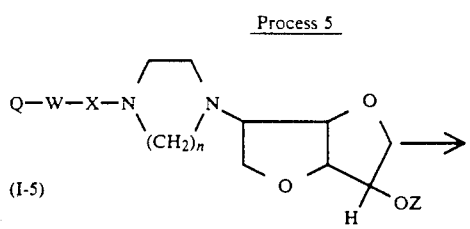
(I-5)

↓

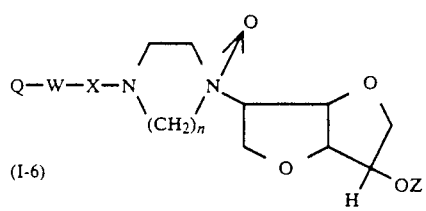
(I-6)

wherein Q, W, X, Z and n have the same significances as described above.

Compound (I-6) having an N-oxide which is Compound (I) where us is

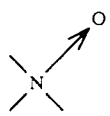

is obtained by oxidizing Compound (I-5) according to the method as described hereinbefore.

The oxidizing agent used includes, for example, m-chloroperbenzoic acid, peracetic acid, hydrogen peroxide and benzoyl peroxide. Azobisisobutyronitrile and the like are added as a catalyst, if necessary. As the solvent, methylene chloride, chloroform, acetic acid, methanol, diethylether and water are preferably used. The reaction temperature is in the range of −40° to −50° C. and the reaction is completed in 5 minutes to 6 hours.

The intermediates and the objective compounds in these processes are isolated and purified by usual purification methods in organic synthetic chemistry, for example, filtration, extraction, drying, concentration, recrystallization, various column chromatographies, etc. The intermediates are provided in the subsequent reaction, with or without being particularly purified.

In case that salts of Compound (I) are desired to be obtained, when Compound (I) is obtained in the form of a salt, Compound (I) may be purified as it is. Further in case that Compound (I) is obtained in a free form, salts may be formed in a conventional manner.

Compound (I) and pharmaceutically acceptable salts thereof may be present in the form of addition products to water or various solvents; in this case, the addition products are also included in the present invention.

Specific examples of Compound (I) obtained by the respective processes are shown in Tables 1-1 to 1-3.

TABLE 1-1

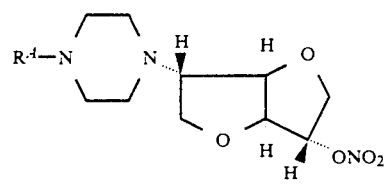

| Compound No. (Example) | $R^4$ |
|---|---|
| 1(1) |  |
| 2(2) | 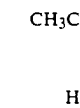 |
| 3(3) | 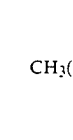 |
| 4(4) | 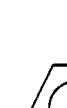 |
| 5(5) | 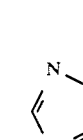 |
| 6(6) |  |
| 7(7) |  |
| 8(8) |  |

TABLE 1-1-continued
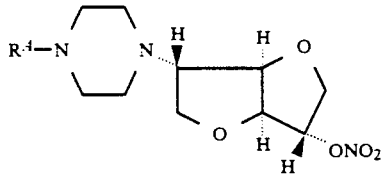
| Compound No. (Example) | R^A |
|---|---|
| 9(9) | 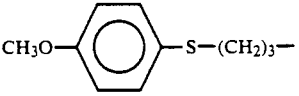 |
| 10(10) | 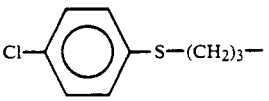 |
| 11(11) | 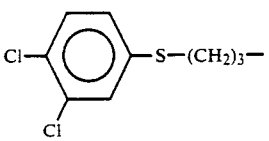 |
| 12(12) | 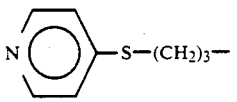 |
| 13(13) | 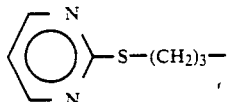 |
| 14(14) | 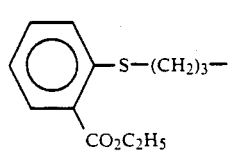 |
| 15(15) | 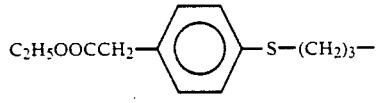 |
| 16(16) | 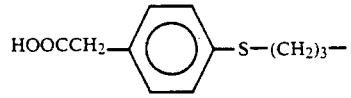 |
| 17(17) | 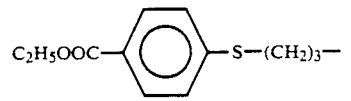 |
| 18(18) | 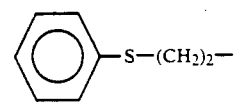 |
| 19(19) | 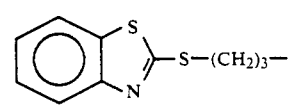 |
TABLE 1-1-continued
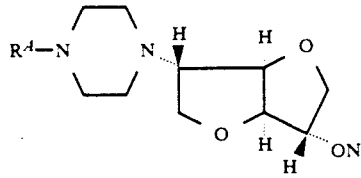
| Compound No. (Example) | R^A |
|---|---|
| 20(20) | 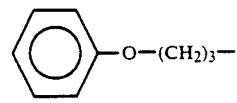 |
| 21(21) | 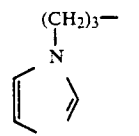 |
| 22(22) | 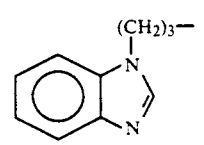 |
| 23(23) | 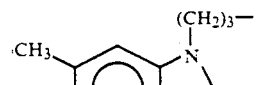 |
| 24(24) | 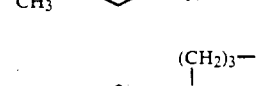 |
| 25(24) | 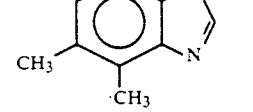 |
| 26(25) | 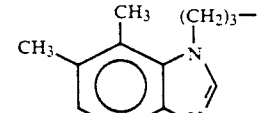 |
| 27(26) | 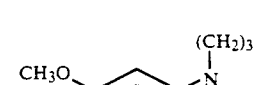 |
| 28(27) | 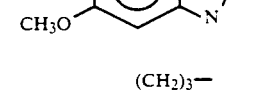 |

TABLE 1-1-continued
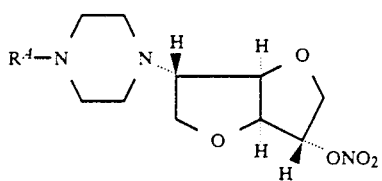
| Compound No. (Example) | R⁴ |
|---|---|
| 29(28) | 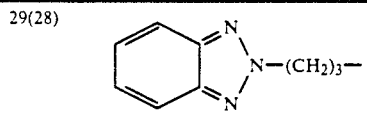 |
| 30(29) | 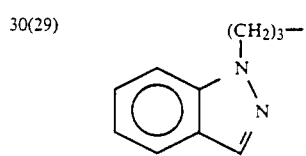 |
| 31(30) | 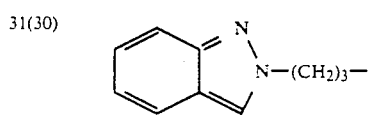 |
| 32(31) | 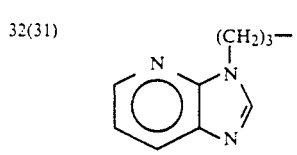 |
| 33(32) | 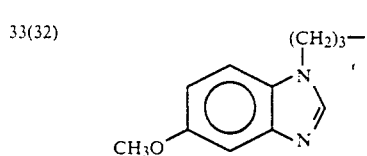 |
| 34(32) | 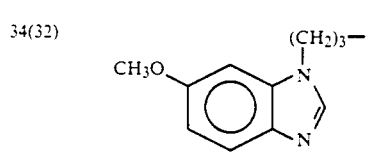 |
| 35(33) | 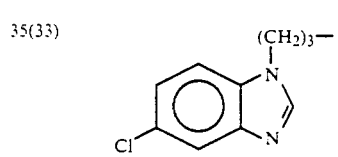 |
| 36(33) | 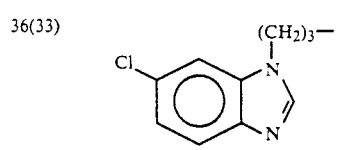 |
| 37(34) | 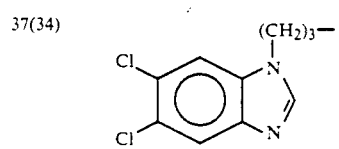 |
| 38(35) | 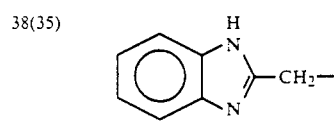 |
TABLE 1-1-continued
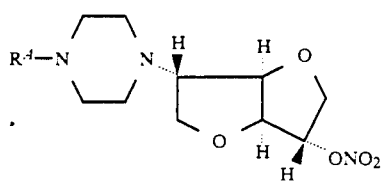
| Compound No. (Example) | R⁴ |
|---|---|
| 39(36) | 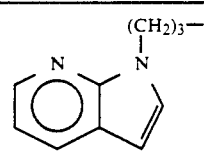 |
| 40(37) | 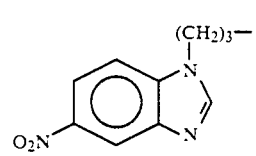 |
| 41(37) | 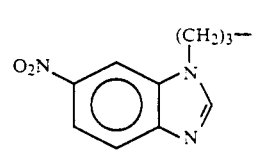 |
| 42(38) | 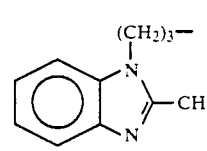 |
| 43(39) | 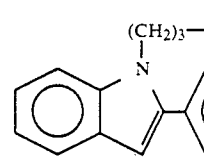 |
| 44(40) | 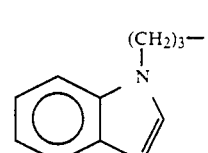 |
| 45(41) | 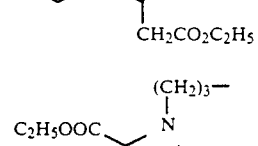 |
| 46(42) | 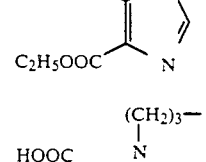 |
| 47(43) | 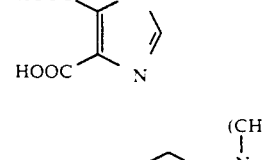 |

TABLE 1-1-continued

[Structure: R^A—N(piperazine)—N—[bicyclic sugar with ONO2 group], stereochemistry shown with H]

| Compound No. (Example) | R^A |
|---|---|
| 48(43) | 1-(CH2)3- benzimidazole with C2H5OOC substituent |
| 49(44) | 1-(CH2)3- benzimidazole with HOOC substituent |
| 50(44) | 1-(CH2)3- benzimidazole with HOOC substituent |
| 51(45) | 2,3,4-trimethoxyphenyl-O-(CH2)3- (CH3O, CH3O, CH3O) |
| 52(46) | 3,5-dimethoxyphenyl-O-(CH2)3- |
| 53(47) | 3,5-dimethylphenyl-O-(CH2)3- |
| 54(48) | 3,4,5-trimethoxyphenyl-CH=CHCO- |
| 55(50) | 2-methyl-4-nitro (with O2N and NO2 substituents) phenyl |
| 56(50) | 2,6-dinitrophenyl (NO2, NO2) |
| 57(51) | 2-(CH2)2- benzimidazole (NH) |
| 58(52) | 2-benzothiazolyl |
| 59(53) | 2-benzoxazolyl |
| 60(54) | 1-phenyl-tetrazol-5-yl |
| 61(55) | 3,5-dimethoxyphenyl-(CH2)2- |
| 62(56) | 1-benzimidazolyl-(CH2)2- |
| 63(57) | 2,3,4-trimethoxyphenyl-O-(CH2)2- |
| 64(58) | 2-methoxyphenyl |

TABLE 1-1-continued $R^4-N\underset{\diagdown}{\diagup}N-\text{[isosorbide-ONO}_2\text{ structure]}$

| Compound No. (Example) | $R^4$ |
|---|---|
| 65(59) | 3,4,5-trimethoxyphenyl-C(CN)(CH(CH$_3$)$_2$)-(CH$_2$)$_3$- |
| 66(60) | 5,7-dimethyl-1,2,4-triazolo ring |
| 67(61) | 4,7-dimethyl-4-hydroxybenzimidazol-1-yl-(CH$_2$)$_3$- |
| 68(61) | 4,6-dimethyl-7-hydroxybenzimidazol-1-yl-(CH$_2$)$_3$- |
| 69(62) | quinolin-2-yl |
| 70(63) | C$_6$H$_5$-O-(CH$_2$)$_2$- |
| 71(64) | pyrimidin-2-yl |
| 72(65) | C$_6$H$_5$-S-(CH$_2$)$_4$- |
| 73(81) | 2,3,4-trimethoxy-6-methylphenyl-CH$_2$- |
| 74(82) | 5-chlorobenzothiazol-2-yl |
| 75(83) | thiazolo[5,4-b]pyridin-2-yl |
| 76(84) | 1H-benzimidazol-2-yl |
| 77(85) | 4-chloro-5-methyl-3-phenyl-thiazol-2-yl (approx) |
| 78(86) | 4-amino-6,7-dimethoxyquinazolin-2-yl |
| 79(87) | 4-amino-6,7,8-trimethoxyquinazolin-2-yl |
| 80(88, 109) | pyridin-3-yl-CO- |
| 81(89) | pyridin-2-yl-CO- |
| 82(90) | pyridin-4-yl-CO- |

TABLE 1-1-continued

[Structure: R⁴-N(piperazine)-N-H attached to bicyclic furan-furan system with ONO₂ group]

| Compound No. (Example) | R⁴ |
|---|---|
| 83(91) | 2-furyl-CO— |
| 84(92) | phenyl-CO— |
| 85(93) | 2-chloro-pyridin-3-yl-CO— |
| 86(94) | pyrazin-2-yl-CO— |
| 87(95) | 2,3,4-trimethoxyphenyl-CO— (H₃CO, OCH₃, OCH₃) |
| 88(96) | 3,4,5-trimethoxyphenyl-CO— (H₃CO, H₃CO, OCH₃) |
| 89(97) | 6-chloro-pyridin-3-yl-CO— |
| 90(98) | 5-bromo-pyridin-3-yl-CO— |
| 91(99) | 2-methyl-pyridin-3-yl-CO— |
| 92(100) | quinolin-3-yl-CO— |
| 93(101) | 6-methyl-pyridin-3-yl-CO— |
| 94(102) | thiophen-3-yl-CO— |
| 111(103) | thiophen-2-yl-CO— |
| 112(104) | furan-3-yl-CO— |
| 114(106) | 6-hydroxy-pyridin-3-yl-CO— |
| 115(107) | 2-hydroxy-pyridin-3-yl-CO— |
| 116(108) | 2-methyl-thiazol-4-yl-CO— |
| 120(113) | 1,2,3-thiadiazol-4-yl-CO— |
| 121(114) | 1,2,3-thiadiazol-5-yl-CO— |
| 122(115) | 2-amino-thiazol-4-yl-CO— |

TABLE 1-2

| Compound No. (Example) | Structure |
|---|---|
| 95(66) | Phenyl–S–(CH₂)₃–N(piperazine)–N–[isosorbide-ONO₂] |
| 96(67) | Phenyl–S–(CH₂)₃–N(piperazine)–N–[isosorbide-ONO₂] |
| 97(68) | $R^B$–N(piperazine)–N–[isosorbide-ONO₂]; $R^B$ = Phenyl–S–(CH₂)₃– |
| 98(69) | $R^B$–N(piperazine)–N–[isosorbide-ONO₂]; $R^B$ = benzimidazol-1-yl–(CH₂)₃– |
| 99(70) | Phenyl–S–(CH₂)₃–N(homopiperazine)–N–[isosorbide-ONO₂] |
| 113(105) | 3-pyridyl–CO–N(piperazine N-oxide)–N–[isosorbide-ONO₂] |

TABLE 1-2-continued

| Compound No. (Example) | Structure |
|---|---|
| 118(111) | Piperazine-isosorbide-ONO2 with $R^B$ = nicotinoyl (pyridine-3-CO—) |
| 119(112) | Nicotinoyl-piperazine-N-isosorbide-ONO2 |

TABLE 1-3

Structure: $R^C$—N(piperazine)—N—[isosorbide with OH]

| Compound No. (Example) | $R^C$ |
|---|---|
| 100(49) | 2-nitrophenyl (o-NO2-C6H4—) |
| 101(71) | C6H5—S—(CH2)3— |
| 102(72) | C6H5—O—(CH2)3— |
| 103(73) | 2-benzoxazolyl |
| 104(74) | 1-phenyl-tetrazol-5-yl |

TABLE 1-3-continued

| Compound No. (Example) | $R^C$ |
|---|---|
| 105(75) | 3,4,5-tri(CH3O)-C6H2—O—(CH2)3— |
| 106(76) | 3,5-di(CH3O)-C6H3—O—(CH2)3— |
| 107(77) | 3,4,5-tri(CH3O)-C6H2—C(CN)(CH(CH3)2)—(CH2)3— |
| 108(78) | C6H5—O—(CH2)2— |

TABLE 1-3-continued

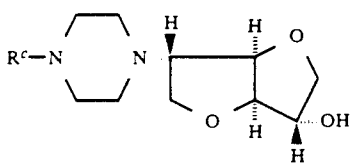

| Compound No.<br>(Example) | R^c |
|---|---|
| 109(79) | 3,5-dimethylphenyl-O-(CH$_2$)$_3$— |
| 110(80) | 2-methoxyphenyl |
| 117(110) | pyridine-3-CO— |

The pharmacological effects of compound (I) are illustrated in (a) a test for coronary vasospasm model, (b) a test for heart failure model and (c) acute toxicity test.

(a) Effects on coronary vasospasm model
(lysine-vasopressin test)

Male Wistar rats weighing 210–250 g were used as experimental animals. Electrocardiogram (ECG) was measured by electrocardiograph (RB-5, Nihon Koden, Tokyo, Japan) and recorded on polygraph.

Oral and intraperitoneal administration of test compounds to rats were performed 30 and 20 minutes before the anesthetization, respectively. After rats were anesthetized with urethane, lysine-vasopressin (manufactured by Sigma Co., Ltd.; V-2875, 0.3 I.U./kg) was intravenously injected to rats for the purpose of inducing coronary vasospasm. After the lysine-vasopressin injection, increase of ST-segment was observed in ECG [Arzneim. Forsh., 36, 1454(1986)].

In this test, the inhibitory effect of ST-segment elevation following lysine-vasopressin injection was regarded as anti-angina pectoris activity [Arzneim. Forsh., 36, 1454 (1986)]. The ST-segment heights were measured before and at 20 to 30 seconds after lysine-vasopressin injection in rats with an without test compound treatment, and then elevation % of ST-segment was calculated in each rat. Inhibition % was calculated from the following equation.

Depression rate (%) =

$$\left(1 - \frac{\text{ST-segment elevation rate of test compounds-treated group}}{\text{ST-segment elevation rate of test compounds-untreated group}}\right) \times 100$$

In this test, the compounds which have the depression rate of 20% or higher were defined as effective in the coronary vasospasm model, and the compounds are considered to have anti-vasospasm activity. The minimum dose for showing the anti-vasospasm activity was defined as the minimum effective dose (MED).

The results are shown in Table 2.

(b) Propranolol-induced heart failure model

Adult mongrel dogs of either sex, weighing from 8 to 22 kg were used for the experiments. The animals were anesthetized with sodium pentobarbital (35 mg/kg iv) and the lungs were ventilated with respirator (made by Takashima Co., for big animals) following tracheal intubation. The common carotid artery was cannulated and the catheter for measurement of left ventricular pressure (Millar Tip ®) was advanced to the left ventricular cavity. Left ventricular pressure (LVP), the maximum rate of change of left ventricular pressure (Max dp/dt), and left ventricular end-diastolic pressure (LVEDP) were measured by the Millar Tip transducer. The systemic blood pressure (BP) was measured with a pressure transducer (MPU-0.5, Nihonkoden) attached to a catheter placed in the femoral artery, and heart rate (HR) was measured with a heart rate meter (AT610-G, Nihonkoden) from B.P. All measurements were recorded on a polygraph (RPM-6200 Nihonkoden) or on a pen-recorder (RAT-1200, Nihonkoden).

After values of all parameters were stabilized, abolus intravenous injection of propranolol at a dose of 2 mg/kg was performed. Thereafter, an intravenous infusion of propranolol (0.05 mg/kg/min.) was carried out to evoke heart failure [J. Cardiovasc. Pharmacol. 6, 35–42 (1984)]. LVEDP was increased by 10 to 15 mmHg as a symptom of heart failure. After occurrance of heart failure, the test compounds were intravenously or intraduodenally administered. After administration of the test compounds, LVEDP, LVP, Max dp/dt, BP and HR were recorded on interval of every 15 minutes.

In this experiment, LVEDP elevation was used as an index of heart failure and the compounds which decrease LVEDP by over 20% were defined as effective.

The results are shown in Table 2. Compounds 1, 22, 58, 80 and 80' were effective at 0.3 mg/kg of intraduodenal administration, and compounds 31, 80 and 80' were effective at a dose of 0.3 mg/kg (iv.).

TABLE 2

| Compound No. | Coronary vasoconstriction model MED (mg/kg) | | Heart failure model Effective dose (mg/kg) | |
|---|---|---|---|---|
| | i.p. | p.o. | i.d. | i.v. |
| 1 | <25 | <30 | 0.3 | |
| 12 | | <30 | | |
| 16 | | <30 | | |
| 21 | | <30 | | |
| 22 | <25 | <30 | 0.3 | |
| 23 | | <30 | | |
| 24/25*1 | | <30 | | |
| 27 | | <30 | | |
| 31 | <25 | | | 0.3 |
| 57 | <25 | | | |
| 58 | <25 | | 0.3 | |
| 60 | <25 | | | |
| 76 | | <30 | | |
| 78 | | <30 | | |
| 80*4 | <25 | <30 | 0.3 | 0.3 |
| 80'*4 | <25 | <30 | 0.3 | 0.3 |
| 81 | | <30 | | |
| 83 | | <30 | | |
| 84 | <25 | | | |

TABLE 2-continued

| Compound No. | Coronary vasoconstriction model MED (mg/kg) | | Heart failure model Effective dose (mg/kg) | |
|---|---|---|---|---|
| | i.p. | p.o. | i.d. | i.v. |
| 87 | | <30 | | |
| 89 | | <30 | | |
| 93 | | <30 | | |
| 96 | <25 | | | |
| 102 | <25 | <30 | | |
| 111 | | <30 | | |
| 112 | | <30 | | |
| 113 | <25 | | | |
| 114 | | <30 | | |
| 117 | <25 | <30 | | |
| (Reference Compounds) | | | | |
| ISDN*2 | <30 | <30 | | |
| Nicorandil*3 | | <30 | | |

*1Mixture (21:1)
*2Isosorbide dinitrate
*3The Merck Index, 10th edition, 6358 (1983)
*4Compound 80 is a free form, and Compound 80′ is hydrochloride salt of Compound 80.

(c) Acute toxicity

The compounds were orally administered and intraperitoneally administered to male dd-mice weighing 20 to 25 g. Minimum effective dose (MED) was determined by observing the mortality for seven days after the administration.

The results are shown in Table 3.

TABLE 3

| | MLD (mg/kg) | |
|---|---|---|
| Compound No. | i.p. | p.o. |
| 1 | >100 | >150 |
| 12 | >100 | >300 |
| 16 | >100 | >300 |
| 21 | >100 | >300 |
| 22 | >100 | >300 |
| 23 | >100 | >300 |
| 24/25 | >100 | >300 |
| 27 | >100 | >300 |
| 31 | >100 | >300 |
| 57 | >100 | >300 |
| 58 | >100 | >300 |
| 60 | >100 | >300 |
| 76 | >100 | >300 |
| 78 | >100 | >300 |
| 80 | >100 | >300 |
| 80′ | >100 | >300 |
| 81 | >100 | >300 |
| 83 | >100 | >300 |
| 84 | >100 | >300 |
| 87 | >100 | >300 |
| 89 | >100 | >300 |
| 93 | >100 | >300 |
| 96 | >100 | >300 |
| 102 | >100 | >300 |
| 111 | >100 | >300 |
| 112 | >100 | >300 |
| 113 | >100 | >300 |
| 114 | >100 | >300 |

Compound (I) or pharmacologically acceptable salts thereof may be used as they are or in the form of various dosage forms depending upon their pharmacological activity and purpose of administration. The medical preparation of the present invention is prepared by uniformly mixing, as an active ingredient, an effective dose of Compound (I) or pharmaceutically acceptable salts thereof with pharmaceutically acceptable carriers. The suitable carrier is selected from a broad range of carriers depending upon preparation modes desired for administration. These medical compositions are desirably in the form of unit dose suited to oral or parenteral administration.

In preparing compositions which are in the form suitable for oral administration, any useful pharmaceutically acceptable carriers are used. A liquid preparation suited to oral administration, for example, an emulsion and a syrup are prepared using water; sugars such as sucrose, sorbitol, fructose, etc.; glycols such as polyethylene glycol, propylene glycol, etc.; oils such as sesame oil, olive oil, soybean oil, etc.; antiseptics such as an alkyl p-hydroxybenzoate, etc.; flavors such as strawberry flavor, pepper mint, etc. Furthermore, a powder, a pill, a capsule and a tablet are prepared by using an excipient such as lactose, glucose, sucrose, mannitol, etc.; a disintegrator such as starch, sodium alginate, etc.; a lubricant such as magnesium stearate, talc, etc.; a binder such as polyvinyl alcohol, hydroxypropyl cellulose, gelatin, etc.; a surfactant such as a fatty acid ester, etc.; a plasticizer such as glycerine, etc. A tablet and a capsule are the most useful unit preparations for oral administration since their administration is easy. Upon preparing the tablet and capsule, individual pharmaceutical carriers are used. A solution for injection can be prepared by using distilled water, a saline, a glucose solution or carrier composed of a saline and a glucose solution. Effective dose and number of administration of Compound (I) or pharmaceutically acceptable salts thereof vary depending on mode of administration and, age, body weight, conditions, etc. of the patient. Daily dose is generally 1 to 50 mg/kg and the number of administration per day is 3 to 4 times.

Hereafter, the present invention is described by referring to Examples and Reference Examples below.

EXAMPLE 1

5-Deoxy-5-[4-(3-phenylthiopropyl)piperazin-1-yl]-1.4;3.6-dianhydro-L-iditol 2-nitrate hydrochloride (Compound 1)

A mixture of 1.25 g (4.82 mmols) of Compound b obtained in Reference Example 2, 0.91 g (4.87 mmols) of 1-chloro-3-phenylthiopropane (Reference Example 6), 0.7 ml (5.02 mmols) of triethylamine and 30 ml of ethanol was heated under reflux for 24 hours. The mixture was concentrated under reduced pressure, and the residue was purified by silica gel column chromatography (eluent: chloroform/methanol=40/1). The product was dissolved in ethanol, and to this solution was added ethyl acetate saturated with hydrogen chloride. The crystals were taken out by filtration and dried to afford 0.80 g (yield: 34%) of Compound 1.

Elemental analysis: as $C_{19}H_{27}N_3O_5S \cdot 2HCl$.
Calcd. (%); C, 47.30 H, 6.06 N, 8.71.
Found (%); C, 47.00 H, 5.98 N, 8.53.
IR (KBr) cm$^{311}$: 2985, 2410(br), 1643, 1275
NMR (DMSO-d$_6$) δ (ppm): 7.28-7.45(4H, m), 7.17-7.27 (1H, m), 5.42(1H, m), 5.04(1H, m), 4.80(1H, m), 4.09-4.19(1H, m), 4.06(2H, m), 3.87-3.98(1H, m), 3.0-4.8(11H, m), 3.06(2H, t, J=7.2 Hz), 2.02(2H, m)

EXAMPLE 2

5-[4-[3-(4-Acetyl-3-hydroxy-2-n-propylphenoxy)-propyl]-piperazin-1-yl]-5-deoxy-1.4;3.6-dianhydro-L-iditol 2-nitrate hydrochloride (Compound 2)

Compound 2 was obtained (yield; 43%) in a manner similar to Example 1 except that 2-hydroxy-4-(3-iodopropoxy)-3-n-propylacetophenone was used in place of 1-chloro-3-phenylthiopropane.

Elemental analysis: as $C_{24}H_{35}N_3O_8 \cdot HCl$.
Calcd. (%); C, 50.89 H, 6.58 N, 7.42.
Found (%); C, 50.56 H, 6.61 N, 7.06.
IR (KBr) cm$^{-1}$: 3450(br), 2974, 2410(br), 1653, 1629, 1274
NMR (DMSO-d$_6$δ ppm): 12.84(1H, s), 7.82(1H, d, J=9.0 Hz), 6.65(1H, d, J=9.0 Hz), 5.42(1H, m), 5.04 (1H, brs), 4.81(1H, m), 4.10–4.25(3H, m), 4.02 4.10(2H, m), 3.85–3.99(1H, m), 3.0–3.8(11H, m), 2.58(3H, s), 2.40–2.67(2H, m), 2.24(2H, m), 1.47 (2H, m), 0.89(3H, t, J=7.3 Hz)

EXAMPLE 3

5-Deoxy-5-[4-(1,3-di-n-butylxanthin-7-ylpropyl)piperazin-1-yl]-1.4;3.6-dianhydro-L-iditol 2-nitrate hydrochloride (Compound 3)

Compound 3 was obtained (yield: 28%) in a manner similar to Example 1 except that 1,3-di-n-butyl-7-(3-iodopropyl)xanthine was used in place of 1-chloro-3-phenylthiopropane and the period for heating under reflux was changed from 24 hours to 5 hours.

Melting point: 220°–221° C.
Elemental analysis: as $C_{26}H_{41}N_7O_7 \cdot 2.1HCl$.
Calcd. (%); C, 48.78 H, 6.79 N, 15.31.
Found (%); C, 48.77 H, 6.98 N, 15.18.
IR (KBr) cm$^{-1}$: 2960, 2420(br), 1696, 1650, 1644, 1278
NMR (DMSO-d$_6$) δ (ppm): 8.14(1H, s), 5.41(1H, m), 4.96 (1H, m), 4.76(1H, m), 4.38(2H, t, J=6.6 Hz), 4.07 4.17(1H, m), 4.02–4.08(2H, m), 3.99(2H, t, J=7.2 Hz), 3.88(2H, t, J=7.1 Hz), 3.12(2H, t, J=7.7 Hz), 2.8–4 2(10H, m), 2.20–2.35(2H, m), 1.59–1.73(2H, m), 1 46–1.59(2H, m), 1.20–1.40(4H, m), 0.90(6H, t, J=6.9 Hz)

EXAMPLE 4

5-(4-Cinnamylpiperazin-1-yl;-5-deoxy-1.4;3.6-dianhydro-L-iditol 2-nitrate hydrochloride (Compound 4)

A mixture of 1.20 g (4.63 mmols) of Compound b obtained in Reference Example 2, 0.65 ml (4.66 mmols) of triethylamine and 15 ml of methylene chloride was stirred at 0° C., and to this solution was dropwise added 5 ml of a solution of 0.92 g (4.67 mmols) of cinnamyl bromide in methylene chloride over 5 minutes. Stirring was continued at the same temperature for further an hour. The solution was washed with an aqueous saturated sodium bicarbonate solution and the methylene chloride layer was dried over anhydrous sodium sulfate. The solvent was evaporated under reduced pressure and the residue was purified by silica gel column chromatography (eluent: chloroform/methanol =25/1). The product was dissolved in ethanol, and to the solution was added ethyl acetate saturated with hydrogen chloride. The solvent was evaporated under reduced pressure, and the residue was dried to afford 0.85 g (yield: 42%) of Compound 4.

Melting point: 215°–216° C.
Elemental analysis: as $C_{19}H_{25}N_3O_5 \cdot 1.7HCl$.
Calcd. (%); C, 52.17 H, 6.15 N, 9.61.
Found (%); C, 52.10 H, 6.27 N, 9.52.
IR (KBr) cm$^{-1}$: 2976, 2360(br), 2200(br), 1634, 1268
NMR (DMSO-d$_6$δ ppm): 7.48(2H, m), 7.28–7.45(3H, m), 6.89(1H, d, J=15.9 Hz), 6.32–6.48(1H, m), 5.42(1H, m), 5.04(1H, m), 4.79(1H, m), 4.10–4.20(1H, m), 4.02–4.10(2H, m), 3.84–4.03(3H, m), 3.2–3.8(9H, m)

EXAMPLE 5

5-Deoxy-5-[4-(5-methyl-s-triazolo[1,5-a]pyrimidin-7-yl)-piperazin-1-yl]-1.4;3.6-dianhydro-L-iditol 2-nitrate hydrochloride (Compound 5)

A mixture of 1.00 g (3.86 mmols) of Compound b, 0.65 g (3.86 mmols) of 7-chloro-5-methyl-s-triazolo[1,5-a]-pyrimidine [Yakugaku Zasshi, 78, 1395 (1958)], 0.56 ml (4.02 mmols) of triethylamine and 25 ml of ethanol was stirred at room temperature for 40 minutes. The mixture was concentrated under reduced pressure, and the residue was purified by silica gel column chromatography (eluent: chloroform/methanol =20/1). The product was dissolved in ethanol, and to the solution was added ethyl acetate saturated with hydrogen chloride. The mixture was poured into cold diethyl ether and the precipitated crystals were taken out by filtration and dried to afford 0.85 g (yield: 45%) of Compound 5.

Elemental analysis: as $C_{16}H_{21}N_7O_5 \cdot 2.6HCl$.
Calcd. (%); C, 39.53 H, 4.89 N, 20.17.
Found (%); C, 39.69 H, 5.06 N, 19.20.
IR (KBr) cm$^{-1}$: 2940(br), 2580(br), 1645, 1583, 1278
NMR (DMSO-d$_6$) δ (ppm): 8.65(1H, s), 6.89(1H, s), 5.45 J=5.2, 2.3 Hz), 5.25–6.10 (1H, m), 5.36(1H, dd, (4H, m), 4.89(1H, m), 4.12–4.31(2H, m), 4.05–4.12 (2H, m), 3.95–4.06(1H, m), 3.30–3.75(4H, m), 2.55 (3H, s)

EXAMPLE 6

5-Deoxy-5-[(4-diphenylmethyl)piperazin-1-yl]-1.4;3.6-dianhydro-L-iditol 2-nitrate hydrochloride (Compound 6)

Compound 6 was obtained (yield: 35%) in a manner similar to Example 1 except that diphenylmethyl bromide was used in place of 1-chloro-3-phenylthiopropane, the period for heating under reflux was changed from 24 hours to 1 hour and a solvent mixture of ethanol and methylene chloride was used as the solvent for converting the product into the hydrochloride, instead of ethanol.

Melting point: 182°–183° C.
Elemental analysis: as $C_{23}H_{27}N_3O_5 \cdot 2HCl$.
Calcd. (%); C, 55.43 H, 5.87 N, 8.43.
Found (%); C, 54.59 H, 6.07 N, 8.10.
IR (KBr) cm$^{-1}$: 2950, 2370(br), 1653, 1644, 1275
NMR (DMSO-d$_6$δ ppm): 7.55-8- 15(4H, m), 7.20–7.55(6H, m), 5.43(1H, m), 5.15(1H, m), 4.80(1H, m), 2.70 4.25(14H, m)

EXAMPLE 7

5-[4-[3-(4-Acetyl-3-hydroxy-2-n-propylphenoxy)-2-hydroxypropyl]piperazin-1-yl]-5-deoxy-1.4;3.6-dianhydro-L-iditol 2-nitrate hydrochloride (Compound 7)

A mixture of 0.98 g (3.78 mmols) of Compound b, 0.98 g (3.92 mmols) of 4-(2,3-epoxypropyl)-2-hydroxy-3-n-propylacetophenone and 30 ml of ethanol was heated under reflux for 12 hours. The mixture was concentrated under reduced pressure, and the residue was purified by silica gel column chromatography (eluent: chloroform/methanol =25/1). Then, the product was treated in a manner similar to Example 1 to afford 1.01 g (yield: 46%) of Compound 7.

Melting point: 217°–218° C.
Elemental analysis: as $C_{24}H_{35}N_3O_9 \cdot 2HCl$.
Calcd. (%); C, 49.49 H, 6.40 N, 7.21.
Found (%); C, 49.57 H, 6.46 N, 7.28.

IR (KBr) cm$^{-1}$: 3380(br), 2964, 2400(br), 1655, 1630, 1275

NMR (DMSO-d$_6$) δ (ppm): 12.84(1H, s), 7.82(1H, d, J=9.0 Hz), 6.67(1H, d, J=9.0 Hz), 5.43(1H, m), 5.05 (1H, m), 4.81(1H, m), 4.45(1H, m), 3.99–4.21(5H, m), 3.88–4.00(1H, m), 3.0–3.9(11H, m), 2.59(3H, s), 2.53–2.67(2H, m), 1.48(2H, m), 0.89(3H, t, J=7.4 Hz)

EXAMPLE 8

5-Deoxy-5-[4-[2-hydroxy-3-(1,3-dihydro-1,3-dimethyl-2H-purin-2-on-6-ylthio)propyl]piperazin-1-yl]-1.4;3.6-dianhydro-L-iditol 2-nitrate hydrochloride (Compound 8)

A mixture of 1.02 g (3.93 mmols) of Compound b, 2.31 g (9.16 mmols) of 6-(2,3-epoxypropylthio)-1,3-dihydro-1,3-dimethyl-2H-purin-2-one, 25 m-1 of ethanol and 25 ml of chloroform was heated at 60° C. for 11 hours with stirring. The mixture was concentrated under reduced pressure, and the residue was purified by silica gel column chromatography (eluent: chloroform/methanol =25/1). The product was dissolved in ethanol and chloroform, and to the solution was added ethyl acetate saturated with hydrogen chloride. The precipitated crystals were taken out by filtration and dried to afford 0.35 g (yield: 14%) of Compound 8.

MS (FAB) m/z: 512 (M$^+$+1)
IR (KBr) cm$^{-1}$: 3480(br), 1698, 1650
NMR (DMSO-d$_6$) δ (ppm): 8.12 and 8.08(1H, s), 5.43(1H, m), 5.19(1H, m), 3.44 and 3.43(3H, s), 3.23(3H, s), 2.60–4.95(20H, m)

EXAMPLE 9

5-Deoxy-5-[4-[3-(4-methoxyphenylthio)propylpiperazin-1yl]-1.4;3.6-dianhydro-L-iditol 2-nitrate hydrochloride (Compound 9)

A mixture of 0.80 g (3.09 mmols) of Compound b, 0.67 g (3.09 mmols) of 1-chloro-3-(4-methoxyphenylthio)propane (Reference Example 7), 0.43 ml (3.08 mmols) of triethylamine, 0.69 g (4.60 mmols) of sodium iodide and 30 ml of methyl ethyl ketone was heated under reflux for 8 hours. The mixture was concentrated under reduced pressure, and the residue was purified by silica gel column chromatography (eluent: chloroform/methanol =40/1). The product was dissolved in chloroform, and to the solution was added ethyl acetate saturated with hydrogen chloride. The precipitated crystals were taken out by filtration and dried to afford 0.98 g (yield: 62%) of Compound 9.

Melting point 203.5°–204.5° C.
Elemental analysis: as C$_{20}$H$_{29}$N$_3$O$_6$S·2HCl.
Calcd. (%); C, 46.88 H, 6.10 N, 8.20.
Found (%); C, 46.31 H, 6.18 N, 8.04.
IR (KBr) cm$^{-1}$: 2956, 2346(br), 1643, 1272
NMR (DMSO-d$_6$) δ (ppm): 7.38(2H, d, J=8.8 Hz), 6.93(2H, d, J=8.8 Hz), 5.42(1H, m), 5.03(1H, m), 4.80(1H, m), 4.08–4.19(1H, m), 4.03–4.09(2H, m), 3.86–3.97 (1H, m), 3.75(3H, s), 3.4–4.5(5H, m), 3.1–3.4(6H, m), 2.92(2H, t, J=7.0 Hz), 1.93(2H, m)

EXAMPLE 10

5-[4-[3-(4-Chlorophenylthio)propyl]piperazin-1-yl]-5-deoxy-1.4;3.6-dianhydro-L-iditol 2-nitrate hydrochrolide (Compound 10)

1-Chloro-3-(4-chlorophenylthio)propane was obtained (yield: 96%) in a manner similar to Reference Example 7 except that 4-chlorothiophenol was used in place of 4-methoxythiophenol. Then, Compound 10 was obtained (yield: 67%) in the same manner as in Example 9.

Melting point: 201.5°–202.0° C.
MS (EI) m/z: 443 (M$^+$)
IR (KBr) cm$^{-1}$: 2882, 2400(br), 1644, 1275
NMR (DMSO-d$_6$) δ (ppm): 7.39(4H, s), 5.42(1H, m), 5.01 (1H, m), 4.79(1H, m), 4.08–4.19(1H, m), 4.03–4.09 (2H, m), 3.84–3.96(1H, m), 3.4–4.5(5H, m), 3.1 3.4(6H, m), 3.07(2H, t, J=7.2 Hz), 2.00(2H, m)

EXAMPLE 11

5-Deoxy-5-[4-[3-(3,4-dichlorophenylthio)propyl]piperazin-1-yl]-1.4;3.6-dianhydro-L-iditol 2-nitrate hydrochloride (Compound 11)

1-Chloro-3-(3,4-dichlorophenylthio)propane was obtained (yield: 97%) in a manner similar to Reference Example 7 except that 3,4-dichlorothiophenol was used in place of 4-methoxythiophenol. Then, Compound 11 was obtained (yield: 72%) in the same manner as in Example 9.

Melting point: 205.8°–206.0° C.
MS (FAB) m/z: 478 (M$^+$+1)
IR (KBr) cm$^{-1}$: 2980, 2380(br), 1644, 1273
NMR (DMSO-d$_6$) δ (ppm): 7.63(1H, d, J=2.1 Hz), 7.57(1H, d, J=8.5 Hz), 7.35(1H, dd, J=8.5, 2.1 Hz), 5.41(1H, 85 m), 5.01(1H, m), 4.79(1H, m), 3.4–4.5(9H, m), 3.1–3.4(6H, m), 3.13(2H, t, J=7.2 Hz), 2.02(2H, m)

EXAMPLE 12

5-Deoxy-5-[4-[3-(pyridin-4-ylthio)propyl]piperazin-1-yl]-1.4;3.6-dianhydro-L-iditol 2-nitrate hydrochloride (Compound 12)

1-Chloro-3-(pyridin-4-ylthio)propane was obtained (yield: 95%) in a manner similar to Reference Example 7 except that 4-pyridinethiol was used in place of 4-methoxythiophenol. Then, Compound 12 was obtained (yield: 50%) in the same manner as in Example 9 except that the period for heating under reflux was changed from 8 hours to 5 hours.

Melting point: 207.7°–208.5° C.
MS (EI) m/z: 410 (M$^+$)
IR (KBr) cm$^{-1}$: 2920(br), 2550(br), 1627, 1276
NMR (DMSO-d$_6$ δ ppm): 8.66(2H, d, J=6.8 Hz), 7.96(2H, d, J=6.8 Hz), 5.42(1H, m), 5.06(1H, m), 4.81(1H, m), 4.1–4.2(1H, m), 4.0–4.1(2H, m), 3.85–4.0(1H, m), 3.0–4.5(13H, m), 2.17(2H, m)

EXAMPLE 13

4-Deoxy-5-[4-[3-(pyrimidin-2-ylthio)propyl]piperazin-1-yl]-1.4;3.6-dianhydro-L-iditol 2-nitrate hydrochloride (Compound 13)

1-Chloro-3-(pyrimidin-2-ylthio)propane was obtained (yield: 21%) in a manner similar to Reference Example 7 except that 2-mercaptopyrimidine was used in place of 4-methoxythiophenol. Then, Compound 13 was obtained (yield: 10%) in the same manner as in Example 9.

Melting point: 205.5°–206.0° C.
Elemental analysis: as C$_{17}$H$_{25}$N$_5$O$_5$S·3HCl.
Calcd. (%); C, 39.20 H, 5.42 N, 13.45.
Found (%); C, 39.69 H, 5.67 N, 13.41.
IR (KBr) cm$^{-1}$: 2976, 2340(br), 1650, 1276
NMR (DMSO-d$_6$ δ ppm): 8.65(2H, d, J=4.9 Hz), 7.24(1H, t, J=4.9 Hz), 5.43(1H, m), 5.11(1H, m), 4.83(1H, m), 4.1–4.25(1H, m), 4.07(2H, m), 3.90–4.05(1H, m), 3.3–5.0(9H, m), 3.28(2H, t, J=7.7 Hz), 3.20 (2H, t, J=7.1 Hz), 2.15(2H, m)

EXAMPLE 14

5-[4-[3-(2-ethoxycarbonylphenylthio)propyl]piperazin-1-yl]-5-deoxy-1.4;3.6-dianhydro-L-iditol 2-nitrate hydrochloride (Compound 14)

Compound 14 was obtained (yield: 50%) in a manner similar to Example 9 except that 1-chloro-3-(2-ethoxycarbonylphenylthio)propane (Reference Example 8) was used in place of 1-chloro-3-(4-methoxyphenylthio)propane.

Melting point: 186.3°–186.8° C.
Elemental analysis: as $C_{22}H_{31}N_3O_7S \cdot 2HCl$.
Calcd. (%); C, 47.65 H, 6.00 N, 7.58.
Found (%); C, 47.38 H, 6.12 N, 7.46.
IR (KBr) $cm^{-1}$: 2982 2360(br), 1705, 1642, 1272
NMR (DMSO-$d_6$) δ (ppm): 7.87(1H, dd, J=7.8, 1.5 Hz), 7.56(1H, m), 7.28(1H, d, J=7.8 Hz), 7.26(1H, dd, J=7.8, 7.8 Hz), 5.42(1H, m), 5.02(1H, m), 4.79(1H, m), 4.29(2H, q, J=7.1 Hz), 3.05(2H, t, J=7.3 Hz), 2.9–4.6(15H, m), 2.07(2H, m), 1.32(3H, t, J=7.1 Hz)

EXAMPLE 15

5-Deoxy-5-[4-[3-(4-ethoxycarbonylmethylphenylthio)-propyl]-piperazin-1-yl]-1.4;3.6-dianhydro-L-iditol 2-nitrate hydrochloride (Compound 15)

Compound 15 was obtained (yield: 70%) in a manner similar to Example 9 except that 1-chloro-3-(4-ethoxycarbonylmethylphenylthio)propane (Reference Example 9) was used in place of 1-chloro-3-(4-methoxyphenylthio)propane.

Melting point: 194°–195° C.
Elemental analysis: as $C_{23}H_{33}N_3O_7S \cdot 2HCl$.
Calcd. (%); C, 48.59 H, 6.21 N, 7.39.
Found (%); C, 48.76 H, 6.25 N, 7.39.
IR (KBr) $cm^{-1}$: 2980, 2410(br), 1731, 1638, 1276
NMR (DMSO-$d_6$ δ ppm): 7.33(2H, d, J=8.3 Hz), 7.23(2H, d, J=8.3 Hz), 5.41(1H, m), 5.01(1H, m), 4.79(1H, m), 3.64(2H, s), 3.4–4.5(11H, m), 3.1–3.4(6H, m), 3.04(2H, t, J=7.1 Hz), 2.01(2H, m), 1.18(3H, t, J=7.1 Hz)

EXAMPLE 16

5-[4-[3-(4-Carboxymethylphenylthio)propyl]piperazin-1-yl]-5-deoxy-1.4;3.6-dianhydro-L-iditol 2-nitrate (Compound 16)

A mixture of 1.87 g (3.77 mmols) of the free form of Compound 15 obtained in Example 15, 0.40 g (10.00 mmols) of sodium hydroxide, 25 ml of water, 25 ml of ethanol and 50 ml of tetrahydrofuran was stirred at room temperature for 20 minutes, and then, the pH of the reaction mixture was adjusted with dil. hydrochloric acid to pH 6 -7. The mixture was concentrated under reduced pressure, and the residue was purified by silica gel column chromatography (eluent: chloroform/methanol =5/1) and recrystallized from isopropyl alcohol/water. The crystals were taken out by filtration and dried to afford 1.38 g (yield: 78%) of Compound 16.

Melting point: 129°–130° C.
Elemental analysis: as $C_{21}H_{29}N_3O_7S$.
Calcd. (%); C, 53.95 H, 6.25 N, 8.99.
Found (%) C 53 96 H, 6.27 N, 8.82.
IR (KBr) $cm^{-1}$: 3420(br), 2922(br), 1695, 1636, 1275
NMR (DMSO-$d_6$) δ (ppm): 7.26(2H, d, J=8.3 Hz), 7.19(2H, d, J=8.3 Hz), 5.35(1H, m), 4.62(2H, m), 3.85–4.10 (3H, m), 3.53(2H, s), 3.5–ː(1H, m), 2.94(2H, t, J=7.3 Hz), 2.78(1H, m), 2.15–2.65(10H, m), 1.68 (2H, m)

EXAMPLE 17

5-Deoxy-5-[4-[3-(4-ethoxycarbonylphenylthio)propyl]-piperazin-1-yl]-1.4;3.6-dianhydro-L-iditol 2-nitrate hydrochloride (Compound 17)

1-Chloro-(4-ethoxycarbonylphenylthio)propane was obtained (yield: 30%) in a manner similar to Reference Example 9 except that 4-aminobenzoic acid was used in place of 4-aminophenylacetic acid. Then, Compound 17 was obtained in a manner similar to Example 15 (yield: 63%).

Melting point: 193.0°–193.7° C.
Elemental analysis: as $C_{22}H_{31}N_3O_7S \cdot 2HCl$.
Calcd. (%); C, 47.65 H, 6.00 N, 7.58.
Found (%); C, 47.70 H, 6.15 N, 7.47.
IR (KBr) $cm^{-1}$: 2984, 2390(br), 1709, 1641, 1275
NMR (DMSO-$d_6$) δ (ppm): 7.88(2H, d, J=8.5 Hz), 7.45(2H, d, J=8.5 Hz), 5.42(1H, m), 5.02(1H, m), 4.80(1H, m), 4.30(2H, q, J=7.1 Hz), 4.08–4.18(1H, m), 4.00 4.09(2H, m), 3.85–3.97(1H, m), 3.17(2H, t, J=7.3 Hz), 3.0–4.7(11H, m), 2.08(2H, m), 1.31(3H, t, J=7.1 Hz)

EXAMPLE 18

5-Deoxy-5-[4-(2-phenylthioethyl)piperazin-1-yl]-1.4;3.6-dianhydro-L-iditol 2-nitrate hydrochloride (Compound 18)

1-Chloro-2-phenylthioethane was obtained (yield: 89%) in a manner similar to Reference Example 7 except that thiophenol and 1-bromo-2-chloroethane were used in place of 4-methoxythiophenol and 1-bromo-3-chloropropane, respectively. Then, Compound 18 was obtained in the same manner as in Example 9 (yield: 47%).

Melting point: 209.3°–209.8° C.
Elemental analysis: as $C_{18}H_{25}N_3O_5S \cdot 2HCl$.
Calcd. (%); C, 46.16 H, 5.81 N, 8.9.
Found (%); C, 45.79, H, 5.97 N, 8.94.
IR (KBr) $cm^{-1}$: 2984, 2362(br), 1645, 1274
NMR (DMSO-$d_6$ δ ppm): 7.2–7.5(5H, m), 5.42(1H, m), 5.03(1H, m), 4.79(1H, m), 4.08–4.19(1H, m), 4.00 4.10(2H, m), 3.84–3.98(1H, m), 2.9–5.2(13H, m)

EXAMPLE 19

5-[4-[3-(benzothiazol-2-ylthio)propyl]piperazin-1-yl]-5-deoxy-1.4;3.6-dianhydro-L-iditol 2-nitrate hydrochloride (Compound 19)

1-(Benzothiazol-2-ylthio)-3-chloropropane was obtained (yield 83%) in a manner similar to Reference Example 7 except that 2-mercaptobenzothiazole was used in place of 4-methoxythiophenol. Then, Compound 19 was obtained (yield: 31%) in the same manner as in Example 9 except that the period for heating under reflux was changed from 8 hours to 4 hours.

Melting point: 213.5°–214.0° C.
Elemental analysis: as $C_{20}H_{26}N_4O_5S_2 \cdot 3HCl$.
Calcd. (%); C, 41.71 H, 5.08 N, 9.73.
Found (%); C, 41.92 H, 5.31 N, 9.73.
IR (KBr) $cm^{-1}$: 2960(br), 2368(br), 1635, 1275
NMR (DMSO-d ) δ (ppm): 8.02(1H, d, J=7.7 Hz), 7.87(1H, d, J=7.5 Hz), 7.48(1H, m), 7.38(1H, m), 5.42(1H, m), 5.09(1H, m), 4.82(1H, m), 4.10–4.22(1H, m), 4.03–4.10(2H, m), 3.90–4.03(1H, m), 3.49(2H, t, J=7.1 Hz), 3.0–5.1(11H, m), 2.27(2H, m)

EXAMPLE 20

5-Deoxy-5-[4-(3-phenoxypropyl)piperazin-1-yl]-1.4;3.6-dianhydro-L-iditol 2-nitrate hydrochloride (Compound 20)

1-Chloro-3-phenoxypropane was obtained (yield: 58%) in a manner similar to Reference Example 7 except that phenol was used in place of 4-methoxythiophenol. Then, Compound 20 was obtained (yield: 73%) in the same manner as in Example 9.

Melting point: 207.3°–208.5° C.
Elemental analysis: as $C_{19}H_{27}N_3O_6 \cdot 2HCl$.
Calcd. (%); C, 48.93 H, 6.27 N, 9.01.
Found (%); C, 49.26 H, 6.41 N, 9.04.
IR (KBr) cm$^{-1}$: 2954, 2362(br), 1643, 1278
NMR (DMSO-d$_6$δ ppm): 7.30(2H, m), 6.85–7.05(3H, m), 5.42(1H, m), 5.04(1H, m), 4.80(1H, m), 4.10–4.20 (1H, m), 4.00–4.11(2H, m), 3.85–3.99(1H, m), 3.0 5.1(13H, m), 2.19(2H, m)

EXAMPLE 21

5-Deoxy-5-[4-[3-(imidazol-1-yl)propyl]piperazin-1-yl]-1.4;3.6-dianhydro-L-iditol 2-nitrate hydrochloride (Compound 21)

1-Chloro-3-(imidazol-1-yl)propane was obtained (yield: 46%) in a manner similar to Reference Example 7 except that imidazole was used in place of 4-methoxythiophenol (eluent: chloroform/methanol =10/1). Then, Compound 21 was obtained (yield: 26%) in the same manner as in Example 9 (eluent: chloroform/methanol =20/1).

MS (FAB) m/z: 368 (M$^+$+1)
IR (KBr) cm$^{-1}$: 2950 2550(br) 1642 1278
NMR (DMSO-d$_6$) 6 (ppm): 9.26(1H, s), 7.85(1H, m), 7.72 (1H, m), 5.43(1H, m), 5.09(1H, m), 4.82(1H, m), 4.38(2H, t, J=6.8 Hz), 4.10–4.22(1H, m), 4.04–4.11 (2H, m), 3.90–4.03(1H, m), 3.17(2H, t, J=7.1 Hz), 3.0–5.0(9H, m), 2.33(2H, m)

EXAMPLE 22

5-[4-[3-(Benzimidazol-1-yl)propyl]piperazin-1-yl]-5-deoxy-1.4;3.6-dianhydro-L-iditol 2-nitrate hydrochloride (Compound 22)

1-(Benzimidazol-1-yl)-3-chloropropane was obtained (yield: 86%) in a manner similar to Reference Example 7 except that benzimidazole was used in place of 4-methoxythiophenol (eluent: chloroform/methanol =50/1). Then, Compound 22 was obtained (yield: 35%) in the same manner as in Example 9 except that the period for heating under reflux was changed from 8 hours to 5 hours.

Melting point: 216.5°–217.5° C.
MS (EI) m/z: 417 (M$^+$)
IR (KBr) cm$^{-1}$: 2950(br), 2500(br), 1641, 1277
NMR (DMSO-d$_6$) 6 (ppm): 9.66(1H, s), 8.05–8.14(1H, m), 7 87–7.98(1H, m), 7.60–7.75(2H, m), 5.40(1H, m), 4 80–4.87(1H, m), 4.69–4.75(1H, m), 4.64(2H, t, J=7.2 Hz), 4.00–4.13(1H, m), 2.7–3.9(14H, m), 2.40(2H, m)

EXAMPLE 23

5-Deoxy-5-[4-[3-(5,6-dimethylbenzimidazol-1-yl)propyl]-piperazin-1-yl]-1.4;3.6-dianhydro-L-iditol 2-nitrate hydrochloride (Compound 23)

1-Chloro-3-(5,6-dimethylbenzimidazol-1-yl)propane was obtained (yield: 62%) in a manner similar to Reference Example 7 except that 5,6-dimethylbenzimidazole was used in place of 4-methoxythiophenol (eluent: chloroform/methanol =50/1). Then, Compound 23 was obtained (yield: 44%) in the same manner as in Example 9 except that the period for heating under reflux was changed from 8 hours to 5 hours.

Melting point: 225.8°–226.8° C.
MS (EI) m/z: 445 (M$^+$)
IR (KBr) cm$^{-1}$: 2970, 2356(br), 1635, 1275
NMR (DMSO-d$_6$δ ppm): 9.66(1H, s), 7.92(1H, s), 7.66 (1H, s), 5.42(1H, m), 5.03(1H, m), 4.79(1H, m), 4.61(2H, t, J=6.6 Hz), 3.0–4.5(15H, m), 2.42(3H, s), 2.41(3H, s), 2.3–2.5(2H, m)

EXAMPLE 24

5-Deoxy-5-[4-[3-(4,5-dimethylbenzimidazol-1-yl)propyl]-piperazin-1-yl]-1.4;3.6-dianhydro-L-iditol 2-nitrate hydrochloride (Compound 24) and 5-deoxy-5-[4-[3-(6,7-dimethylbenzimidazol-1-yl)propyl]piperazin-1-yl]-1.4;3.6-dianhydro-L-iditol 2-nitrate hydrochloride (Compound 25)

A mixture of 1-chloro-3-(4,5-dimethylbenzimidazol-1-yl)propane and 1-chloro-3-(6,7-dimethylbenzimidazol-1-yl)propane was obtained (yield: 100%) in a manner similar to Reference Example 7 except that 4,5-dimethylbenzimidazole was used in place of 4-methoxythiophenol. Then, a mixture of Compound 24 and Compound 25 (about 21 :1) was obtained (yield: 58%) in the same manner as in Example 9 except that the period for heating under reflux was changed from 8 hours to 5 hours.

Melting point: 222°–223° C.
MS (EI) m/z: 445 (M$^+$)
IR (KBr) cm$^{-1}$: 2975(br), 2340(br), 1634, 1275
NMR (DMSO-d$_6$) δ (ppm): 9.78 and 9.67(1H, s), 7.80 and 7.61(1H, d, J=8.6 Hz), 7.46(1H, d, J=8.6 Hz), 5.42 (1H, m), 5.01(1H, m), 4.77(1H, m), 4.62(2H, t, J=6 8 Hz), 2.9–4.5(15H, m), 2.56(3H, s), 2.42(3H, s), 2.30–2.50(2H, m)

EXAMPLE 25

5-Deoxy-5-[4-[3-(5,6-dimethoxybenzimidazol-1-yl)propyl]-piperazin-1-yl]-1.4;3.6-dianhydro-L-iditol 2-nitrate hydrochloride (Compound 26)

1-Chloro-3-(5,6-dimethoxybenzimidazol-1-yl)propane was obtained (yield: 78%) in a manner similar to Reference Example 7 except that 5,6-dimethoxybenzimidazole was used in place of 4-methoxythiophenol. Then, Compound 26 was obtained (yield: 36%) in the same manner as in Example 9 except that the period for heating under reflux was changed from 8 hours to 5 hours.

Melting point: 224.5°–226.0° C.
Elemental analysis: as $C_{22}H_{31}N_5O_7 \cdot 3HCl$.
Calcd. (%); C, 45.02 H, 5.84 N, 11.93.
Found (%); C, 44.94 H, 5.86 N, 11.83.
IR (KBr) cm$^{-1}$: 2970(br), 2420(br), 1642, 1274
NMR (DMSO-d$_6$) 6 (ppm): 9.56(-1H, s), 7.72(1H, s), 7.31 (1H, s), 5.42(1H, m), 5.05(1H, m), 4.80(1H, m), 4 65(2H, t, J=6.8 Hz), 4.09–4.20(1H, m), 4.02–4.10 (2H, m), 3.94(3H, s), 3.88(3H, s), 3.0–4.1(12H, m), 2.41(2H, m)

EXAMPLE 26

5-Deoxy-5-[4-[3-(indol-1-yl)propyl]piperazin-1-yl]-1.4;3.6-dianhydro-L-iditol 2-nitrate hydrochloride (Compound 27)

1-Chloro-3-(indol-1-yl)propane was obtained (yield: 100%) in a manner similar to Reference Example 7 except that indole was used in place of 4-methoxythiophenol. Then, Compound 7 was obtained (yield: 44%) in the same manner as in Example 9 except that the period for heating under reflux was changed from 8 hours to 5 hours.

Melting point: higher than 300° C.
MS (EI) m/z: 416 (M+)
(KBr) cm$^{-1}$: 2980(br), 2410(br), 1640, 1278
NMR (DMSO-d$_6$) 6 (ppm): 7.49–7.61(2H, m), 7.39–7.48(1H, m), 7.14(1H, m), 7.03(1H, m), 6.45(1H, m), 5.41 (1H, m), 5.05(1H, m), 4.80(1H, m), 4.30(2H, t, J=7.1 Hz), 3.15(2H, t, J=7.9 Hz), 3.0–5.1(13H, m), 2.23(2H, m)

EXAMPLE 27

5-[4-[3-(Benzotriazol-1-yl)propyl]piperazin-1-yl]-5-deoxy-1.4;3.6-dianhydro-L-iditol 2-nitrate hydrochloride (Compound 28)

Compound 28 was obtained (yield: 51%) in a manner similar to Example 9 except that 1-(benzotriazol-1-yl)-3-chloropropane (Compound f in Reference Example 10) was used in place of 1-chloro-3-(4-methoxyphenylthio)-propane and the period for heating under reflux was changed from 8 hours to 5 hours.

Melting point: 206.5°–208.0° C.
Elemental analysis: as C$_{19}$H$_{26}$N$_6$O$_5$·2HCl.
Calcd. (%); C, 45.76 H, 5.70 N, 16.85.
Found (%); C, 45.74 H, 5.81 N, 16.59.
IR (KBr) cm$^{-1}$: 2982, 2360(br), 1639, 1278
NMR (DMSO-d ) 6 (ppm): 8.05(1H, d, J=8.4 Hz), 7.95(1H, d, J=8.4 Hz), 7.58(1H, m), 7.42(1H, m), 5.41(1H, m), 4.94(1H, m), 4.84(2H, t, J=7.0 Hz), 4.75(1H, m), 2.8–4.2(15H, m), 2.42(2H, m)

EXAMPLE 28

5-[4-[3-(Benzotriazol-2-yl)propyl]piperazin-1-yl]-5-deoxy-1.4;3.6-dianhydro-L-iditol 2-nitrate hydrochloride (Compound 29)

Compound 29 was obtained (yield: 40%) in a manner similar to Example 9 except that 1-(benzotriazol-2-yl)-3-chloropropane (Compound g in Reference Example 10) was used in place of 1-chloro-3-(4-methoxyphenylthio)-propane.

Melting point: 211.5°–213.0° C.
Elemental analysis: as C$_{19}$H$_{26}$N$_6$O$_5$·2HCl.
Calcd. (%); C, 46.44 H, 5.74 N, 17.10.
Found (%); C, 46.56 H, 5.77 N, 16.87.
IR (KBr) cm$^{-1}$: 2984, 2364(br), 1642, 1278
NMR (DMSO-d$_6$δ ppm): 7.92(2H, m), 7.45(2H, m), 5.42 (1H, m), 4.95(1H, m), 4.88(2H, t, J=6.9 Hz), 4.77 (1H, m), 4.07–4.17(1H, m), 4.01–4.08(2H, m), 2.7 4.2(12H, m), 2.52(2H, m)

EXAMPLE 29

5-Deoxy-5-[4-[3-(indazol-1-yl)propyl]piperazin-1-yl]-1.4; 3.6-dianhydro-L-iditol 2-nitrate hydrochloride (Compound 30)

Compound 30 was obtained (yield: 29%) in a manner similar to Example 9 except that 1-chloro-3-(indazol-1-yl)propane (Compound h in Reference Example 11) was used in place of 1-chloro-3-(4-methoxyphenylthio)-propane and the period for heating under reflux was changed from 8 hours to 4 hours.

Melting point: 197.0°–198.5° C.
Elemental analysis: as C$_{20}$H$_{27}$N$_5$O$_5$·2.5HCl.
Calcd. (%); C, 47.23 H, 5.85 N, 13.77.
Found (%); C, 47.28 H, 6.07 N, 13.74.
IR (KBr) cm$^{-1}$: 2950(br), 2420(br), 1642, 1275
NMR (DMSO-d$_6$δ ppm): 8.09(1H, s), 7.77(1H, d, J=8.1 Hz), 7.72(1H, d, J=8.6 Hz), 7.41(1H, m), 7.15(1H, m), 5.41(1H, m), 4.94(1H, m), 4.75(1H, m), 4.52 (2H, t, J=6.9 Hz), 2.8–4.3(15H, m), 2.31(2H, m)

EXAMPLE 30

5-Deoxy-5-[4-[3-(indazol-2-yl)propyl]piperazin-1-yl]-1.4; 3.6-dianhydro-L-iditol 2-nitrate hydrochloride (Compound 31)

Compound 31 was obtained (yield: 28%) in a manner similar to Example 9 except that 1-chloro-3-(indazol-2-yl)propane (Compound i in Reference Example 11) was used in place of 1-chloro-3-(4-methoxyphenylthio)-propane and the period for heating under reflux was changed from 8 hours to 4 hours.

Melting point: 204.5°–205.5° C.
IR (KBr) cm$^{-1}$: 2950(br), 2420(br), 1640, 1275
NMR (DMSO-d$_6$) 6 (ppm): 8.43(1H, s), 7.71(1H, d, J=8.2 Hz), 7.61(1H, d, J=8.8 Hz), 7.25(1H, m), 7.04(1H, m), 5.42(1H, m), 5.05(1H, m), 4.79(1H, m), 4.58 (2H, t, J=6.7 Hz), 4.09–4.19(1H, m), 4.03–4.09(2H, m), 3.19(2H, t, J=7.8 Hz), 3.0–4.3(10H, m), 2.42 (2H, m)

EXAMPLE 31

5-[4-[3-(4-Azabenzimidazol-3-yl)propyl]piperazin-1-yl]-5-deoxy-1.4;3.6-dianhydro-L-iditol 2-nitrate hydrochloride (Compound 32)

1-(4-Azabenzimidazol-3-yl)-3-chloropropane was obtained (yield: 44%) in a manner similar to Reference Example 7 except that 4-azabenzimidazole was used in place of 4-methoxythiophenol. Then, Compound 32 was obtained (yield: 24%) in the same manner as in Example 9 except that the period for heating under reflux was changed from 8 hours to 6 hours.

Melting point: 208.3°–208.8° C.
MS (EI) m/z: 418 (M+)
IR (KBr) cm ): 2970(br), 2400(br), 1640, 1274
NMR [DMSO-d$_6$δ ppm): 9.62(1H, s), 8.65(1H, d, J=4.8 Hz), 8.33(1H, d, J=8.2 Hz), 7.61(1H, dd, J=8.2, 4.8 Hz), 5.43(1H, m), 5.13(1H, m), 4.82(1H, m), 4.61(2H, t, J=6.6 Hz), 4.11–4.22(1H, m), 4.08(2H, m), 3.95–4.05(1H, m), 3.81(1H, m), 3.34–3.74(8H, m), 3.28(2H, t, J=7.7 Hz), 2.47(2H, m)

EXAMPLE 32

5-Deoxy-5-[4-[3-(5-methoxybenzimidazol-1-yl)propyl]-piperazin-1-yl]-1.4;3.6-dianhydro-L-iditol 2-nitrate hydrochloride (Compound 33) and
5-deoxy-5-[4-[3-(6-methoxybenzimidazol-1yl)propyl]-piperazin-1-yl]-1.4;3.6-dianhydro-L-iditol 2nitrate hydrochloride (Compound 34)

A mixture of 1-chloro-3-(5-methoxybenzimidazol-1-yl)propane and 1-chloro-3-(6-methoxybenzimidazol-1-yl)propane was obtained (yield: 19%) in a manner similar to Reference Example 7 except that 5-methoxybenzimidazole was used in place of 4-methoxythiophenol. Then, a mixture of Compound 33 and Compound 34 (about 1:1) was obtained (yield: 38%) in the same manner as in Example 9 except that the period for heating under reflux was changed from 8 hours to 5 hours.

Melting point: 227.8°–228.5° C.
Elemental analysis: as C$_{21}$H$_{29}$N$_5$O$_6$·3HCl.
Calcd. (%); C, 45.29 H, 5.79 N, 12.58.
Foun (%); C, 45.24 H, 5.88 N, 12.49.

IR (KBr) cm$^{-1}$: 2975(br), 2360(br), 1632, 1275
NMR (DMSO-d$_6$δ ppm): 9.68 and 9.66(1H, s), 7.20–8.17 (3H, m), 5.42(1H, m), 5.02(1H, m), 4.78(1H, m), 4.65(2H, m), 3.92 and 3.88(3H, s), 3.27(2H, t, J=7.3 Hz), 2.9–4.5(13H, m), 2.42(2H, m)

EXAMPLE 33

5-[4-[3-(5-Chlorobenzimidazol-1-yl)propyl]piperazin-1-yl]-5-deoxy-1.4;3.6-dianhydro-L-iditol 2-nitrate hydrochloride (Compound 35) and
5-[4-[3-(6-chlorobenzimidazol-1-yl)propyl]piperazin-1-yl]-5-deoxy-1.4;3.6-dianhydro-L-iditol 2-nitrate hydrochloride (Compound 36)

A mixture of 1-chloro-3-(5-chlorobenzimidazol-1-yl)propane and 1-chloro-3-(6-chlorobenzimidazol-1-yl)propane was obtained (yield: 77%) in a manner similar Reference Example 7 except that 5-chlorobenzimidazole was used in place of 4-methoxythiophenol. Then, a mixture of Compound 35 and Compound 36 (about 1:1) was obtained (yield: 42%) in the same manner as in Example 9 except that the period for heating under reflux was changed from 8 hours to 4 hours.
  Melting point: 227.0°–228.5° C.
  Elemental analysis: as C$_{20}$H$_{26}$ClN$_5$O$_5$·3HCl.
  Calcd. (%); C, 42.80 H, 5.21 N, 12.48.
  Found (%); C, 42.88 H, 5.34 N, 12.41.
  IR (KBr) cm$^{-1}$: 2960(br), 2350(br), 1633, 1276
  NMR (DMSO-d$_6$δ ppm): 9.62 and 9.59(1H, s), 7.58–8.33 (3H, m), 5.42(1H, m), 5.05(1H, m), 4.79(1H, m), 4.63(2H, m), 4.10–4.21(1H, m), 4.04–4.11(2H, m), 3.90–4.01(1H, m), 3.00–3.85(11H, m), 2.39(2H, m)

Example 34

5-Deoxy-5-[4-[3-(5,6-dichlorobenzimidazol-1-yl)propyl]-piperazin-1-yl]-1.4;3.6-dianhydro-L-iditol 2-nitrate hydrochloride (Compound 37)

1-Chloro-3-(5,6-dichlorobenzimidazol-1-yl)propane was obtained (yield: 45%) in a manner similar to Reference Example 7 except that 5,6-dichlorobenzimidazole was used in place of 4-methoxythiophenol. Then, Compound 37 was obtained (yield: 52%) in the same manner as in Example 9 except that the period for heating under reflux was changed from 8 hours to 4 hours.
  Melting point: 228.0°–229.5° C.
  Elemental analysis: as C$_{20}$H$_{25}$Cl$_2$N$_5$O$_5$·3HCl.
  Calcd. (%); C, 40.32 H, 4.74 N, 11.76.
  Found (%); C, 40.36 H, 4.80 N, 11.79.
  IR (KBr) cm$^{-1}$: 2965(br), 2350(br), 1642, 1276
  NMR (DMSO-d$_6$) δ (ppm): 9.15(1H, s), 8.38(1H, s), 8.08 (1H, s), 5.43(1H, m), 5.09(1H, m), 4.81(1H, m), 4.54(2H, t, J=7.0 Hz), 4.11–4.21(1H, m), 4.03–4.11 (2H, m), 3.92–4.04(1H, m), 3.22(2H, t, J=7.4 Hz), 3.00–3.85(9H, m), 2.34(2H, m)

EXAMPLE 35

5-[4-(Benzimidazol-2-ylmethyl)piperazin-1-yl]-5-deoxy-1.4;3.6-dianhydro-L-iditol 2-nitrate hydrochloride (Compound 38)

A mixture of 1.55 g (5.98 mmols) of Compound b obtained in Reference Example 2, 0.97 g (5.82 mmols) of 2-chloromethylbenzimidazole, 1.31 g (8.74 mmols) of sodium iodide and 40 ml of methyl ethyl ketone was heated under reflux for an hour and a half. The mixture was concentrated under reduced pressure, and the residue was purified by silica gel column chromatography (eluent: chloroform/methanol =25/1). The product was dissolved in chloroform and to this solution was added ethyl acetate saturated with hydrogen chloride. The mixture was poured into cold diethyl ether and the precipitate crystals were taken out by filtration and dried to afford 1.30 g (yield: 44%) of Compound 38.
  MS (EI) m/z: 389 (M$^+$)
  IR (KBr) cm$^{-1}$: 2930(br), 1648, 1278
  NMR (DMSO-d$_6$) δ (ppm): 7.83(2H, m), 7.55(2H, m), 5.45 (1H, m), 5.30(1H, m), 4.85(1H, m), 4.26(2H, s), 2.7–4.6(14H, m)

EXAMPLE 36

5-[4-[3-(7-Azaindol-1-yl)propyl]piperazin-1-yl]-5-deoxy-1.4;3.6-dianhydro-L-iditol 2-nitrate hydrochloride (Compound 39)

1-(7-Azaindol-1-yl)-3--chloropropane was obtained (yield: 72%) in a manner similar to Reference Example 7 except that 7-azaindole was used in place of 4-methoxythiophenol. Then, Compound 39 was obtained (yield: 10%) in the same manner as in Example 9.
  MS (EI) m/z: 417 (M$^+$)
  IR (KBr) cm$^{-1}$: 2940(br), 1637, 1277
  NMR (DMSO-d$_6$δ ppm): 8.34(1H, d, J=5.2 Hz), 8.19(1H, d, J=7.7 Hz), 7.72(1H, d, J=3.5 Hz), 7.25(1H, dd, J=7.7, 5.2 Hz), 6.63(1H, d, J=3.5 Hz), 5.42(1H, m), 5.10(1H, m), 4.82(1H, m), 4.46(2H, t, J=6.9 Hz), 3.28–5.00(13H, m), 3.20(2H, t, J=7.8 Hz), 2.30(2H, m)

EXAMPLE 37

5-Deoxy-5-[4-[3-(5-nitrobenzimidazol-1-yl)propyl]piperazin-1-yl]-1.4;3.6-dianhydro-L-iditol 2-nitrate hydrochloride (Compound 40) and
5-deoxy-5-[4-[3-(6-nitrobenzimidazol-1-yl)propyl]piperazin-1-yl]-1.4;3.6-dianhydro-L-iditol 2-nitrate hydrochloride (Compound 41)

A mixture of 1-chloro-3-(5-nitrobenzimidazol-1-yl)propane and 1-chloro-3-(6-nitrobenzimidazol-1-yl)propane was obtained (yield: 69%) in a manner similar to Reference Example 7 except that 5-nitrobenzimidazole was used in place of 4-methoxythiophenol. Then, a mixture of Compound 40 and Compound 41 (about 58:42) was obtained (yield: 72%) in the same manner as in Example 9 except that the period for heating under reflux was changed from 8 hours to 5 hours.
  Melting point: 212°–213° C.
  MS (FAB) m/z: 463 (M$^+$+1)
  IR (KBr) cm$^{-1}$: 2990, 2550(br), 1636, 1276
  NMR (DMSO-d$_6$δ ppm): 7.93–9.17(4H, m), 5.43(1H, m), 5.08(1H, m), 4.80(1H, m), 4.51–4.69(2H, m), 3.1 4.4(15H, m), 2.35(2H, m)

EXAMPLE 38

5-Deoxy-5-[4-[3-(2-methylbenzimidazol-1-yl)propyl]-piperazin-1-yl]-1.4;3.6-dianhydro-L-iditol 2-nitrate hydrochloride (Compound 42)

1-Chloro-3-(2-methylbenzimidazol-1-yl)propane was obtained (yield: 86%) in a manner similar to Reference Example 7 except that 2-methylbenzimidazole was used in place of 4-methoxythiophenol. Then, Compound 42 was obtained (yield: 64%) in the same manner as in Example 9 except that the period for heating under reflux was changed from 8 hours to 5 hours.
  MS (EI) m/z: 431 (M$^+$)
  IR (KBr) cm$^{-1}$: 2950(br), 2450(br), 1640, 1277
  NMR (DMSO-d$_6$) δ (ppm): 8.07(1H, m), 7.81(1H, m), 7.58 (2H, m), 5.42(1H, m), 5.04(1H, m), 4.80(1H, m), 4.57(2H, t, J=7.2 Hz), 3.1–4.4(15H, m), 2.90(3H, s), 2.33(2H, m)

EXAMPLE 39

5-Deoxy-5-[4-[3-(2-phenylindol-1-yl)propyl]piperazin-1-yl]-1.4;3.6-dianhydro-L-iditol 2-nitrate hydrochloride (Compound 3)

1-Chloro-3-(2-phenylindol-1-yl)propane was obtained (yield: 60%) in a manner similar to Reference Example 7 except that 2-phenylindole was used in place of 4-methoxythiophenol. Then, Compound 43 was obtained (yield: 57%) in the same manner as in Example 9 except that the period for heating under reflux was changed from 8 hours to 6 hours.

MS (EI) m/z: 492 (M+)
IR (KBr) cm$^{-1}$: 2960(br), 2400(br), 1641, 1275

NMR (DMSO-d$_6$) δ (ppm): 7.4–7.7(7H, m), 7.20(1H, t, J=7.0 Hz), 7.09(1H, t, J=7.0 Hz), 6.55(1H, s), 5.40 (1H, m), 4.96(1H, m), 4.76(1H, m), 4.25(2H, t, J=7.5 Hz), 2.9–4.2(15H, m), 2.07(2H, m)

EXAMPLE 40

5-Deoxy-5-[4-[3-(3-ethoxycarbonylmethylindol-1-yl)propyl]-piperazin-1-yl]-1.4;3.6-dianhydro-L-iditol 2-nitrate hydrochloride (Compound 44)

1-Chloro-3-(3-ethoxycarbonylmethylindol-1-yl)propane was obtained (yield: 47%) in a manner similar to Reference Example 7 except that 3-ethoxycarbonylmethylindole (Reference Example 12) was used in place of 4-methoxythiophenol. Then, Compound 44 was obtained (yield: 36%) in the same manner as in Example 9.

Melting point: 188.0°–188.5° C.
MS (EI) m/z: 502 (M+)
IR (KBr) cm 2980(br), 2410(br), 1729, 1644, 1277
NMR (DMSO-d$_6$) δ (ppm): 7.52(2H, m), 7.34(1H, s), 7.16 (1H, t, J=9.1 Hz), 7.04(1H, t, J=7.7 Hz), 5.41(1H, m), 5.01(1H, m), 4.79(1H, m), 4.26(2H, t, J=7.1 Hz), 4.08(2H, q, J=7.1 Hz), 3.73(2H, s), 3.0–4.4(15H, m), 2.21(2H, m), 1.19(3H, t, J=7.1 Hz)

EXAMPLE 41

5-[4-[3-[4,5-Bis(ethoxycarbonyl)imidazol-1-yl]propyl]-piperazin-1-yl]-5-deoxy-1.4;3.6-dianhydro-L-iditol 2nitrate hydrochloride (Compound 45)

1-Chloro-3-[4,5-bis(ethoxycarbonyl)imidazol-1yl]-propane was obtained (yield: 65%) in a manner similar to Reference Example 7 except that 4,5-bis(ethoxycarbonyl)imidazole (Reference Example 13) was used in place of 4methoxythiophenol. Then, Compound 45 was obtained (yield: in the same manner as in Example 9.

Melting point 196.5°–197.0° C.
Elemental analysis: as C$_{22}$H$_{33}$N$_5$O$_9$·3HCl.
Calcd. (%); C, 42.56 H, 5.84 N, 11.28.
Found (%); C, 42.19 H, 5.93 N, 11.15.
IR (KBr) cm$^{-1}$: 2986, 2400(br), 1717, 1636, 1272
NMR (DMSO-d$_6$) δ (ppm): 8.10(1H, s), 5.43(1H, m), 5.15 (1H, m), 4.84(1H, m), 4.12–4.41(7H, m), 4.07(2H, m), 3.95–4.06(1H, m), 3.24–3.94(9H, m), 3.17(2H, t, J=7.6 Hz), 2.21(2H, m), 1.20–1.35(6H, m)

EXAMPLE 42

5-[4-[3-(4,5-dicarboxyimidazole-1-yl)propyl]piperazin-1-yl]-5-deoxy-1.4;3.6-dianhydro-L-iditol 2-nitrate (Compound 46)

A mixture of 1.32 g (2.58 mmols) of the free form of Compound 45 obtained in Example 41, 0.68 g (17.00 mmols) of sodium hydroxide, 20 ml of water, 20 ml of ethanol and 40 ml of tetrahydrofuran was stirred at room temperature for 10 hours, and then, the pH of the reaction mixture was adjusted with dil. hydrochloric acid to pH 6 –7. The solution was concentrated to less than the half volume and the precipitated crystals were taken out by filtration and dried to afford 0.78 g (yield: 66%) of Compound 46.

Melting point: 202°–205° C.
MS (FAB) m/z: 456 (M+ +1)
IR (KBr) cm$^{-1}$: 3470(br), 3000, 1651, 1627, 1599, 1287
NMR (DMSO-d$_6$) δ (ppm): 9.9(1H, brs), 7.76(1H, s), 5.36 (1H, m), 4.65(2H, m), 4.50(2H, t, J=6.1 Hz), 3.90 4.07(3H, m), 2.25–3.70(12H, m), 2.13(2H, m)

EXAMPLE 43

5-Deoxy-5-[4-[3-(5-ethoxycarbonylbenzimidazol-1-yl)propyl]-piperazin-1-yl]-1.4;3.6-dianhydro-L-iditol 2-nitrate hydrochloride (Compound 47) and
5-deoxy-5-[4-[3-(6-ehoxycarbonylbenzimidazol-1-yl)propyl]piperazin-1-yl]-1.4;3.6-dianhydro-L-iditol 2-nitrate hydrochloride (Compound 48)

5-Ethoxycarbonylbenzimidazole was obtained (yield: 100%) in a manner similar to Reference Example 12 except that benzimidazole-5-carboxylic acid was used in place of indole-3-acetic acid. Then, a mixture of 1-chloro-3-(5-ethoxycarbonylbenzimidazol-1-yl)propane and 1-chloro-3-(6-ethoxycarbonylbenzimidazol-1-yl)propane was obtained (yield: 58%) in the same manner as in Reference Example 7. Thereafter, a mixture of Compound 47 and Compound 48 (about 49 : 51) was obtained (yield: 44%) in the same manner as in Example 9 except that the period for heating under reflux was changed from 8 hours to 5 hours.

Melting point: 219.5°–222.0° C.
Elemental analysis: as C$_{23}$H$_{31}$N$_5$O$_7$·3HCl.
Calcd. (%); C, 46. , 5.72 N, 11.69.
Found (%); C, 46.17 H, 5.84 N, 11.66.
IR (KBr) cm$^{-1}$: 2980, 2370(br), 1712, 1633, 1276
NMR (DMSO-d$_6$) δ (ppm): 9.66 and 9.56(1H, s), 8.60 and 8.40(1H, s), 7.94–8.18(2H, m), 5.42(1H, m), 5.04 (1H, m), 4.79(1H, m), 3.10–4.77(17H, m), 2.41(2H, m), 1.33–1.43(3H, m)

EXAMPLE 44

5-[4-[3-(5-Carboxybenzimidazol-1-yl)propyl]piperazin-1-yl]-5-deoxy-1.4;3.6-dianhydro-L-iditol 2-nitrate (Compound 49) and
5-[4-[3-(6-carboxybenzimidazol-1-yl)propyl]piperazin-1-yl]-5-deoxy-1.4;3.6-dianhydro-L-iditol 2-nitrate (Compound 50)

A mixture of 1.34 g (2.74 mmols) of the free form of the mixture (about 49 :51) of Compound 47 and Compound 48 obtained in Example 43, 0.70 g (17.50 mmols) of sodium hydroxide, 20 ml of water, 20 ml of ethanol and 40 ml of tetrahydrofuran was stirred at room temperature for 9 hours, and then, the pH of the reaction mixture was adjusted with dil. hydrochloric acid to pH 6 –7. The mixture was concentrated under reduced pressure, and the residue was purified by silica gel column chromatography (eluent: chloroform/methanol =3/1) and recrystallized from isopropyl alcohol-water-acetone. The crystals were taken out by filtration and dried to afford 0.65 g (yield: 51%) of t mixture of Compound 49 and Compound 50.

IR (KBr) cm$^{-1}$: 3400(br), 2950, 2822, 1626, 1590, 1275

NMR (DMSO-d$_6$δ ppm): 7.53–8.34(4H, m), 5.36(1H, m), 4.61(2H, m), 4.20–4.38(2H, m), 3.90–4.06(3H, m), 3.58(1H, m), 2.80(1H, m), 2.10–2.42(10H, m), 1.95 (2H, m)

EXAMPLE 45

5-Deoxy-5-[4-[3-(3,4,5-trimethoxyphenoxy)propyl]piperazin-1-yl]-1.4;3.6-dianhydro-L-iditol 2-nitrate hydrochloride (Compound 51)

1-Chloro-3-(3,4,5-trimethoxyphenoxy)propane was obtained (yield: 68%) in a manner similar to Reference Example 7 except that 3,4,5-trimethoxyphenol was used in place of 4-methoxythiophenol. Then, Compound 51 was obtained (yield: 76%) in the same manner as in Example 9 except that the period for heating under reflux was changed from 8 hours to 5 hours.

Melting point: 207.5°–208.0° C.

Elemental analysis: as C$_{22}$H$_{33}$N$_3$O$_9$·2HCl.

Calcd. (%); C, 47.49 H, 6.34 N, 7.55.

Found (%); C, 47.16 H, 6.41 N, 7.51.

IR (KBr) cm$^{-1}$: 2970(br), 2400(br), 1645, 1593, 1276, 1127

NMR (DMSO-d$_6$) δ (ppm): 6.26(2H, s), 5.42(1H, m), 5.04 (1H, m), 4.80(1H, m), 3.76(6H, s), 3.58(3H, s), 3.15–4.60(17H, m), 2.18(2H, m)

EXAMPLE 46

5-Deoxy-5-[4-[3-(3,5-dimethoxyphenoxy)propyl]piperazin-1yl]-1.4;3.6-dianhydro-L-iditol 2-nitrate hydrochloride (Compound 52)

1-Chloro-3-(3,5-dimethoxyphenoxy)propane was obtained (yield: 68%) in a manner similar to Reference Example 7 except that 3,5-dimethoxyphenol was used in place of 4-methoxythiophenol. Then, Compound 52 was obtained (yield: 78%) in the same manner as in Example 9 except that the period for heating under reflux was changed from 8 hours to 5 hours.

Melting point: 198.5°–199.0° C.

MS (EI) m/z: 453 (M$^+$)

IR (KBr) cm$^{-1}$: 2970(br), 2420(br), 1645, 1600, 1276, 1151

NMR (DMSO-d$_6$δ ppm): 6.11(3H, s), 5.42(1H, m), 5.03 (1H, m), 4.80(1H, m), 3.71(6H, s), 3.15–4.60(17H, m), 2.19(2H, m)

EXAMPLE 47

5-Deoxy-5-[4-[3-(3,5-dimethylphenoxy)propyl]piperazin-1-yl]-1.4;3.6-dianhydro-L-iditol 2-nitrate hydrochloride (Compound 53)

1-Chloro-3-(3,5-dimethylphenoxy)propane was obtained (yield, 69%) in a manner similar to Reference Example 7 except that 3,5-dimethylphenol was used in place of 4-methoxythiophenol. Then, Compound 53 was obtained (yield: 68%) in the same manner as in Example 9 except that the period for heating under reflux was changed from 8 hours to 5 hours.

Melting point: 202.0°–202.5° C.

MS (EI) m/z: 421 (M$^+$)

IR (KBr) cm$^{-1}$: 2950(br), 2410(br), 1631, 1274

NMR (DMSO-d$_6$δ ppm): 6.58(1H, s), 6.56(2H, s), 5.42 (1H, m), 5.02(1H, m), 4.80(1H, m), 3.05–4.50(17H, m), 2.23(6H, s), 2.17(2H, m)

EXAMPLE 48

5-Deoxy-5-[4-[3-(3,4,5-trimethoxyphenyl)-trans-2-propenoyl]-piperazin-1-yl]-1.4;3.6-dianhydro-L-iditol 2-nitrate hydrochloride (Compound 54)

A mixture of 1.20 g (5.04 mmols) of trans -3', 4', 5'-trimethoxycinnamic acid, 1.4 ml (10.04 mmols) of triethylamine and 12 ml of a solvent mixture of 2-butanol and acetonitrile (5/1) was stirred at 0° C., and to the solution was dropwise added 1.6 ml of a solution of 0.57 g (5.25 mmols) of ethyl chloroformate in a solvent-mixture of 2-butanol and acetonitrile (5/1). The mixture was stirred at room temperature for further 15 minutes. Then, 6 ml of a solution of 1.30 g (5.01 mmols) of Compound b in a solvent mixture of 2-butanol and acetonitrile (5/1) was dropwise added to the reaction mixture followed by stirring the solution at room temperature for 50 minutes. The mixture was concentrated under reduced pressure, and the residue was purified by silica gel column chromatography (eluent: chloroform/methanol =3/1). The product was dissolved in chloroform and to the solution was added ethyl acetate saturated with hydrogen chloride. The mixture was poured into cold diethyl ether and the precipitated crystals were taken out by filtration and dried to afford 1.19 g (yield: 46%) of Compound 54.

Melting point: 161°–168° C.

MS (FAB) m/z: 480 (M$^+$1)

IR (KBr) cm$^{-1}$: 2940(br), 2432(br), 1640, 1600, 1276, 1122

NMR (DMSO-d$_6$) δ (ppm): 7.51(1H, d, J=15.3 Hz), 7.21(1H, d, J=15.3 Hz), 7.07(2H, s), 5.44(1H, m), 5.33(1H, m), 4.87(1H, m), 3.83(6H, s), 3.69(3H, s), 2.95 4.75(13H, m)

EXAMPLE 49

5-Deoxy-5-[4-(2-nitrophenyl)piperazin-1-yl]-1.4;3.6-dianhydro-L-iditol (Compound 100)

A mixture of 5.0 g (23.3 mmols) of Compound a obtained in Reference Example 1, 23.7 g (117.3 mmols) of 2-bromonitrobenzene, 6.5 g (47.0 mmols) of potassium carbonate, 1.6 g (25.2 mmols) of copper powders and 50 ml of methyl ethyl ketone was heated under reflux for 16 hours. The mixture was concentrated under reduced pressure, water and chloroform were added to the residue, and the mixture was filtered. The chloroform layer in the filtrate was dried over anhydrous sodium sulfate. The solvent was evaporated under reduced pressure, and the residue was purified by silica gel column chromatography (eluent: chloroform/methanol =25/1) to afford 7.8 g (quantitative) of Compound 100.

NMR (CDCl$_3$δ ppm): 6.9–7.8(4H, m), 4.72(1H, m), 4.38 (1H, m), 4.27(1H, m), 3.51–4.15(4H, m), 2.4–3.2 (9H, m)

EXAMPLE 50

5-Deoxy-5-[4-(2,4-dinitrophenyl)piperazin-1-yl]-1.4;3.6-dianhydro-L-iditol 2-nitrate hydrochloride (Compound 55) and 5-deoxy-5-[4-(2,6-dinitrophenyl)piperazin-1-yl]-1.4;3.6-dianhydro-L-iditol 2-nitrate hydrochloride (Compound 56)

2.44 ml of fumed nitric acid was cooled to 0° C., and 4.8 ml of acetonitrile and 4.8 ml of acetic anhydride were added thereto. Furthermore, 15.5 ml of a solution of 3.97 g (11.8 mmols) of Compound 55 obtained in Example 49 in acetonitrile was dropwise added to the mixture over 15 minutes. The mixture was stirred at 0° C. for further 20 minutes. An aqueous saturated sodium bicarbonate solution was added to the mixture to neutralize the mixture followed by extraction of the solution with chloroform. The chloroform layer was dried over anhydrous sodium sulfate. The solvent was evaporated under reduced pressure, and the residue was purified by silica gel column chromatography (eluent: chloroform). The product obtained from the first fraction was dissolved in chloroform, and to the solution was added ethyl acetate saturated with hydrogen chloride. The mixture was poured into cold diethyl ether and the precipitated crystals were taken out by filtration and dried to afford 0.36 g (yield: 6%) of Compound 56.

Then, 2.25 g (yield: 38%) of Compound 55 was obtained from the second fraction in a similar manner.

Compound 55
Melting point: 84°–88° C.
MS (EI) m/z: 425 (M+)
IR (KBr) cm$^{-1}$: 2940(br), 2400(br), 1639, 1605, 1527, 1338, 1276
NMR (DMSO-d$_6$) δ (ppm): 8.70(1H, s), 8.36(1H, d, J=9.5 Hz), 7.54(1H, d, J=9.5 Hz), 5.44(1H, m), 5.29 (1H, m), 4.85(1H, m), 2.9–4.3(13H, m)

Compound 56
Melting point: 204.5°–205.0° C.
MS (EI) m/z: 425 (M+)
IR (KBr) cm$^{-1}$: 2864(br), 2180(br), 1641, 1533, 1344, 1273
NMR (DMSO-d δ ppm): 8.21(2H, d, J=8.1 Hz), 7.62(1H, t, J=8.1 Hz), 5.43(1H, m), 5.25(1H, m), 4.81(1H, m), 4.16–4.30(1H, m), 3.87–4.16(3H, m), 2.80–3.85 (9H, m)

EXAMPLE 51

5-[4-[2-(Benzimidazol-2-yl)ethyl]piperazin-1-yl]-5-deoxy-1.4;3.6-dianhydro-L-iditol 2-nitrate hydrochloride (Compound 57)

A mixture of 2.61 g (10.07 mmols) of Compound b, 2.54 g (7.98 mmols) of 1-methanesulfonyl-2-(2-methanesulfonyloxyethyl)benzimidazole (Reference Example 14), 30 ml (21.51 mmols) of triethylamine and 60 ml of n-butanol was heated under reflux for 2 hours and a half. The mixture was concentrated under reduced pressure, and the residue was purified by silica gel column chromatography (eluent: chloroform/methanol =20/1). The product was dissolved in chloroform, and to the solution was added ethyl acetate saturated with hydrogen chloride. The mixture was poured into cold diethyl ether and the precipitated crystals were taken out by filtration and dried to afford 0.98 g (yield: 24%) of Compound 57.

Melting point: 77°–79° C.
IR (KBr) cm$^{-1}$: 2970(br), 2570(br), 1640, 1273
NMR (DMSO-d$_6$) 6 (ppm): 7.81(2H, m), 7.55(2H, m), 5.42 (1H, m), 5.10(1H, m), 4.81(1H, m), 3.0–4.8(17H, m)

EXAMPLE 52

5-[4-(Benzothiazol-2-yl)piperazin-1-yl]-5-deoxy-1.4;3.6-dianhydro-L-iditol 2-nitrate hydrochloride (Compound 58)

A mixture of 0.90 g (3.47 mmols) of Compound b, 0.57 g (3.36 mmols) of 2-chlorobenzothiazole, 0.52 g (3.76 mmols) of potassium carbonate and 25 ml of n-butanol was heated under reflux for 7 hours. The mixture was concentrated under reduced pressure, and the residue was purified by silica gel column chromatography (eluent: chloroform/methanol =50/1). The product was converted into the salt in a manner similar to Example 51 to afford 0.29 g (yield: 18%) of Compound 58.

Melting point: 225.0°–229.5° C.
MS (EI) m/z: 392 (M+)
IR (KBr) cm$^{-1}$: 2975(br), 2422(br), 1636, 1277
NMR (DMSO-d δ ppm): 7.85(1H, d, J=7.5 Hz), 7.55(1H, d, J=7.5 Hz), 7.34(1H, dd, J=9.0, 7.5 Hz), 7.16(1H, dd, J=9.0, 7.5 Hz), 5.45(1H, m), 5.34(1H, m), 4.87 (1H, m), 3.1–4.9(13H, m)

EXAMPLE 53

5-[4-(Benzoxazol-2-yl)piperazin-1-yl]-5-deoxy-1.4;3.6-dianhydro-L-iditol 2-nitrate hydrochloride (Compound 59)

Compound 59 was obtained (yield: 28%) in a manner similar to Example 52 except that 2-chlorobenzoxazole was used in place of 2-chlorobenzothiazole and the period for heating under reflux was changed from 7 hours to an hour and a half.

Melting point: 232.3°–232.9° C.
MS (EI) m/z: 376 (M+).
IR (KBr) cm$^{-1}$: 3024, 2360(br), 1733, 1640, 1280
NMR (DMSO-d$_6$) δ (ppm): 7.47 (1H, d, J=7.8 Hz), 7.37(1H, d, J=7.8 Hz), 7.21(1H, dd, J=9.0, 7.8 Hz), 7.10(1H, dd, J=9.0, 7.8 Hz), 5.44(1H, m), 5.34(1H, m), 4.87 (1H, m), 3.2–4.9(13H, m)

EXAMPLE 54

5-Deoxy-5-[4-(1-phenyl-1H-tetrazol-5-yl)piperazin-1-yl-]-1.4;3.6-dianhydro-L-iditol 2-nitrate hydrochloride (Compound 60)

A mixture of 1.20 g (4.64 mmols) of Compound b, 0.84 g (4.65 mmols) of 5-chloro-1-phenyl-1H-tetrazole, 0.64 ml (4.64 mmols) of triethylamine and 20 ml of methyl ethyl ketone was heated under reflux for 10 hours. The mixture was concentrated under reduced pressure, and an aqueous saturated sodium bicarbonate was added to the residue. Extraction was performed with chloroform, and the extract was dried over anhydrous sodium sulfate. The solvent was evaporated under reduced pressure. The residue was purified by silica gel column chromatography (eluent: chloroform/methanol =40/1). The product was converted into the salt in a manner similar to Example 51 to afford 1.20 g (yield: 51%) of Compound 60.

Melting point: 136.5°–137.0° C.
MS (EI) m/z: 403 (M+)
NMR (DMSO-d δ ppm): 7.55–7.80(5H, m), 5.42(1H, m), 5.22(1H, m), 4.82(1H, m), 3.97–4.26(4H, m), 2.9 4.0(9H, m)

EXAMPLE 55

5-Deoxy-5-[4-[2-(3,5-dimethoxyphenoxy)ethyl]piperazin-1-yl]-1.4;3.6-dianhydro-L-iditol 2-nitrate hydrochloride (Compound 61)

1-Chloro-2-(3,5-dimethoxyphenoxy)ethane was obtained (yield: 5%) in a manner similar to Reference Example 7 except that 3,5-dimethoxyphenol and 1-bromo-2-chloroethane were used in place of 4-methoxythiophenol and 1-bromo-3-chloropropane, respectively. Then, Compound 61 was obtained (yield: 52%) in the same manner as in Example 9 except that the period for heating under reflux was changed from 8 hours to 15 hours.

Melting point: 207.0° C.
Elemental analysis: as $C_{20}H_{29}N_3O_8 \cdot 2HCl$.
Calcd. (%); C, 46.88 H, 6.10 N, 8.20.
Found (%); C, 46.65 H, 6.15 N, 7.95.
IR (KBr) cm$^{-1}$: 2960(br), 2340(br), 1634, 1605, 1276
NMR (DMSO-d) δ (ppm): 6.19(2H, s), 6.16(1H, s), 5.42 (1H, m), 5.05(1H, m), 4.80(1H, m), 4.39(2H, m), 4.09–4.21(1H, m), 4.02–4.10(2H, m), 3.87–4.01(1H, m), 3.72(6H, s), 3.00–3.85(11H, m)

EXAMPLE 56

5-[4-[2-(Benzimidazol-1-yl)ethyl]piperazin-1-yl]-5-deoxy-1.4;3.6-dianhydro-L-iditol 2-nitrate hydrochloride (Compound 62)

5 1-(Benzimidazol-1-yl)-2-chloroethane was obtained (yield: 24%) in a manner similar to Reference Example 7 except that benzimidazole and 1-bromo-2-chloroethane were used in place of 4-methoxythiophenol and 1-bromo-3-chloropropane, respectively. Then, Compound 62 was obtained (yield: 47%) in the same manner as in Example 9 except that the period for heating under reflux was changed from 8 hours to 18 hours.

Melting point: 204°–205° C.
MS (EI) m/z: 403 (M+)
IR (KBr) cm 2975(br), 2375(br), 1637, 1450, 1274
NMR (DMSO-d$_6$) δ (ppm): 9.85(1H, s), 8.14(1H, m), 7.91 (1H, m), 7.58–7.72(2H, m), 5.42(1H, m), 5.17(1H, m), 4.91(2H, m), 4.82(1H, m), 2.9–4.8(15H, m)

EXAMPLE 57

5-Deoxy-5-[4-[2-(3,4,5-trimethoxyphenoxy)ethyl]piperazin-1-yl]-1.4;3.6-dianhydro-L-iditol 2-nitrate hydrochloride (Compound 63)

1-Chloro-2-(3,4,5-trimethoxyphenoxy)ethane was obtained (yield: 11%) in a manner similar to Reference Example 7 except that 3,4,5-trimethoxyphenol and 1-bromo-2-chloroethane were used in place of 4-methoxythiophenol and 1-bromo-3-chloropropane, respectively. Then, Compound 63 was obtained (yield: 36%) in the same manner as in Example 9.

Melting point: 199°–200° C.
MS (EI) m/z: 469 (M+)
IR (KBr) cm$^{-1}$: 2980(br), 2190(br), 1632, 1598, 1506
NMR (DMSO-d$_6$) δ (ppm): 6.35(2H, s), 5.43(1H, m), 5.05 (1H, m), 4.80(1H, m), 4.40(2H, m), 4.10–4.21(1H, s), 3.59(3H, s), 3.1–3.9(11H, m)

EXAMPLE 58

5-Deoxy-5-[4-(2-methoxyphenyl)piperazin-1-yl]-1.4;3.6-dianhydro-L-iditol 2-nitrate hydrochloride (Compound 64)

A mixture of 1.90 g (10.00 mmols) of 5-amino-5-deoxy-1.4;3.6-dianhydro-L-iditol 2-nitrate as described in Japanese Published Unexamined Patent Application No. 58692/82 [U.S. Pat. No.4542137 and EP-B No. 44927], 4.47 g (18.01 mmols) of o-[N,N-bis(chloroethyl)amino]anisole (Reference Example 15), 2.8 ml (20.08 mmols) of triethylamine, 8.00 g (53.37 mmols) of sodium iodide and 50 ml of methyl ethyl ketone was heated under reflux for 38 hours. The mixture was concentrated under reduced pressure, and the residue was purified by silica gel column chromatography (eluent: chloroform). The product was converted into the salt in a manner similar to Example 51 to afford 1.75 g (yield: 40%) of Compound 64.

Melting point: 202.1°–207.3° C.
MS (EI) m/z: 365 (M+)
IR (KBr) cm$^{-1}$: 2980(br), 2350(br), 1643, 1456, 1277
NMR (DMSO-d$_6$ δ ppm): 6.87–7.10(4H, m), 5.45(1H, m), 5.35(1H, m), 4.86(1H, m), 3.80(3H, s), 2.90–4.65 (13H, m)

EXAMPLE 59

5-[4-[4-Cyano-5-methyl-4-(3,4,5-trimethoxyphenyl)hexyl]-piperazin-1-yl]-5-deoxy-1.4;3.6-dianhydro-L-iditol 2-nitrate hydrochloride (Compound 65)

Compound 65 was obtained (yield: 50%) in a manner similar to Example 9 except that 4-cyano-5-methyl-4-(3,4,5-trimethoxyphenyl)hexyl chloride (Reference Example 16) was used in place of 1-chloro-3-(4-methoxyphenylthio)propane and the period for heating under reflux was changed from 8 hours to 17 hours.

Melting point: 112° C.
MS (EI) m/z: 548 (M+)
IR (KBr) cm$^{-1}$: 2960(br), 2430(br), 1644, 1590, 1277, 1125
NMR (DMSO-d$_6$) δ (ppm): 6.68(2H, s), 5.41(1H, m), 4.98 (1H, m), 4.77(1H, m), 3.82(6H, s), 3.68(3H, s), 2.95–4.70(15H, m), 2.05–2.35(3H, m), 1.63(1H, m), 1.36(1H, m), 1.12(3H, d, J=6.6 Hz), 0.72(3H, d, J=6.6 Hz)

EXAMPLE 60

5-Deoxy-5-[4-(7-methyl-s-triazolo[1,5-a]pyrimidin-5-yl)-piperazin-1-yl]-1.4;3.6-dianhydro-L-iditol 2-nitrate hydrochloride (Compound 66)

Compound 66 was obtained (yield: 49%) in a manner similar to Example 5 except that 5-chloro-7-methyl-s-triazolo[1,5-a]pyrimidine [Monat. Chem., 118, 601 (1987)], was used in place of 7-chloro-5-methyl-s-triazolo[1,5-a]pyrimidine and the stirring time was changed from 40 minutes to 7 hours.

Melting point: 228.0°–230.0° C.
MS (FAB) m/z: 392 (M++I)
IR (KBr) cm$^{-1}$: 2522(br), 1673, 1638, 1538, 1277
NMR (DMSO-d δ ppm): 8.80(1H, s), 7.27(1H, s), 5.45 (1H, m), 5.34(1H, m), 4.88(1H, m), 3.1–5.6(13H, m), 2.66(3H, s)

EXAMPLE 61

5-Deoxy-5-[4-[3-(7-hydroxy-4,6-dimethylbenzimidazol-1-yl)propyl]piperazin-1-yl]-1.4;3.6-dianhydro-L-iditol 2-nitrate hydrochloride (Compound 67) and
5-deoxy-5-[4-[3-(4-hydroxy-5,7-dimethylbenzimidazol-1-yl)propyl]piperazin-1-yl]-1.4;3.6-dianhydro-L-iditol 2-nitrate hydrochloride (Compound 68)

A mixture of Compound 67 and Compound 68 (about 1 :1) was obtained (yield: 63%) in a manner similar to Example 9 except that a mixture of 1-(3-chloropropyl)-7-hydroxy-4,6-dimethylbenzimidazole and 1-(3-chloropropyl)-4-hydroxy-5,7-dimethylbenzimidazole (Reference Example 17) was used in place of 1-chloro-3-(4-methoxyphenylthio)propane and the period for heating under reflux was changed from 8 hours to 15 hours.

Melting point: 206°–209° C.
MS (FAB) m/z: 462 (M++1)
IR (KBr) cm$^{-1}$: 2980(br), 2570(br), 1638, 1275
NMR (DMSO-d$_6$ δ ppm): 9.67 and 9.57(1H, s), 7.51 and 7.33(1H, s), 7.12 and 7.10(1H, s), 5.39(1H, m), 4.81(1H, m), 4.61–4.78(3H, m), 2.63 and 2.47(3H, s), 2.33 and 2.29(3H, s), 2.1–4.4(17H, m)

EXAMPLE 62

5-Deoxy-5-[4-(quinolin-2-yl)piperazin-1-yl]-1.4;3.6-dianhydro-L-iditol 2-nitrate hydrochloride (Compound 69)

Compound 69 was obtained (yield: 17%) in a manner similar to Example 54 except that 2-chloroquinoline was used in place of 5-chloro-1-phenyl-1H-tetrazole and the period for heating under reflux was changed from 10 hours to 20 hours.

Melting point: 219° C.
Elemental analysis: as $C_{19}H_{22}N_4O_5 \cdot 2.6HCl$.
Calcd. (%); C, 47.42 H, 5.15 N, 11.64.
Found (%); C, 47.40 H, 5.21 N, 11.74.
IR (KBr) cm$^{-1}$: 2960(br), 2360(br), 1644, 1276
NMR (DMSO-d$_6$) δ (ppm): 8.47(1H, d, J=9.6 Hz), 8.29(1H, d, J=7.3 Hz), 7.94(1H, d, J=7.3 Hz), 7.79(1H, t, J=7.3 Hz), 7.59(1H, d, J=9.6 Hz), 7.51(1H, t, J=7.3 Hz), 5.45(1H, m), 5.33(1H, m), 4.89(1H, m), 2.8–5.0(13H, m)

EXAMPLE 63

5-Deoxy-5-[4-(2-phenoxyethyl)piperazin-1-yl]-1.4;3.6-dianhydro-L-iditol 2-nitrate hydrochloride (Compound 70)

1-Chloro-2-phenoxyethane was obtained (yield: 10%) in a manner similar to Reference Example 7 except that phenol and 1-bromo-2-chloroethane were used in place of 4-methoxythiophenol and 1-bromo-3-chloropropane. Then, Compound 70 was obtained (yield: 48%) in the same manner as in Example 9.

Melting point: 198.0°–199.5° C.
Elemental analysis: as $C_{18}H_{25}N_3O_6 \cdot 2HCl$.
Calcd. (%); C, 47.80 H, 6.02 N, 9.29.
Found (%); C, 47.67 H, 6.13 N, 9.23.
IR (KBr) cm$^{-1}$: 2950(br), 2240(br), 1634, 1597, 1274
NMR (DMSO-d$_6$) δ (ppm): 7.33(2H, m), 6.95–7.08(3H, m), 5.42(1H, m), 5.07(1H, m), 4.81(1H, m), 4.42(2H, m), 4.09–4.20(1H, m), 4.01–4.10(2H, m), 3.88–4.01 (1H, m), 2.9–3.9(11H, m)

EXAMPLE 64

5-Deoxy-5-[4-(pyrimidin-2-yl)piperazin-1-yl]-1.4;3.6-dianhydro-L-iditol 2-nitrate hydrochloride (Compound 71)

Compound 71 was obtained (yield: 41%) in a manner similar to Example 54 except that 2-chloropyrimidine was used in place of 5-chloro-1-phenyl-1H-tetrazole.

Melting point: 186°–188° C.
MS (EI) m/z: 337 (M+)
IR (KBr) cm$^{-1}$: 3572, 3418, 2675(br), 2375(br), 1637 (br), 1282
NMR (DMSO-d$_6$) δ (ppm): 8.46(2H, d, J=4.9 Hz), 6.78(1H, t, J=4.9 Hz), 5.44(1H, m), 5.34(1H, m), 4.86(1H, m), 2.9–5.8(13H, m)

EXAMPLE 65

5-Deoxy-5-[4-(4-phenylthiobutyl)piperazin-1-yl]-1.4;3.6-dianhydro-L-iditol 2-nitrate hydrochloride (Compound 72)

1-Chloro-4-phenylthiobutane was obtained (yield: 87%) in a manner similar to Reference Example 7 except that thiophenol and 1-bromo-4-chlorobutane were used in place of 4-methoxythiophenol and 1-bromo-3-chloropropane, respectively. Then, Compound 72 was obtained (yield: 64%) in the same manner as in Example 9.

Melting point: 195.5°–197.5° C.
Elemental analysis: as $C_{20}H_{29}N_3O_5S \cdot 2HCl$.
Calcd. (%); C, 48.39 H, 6.29 N, 8.46.
Found (%); C, 48.29 H, 6.36 N, 8.23.
IR (KBr) cm$^{-1}$: 2960(br), 2400(br), 1648, 1278
NMR (DMSO-d$_6$) δ (ppm): 7.25–7.41(4H, m), 7.19(1H, m), 5.42(1H, m), 5.05(1H, m), 4.80(1H, m), 4.09–4.21 (1H, m), 4.01–4.09(2H, m), 3.86–3.99(1H, m), 3.14 (2H, t, J=7.9 Hz), 3.05–3.80(9H, m), 3.00(2H, t, J=7.2 Hz), 1.84(2H, m), 1.61(2H, m)

EXAMPLE 66

5-Deoxy-5-[4-(3-phenylthiopropyl)piperazin-1-yl]-1.4;3.6-dianhydro-D-mannitol 2-nitrate hydrochloride (Compound 95)

A mixture of 1.51 g (7.94 mmols) of 5-amino-5-deoxy-1.4;3.6-dianhydro-D-mannitol 2-nitrate (Japanese Published Unexamined Patent Application No. 58692/82 [U.S. Pat. No. 4,542,137 and EP-B No. 44927]), 2.84 g (9.72 mmols) of 1-bis(chloroethyl)amino-3-phenylthiopropane (Reference Example 18), 3.0 ml (21.5 mmols) of triethylamine, 13.0 g (86.7 mmols) of sodium iodide and 50 ml of methyl ethyl ketone was heated under reflux for 10 hours. The mixture was concentrated under reduced pressure, and the residue was purified by silica gel column chromatography (eluent: chloroform/methanol =50/1). The product was converted into the salt basically according to the method of Example 51 to afford 1.00 g (yield: 26%) of Compound 95.

Melting point: 197°–199° C.
MS (EI) m/z: 409 (M+)
IR (KBr) cm$^{-1}$: 2980(br), 2475(br), 1651, 1292
NMR (DMSO-d$_6$) δ (ppm): 7.25–7.45(4H, m), 7.16–7.27(1H, m), 5.55(1H, m), 4.99(1H, m), 4.67(1H, m), 3.06 (2H, t, J=7.2 Hz), 2.7–4.6(15H, m), 2.03(2H, m)

EXAMPLE 67

2-Deoxy-2-[4-(3-phenylthiopropyl)piperazin-1-yl]-1.4;3.6-dianhydro-D-glucitol 5-nitrate hydrochloride (Compound 96)

Compound 96 was obtained (yield: 71%) in a manner similar to Example 9 except that Compound c obtained in Reference Example 3 and 1-chloro-3-phenylthiopropane (Reference Example 6) were used in place of Compound b and 1-chloro-3-(4-methoxyphenylthio)propane, respectively.

Melting point: 198.5°–201.0° C.
MS (EI) m/z: 409 (M+)
IR (KBr) cm$^{-1}$: 2960(br), 2440(br), 1649, 1280
NMR (DMSO-d$_6$) δ (ppm): 7.26–7.44(4H, m), 7.17–7.27(1H, m), 5.56(1H, m), 5.00(1H, dd, J=5.3, 5.3 Hz), 4.67 (1H, m), 3.06(2H, t, J=7.2 Hz), 3.0–4.4(15H, m), 2.03(2H, m)

EXAMPLE 68

5-Deoxy-5-[4-(3-phenylthiopropyl)piperazin-1-yl]-1.4;3.6-dianhydro-D-glucitol 2-nitrate hydrochloride (Compound 97)

Compound 97 was obtained (yield: 80%) in a manner similar to Example 9 except that Compound d obtained in Reference Example 4 and 1-chloro-3-phenylthiopropane (Reference Example 6) were used in place of Compound b and 1-chloro-3-(4-methoxyphenylthio)propane, respectively.

Melting point: 204.5°–205.5° C.

MS (EI) m/z: 409 (M+)

IR (KBr) cm$^{-1}$: 2990(br), 2350(br), 1656, 1275

NMR (DMSO-d$_6$) δ (ppm): 7.28–7.45(4H, m), 7.18–7.27(1H, m), 5.48(1H, m), 4.80–4.83(2H, m), 4.17–4.34(2H, m), 4.03–4.12(1H, m), 3.23(2H, t, J=7.9 Hz), 3.06 (2H, t, J=7.2 Hz), 2.9–4.2(10H, m), 2.03(2H, m)

EXAMPLE 69

5-[4-[3-(Benzimidazol-1-yl)propyl]piperazin-1-yl]-5-deoxy-1.4;3.6-dianhydro-D-glucitol 2-nitrate hydrochloride hydrate (Compound 98)

Compound 98 was obtained (yield: 39%) in a manner similar to Example 22 except that Compound d obtained in Reference Example 4 was used in place of Compound b.

Elemental analysis: as C$_{20}$H$_{27}$N$_5$O$_5$·2.7HCl·3.7H$_2$O.

Calcd. (%); C, 41.23 H, 6.42 N, 12.02.

Found (%); C, 41.23 H, 6.32 N, 11.92.

IR (KBr) cm$^{-1}$: 2970(br), 2460(br), 1638, 1275

NMR (DMSO-d$_6$) δ (ppm): 9.80(1H, s), 8.14(1H, m), 7.91 (1H, m), 7.59–7.72(2H, m), 5.49(1H, m), 4.90(1H, m), 4.68(1H, m), 2.8–4.5(17H, m), 2.43(2H, m)

EXAMPLE 70

5-Deoxy-5-[4-(3-phenylthiopropyl)homopiperazin-1-yl]-1.4;3.6-dianhydro-L-iditol 2-nitrate hydrochloride (Compound 99)

Compound 99 was obtained (yield: 53%) in a manner similar to Example 9 except that Compound e obtained in Reference Example 5 and 1-chloro-3-phenylthiopropane (Reference Example 6) were used in place of Compound b and 1-chloro-3-(4-methoxyphenylthio)propane, respectively.

MS (EI) m/z: 423 (M+)

IR (KBr) cm$^{-1}$: 2940, 2580(br), 1636, 1276

NMR (DMSO-d$_6$) δ (ppm): 7.28–7.46(4H, m), 7.17–7.28(1H, m), 5.44(1H, m), 5.20(1H, m), 4.85(1H, m), 3.1 4.3(15H, m), 3.05(2H, t, J=7.2 Hz), 2.22(2H, m), 1.99(2H, m)

EXAMPLE 71

5-Deoxy-5-[4-(3-phenylthiopropyl)piperazin-1-yl]-1.4;3.6-dianhydro-L-iditol hydrochloride (Compound 101)

Compound 101 was obtained (yield: 27%) in a manner similar to Example 1 except that Compound a obtained in Reference Example 1 was used in place of Compound b.

MS (FAB) m/z: 365 (M+ +1)

IR (KBr) cm$^{-1}$: 3410(br), 2975, 2420(br), 1442, 1073

NMR (DMSO-d$_6$) δ (ppm): 11.71(1H, br), 7.29–7.45(4H, m), 7.17–7.27(1H, m), 4.99(1H, m), 4.36(1H, m), 3.99 4.13(2H, m), 3.87(1H, m), 3.15–3.82(13H, m), 3.06 (2H, t, J=7.2 Hz), 2.01(2H, m)

EXAMPLE 72

5-Deoxy-5-[4-(3-phenoxypropyl)piperazin-1-yl]-1.4;3.6-dianhydro-L-iditol hydrochloride (Compound 102)

Compound 102 was obtained (yield: 65%) in a manner similar to Example 20 except that Compound a obtained in Reference Example 1 was used in place of Compound b.

Melting point: 235.0°–235.5° C

Elemental analysis: as C$_{19}$H$_{28}$N$_2$O$_4$·2HCl.

Calcd. (%); C, 54.16 H, 7.18 N, 6.65.

Found (%); C, 54.12 H, 7.14 N, 6.80.

IR (KBr) cm$^{-1}$: 3430(br), 2976(br), 2440(br), 1601, 1496, 1250, 1071

NMR (DMSO-d$_6$) δ (ppm): 11.40(1H, br), 7.30(2H, t, J=8.1 Hz), 6.87–7.03(3H, m), 5.01(1H, m), 4.37(1H, m), 3.98–4.16(2H, m), 3.89(1H, m), 3.05–4.85(15H, m), 2.20(2H, m)

EXAMPLE 73

5-[4-(Benzoxazol-2-yl)piperazin-1-yl]-5-deoxy-1.4;3.6-dianhydro-L-iditol hydrochloride (Compound 103)

Compound 103 was obtained (yield: 80%) in a manner similar to Example 53 except that Compound a obtained in Reference Example 1 was used in place of Compound b.

Melting point: 224.2°–225.8° C.

MS (EI) m/z: 331 (M+)

IR (KBr) cm$^{-1}$: 3350(br), 2420(br), 1695, 1682, 1634, 1086

NMR (DMSO-d$_6$) δ (ppm): 12.50(1H, br), 7.47(1H, d, J=7.6 Hz), 7.37(1H, d, J=7.2 Hz), 7.21(1H, dd, J=7.6, 7.2 Hz), 7.09(1H, dd, J=7.6, 7.2 Hz), 5.20(1H, m), 3.0–4.8(15H, m)

EXAMPLE 74

5-Deoxy-5-[4-(1-phenyl-1H-tetrazol-5-yl)piperazin-1-yl]-1.4;3.6-dianhydro-L-iditol hydrochloride (Compound 104)

Compound 104 was obtained (yield: 58%) in a manner similar to Example 54 except that Compound a obtained in Reference Example 1 was used in place of Compound b.

MS (EI) m/z: 358 (M+)

IR (KBr) cm$^{-1}$: 3400(br), 2938(br), 2580(br), 1558, 1071

NMR (DMSO-d$_6$) δ (ppm): 12.37(1H, br), 7.50–7.81(5H, m), 5.13(1H, m), 4.36(1H, m), 3.0–4.6(14H, m)

EXAMPLE 75

5-Deoxy-5-[4-[3-(3,4,5-trimethoxyphenoxy)propyl]piperazin-1-yl]-1.4;3.6-dianhydro-L-iditol hydrochloride (Compound 105)

Compound 105 was obtained (yield: 51%) in a manner similar to Example 45 except that Compound a obtained in Reference Example 1 was used in place of Compound b.

Melting point: 227°–228° C.

MS (EI) m/z: 438 (M+)

IR (KBr) cm$^{-1}$: 3430(br), 2960(br), 2440(br), 1592, 1504, 1228, 1121

NMR (DMSO-d$_6$) δ (ppm): 11.81(1H, br), 6.26(2H, s), 4.99(1H, m), 4.37(1H, m), 3.97–4.16(4H, m), 3.76 (6H, s), 3.58(3H, s), 3.00–3.95(14H, m), 2.17(2H, m)

EXAMPLE 76

5-Deoxy-5-[4-[3-(3,5-dimethoxyphenoxy)propyl]piperazin-1-yl]-1.4;3.6-dianhydro-L-iditol hydrochloride (Compound 106)

Compound 106 was obtained (yield: 74%) in a manner similar to Example 46 except that Compound a obtained in Reference Example 1 was used in place of Compound b.

Melting point: 222°–225° C.

Elemental analysis: as C$_{21}$H$_{32}$N$_2$O$_7$·2HCl.

Calcd. (%); C, 52.39 H, 7.12 N, 5.82.
Found (%); C, 52.21 H, 7.21 N, 6.00.
IR (KBr) cm$^{-1}$: 3434(br), 2950(br), 2440(br), 1604, 1208, 1155, 1071
NMR (DMSO-d$_6$) δ (ppm): 11.83(1H, br), 6.11(3H, s), 5.00(1H, m), 4.37(1H, m), 3.97–4.19(4H, m), 3.71 (6H, s), 3.05–3.95(14H, m), 2.17(2H, m)

EXAMPLE 77

5-[4-[4-Cyano-4-(3,4,5-trimethoxyphenyl)-5-methylhexyl]-piperazin-1-yl]-5-deoxy-1.4;3.6-dianhydro-L-iditol hydrochloride (Compound 107)

Compound 107 was obtained (yield: 98%) in a manner similar to Example 59 except that Compound a obtained in Reference Example 1 was used in place of Compound b.
Melting point: 85°–88° C.
MS (EI) m/z: 503 (M$^+$)
IR (KBr) cm$^{-1}$: 3400(br), 2960(br), 2410(br), 1590, 1512, 1252, 1121
NMR (DMSO-d$_6$) δ (ppm): 11.31(1H, br), 6.68(2H, s), 4.95(1H, m), 4.33(1H, m), 3.82(6H, s), 3.68(3H, s), 2.85–4.70(16H, m), 2.02–2.33(3H, m), 1.63(1H, m), 1.35(1H, m), 1.12(3H, d, J=6.5 Hz), 0.72(3H, d, J=6.5 Hz)

EXAMPLE 78

5-Deoxy-5-[4-(2-phenoxyethyl)piperazin-1-yl]-1.4;3.6-dianhydro-L-iditol hydrochloride (Compound 108)

Compound 108 was obtained (yield: 48%) in a manner similar to Example 63 except that Compound a obtained in Reference Example 1 was used in place of Compound b.
Melting point: 199.0°–199.5° C.
MS (EI) m/z: 334 (M$^+$)
IR (KBr) cm$^{-1}$: 3288(br), 2954(br), 2570(br), 1598, 1494, 1455, 1245, 1087
NMR (DMSO-d$_6$) δ (ppm): 11.92(1H, br), 7.20–7.43(2H, m), 6.88–7.11(3H, m), 5.01(1H, m), 4.30–4.50(3H, m), 3.0–4 8(16H, m)

EXAMPLE 79

5-Deoxy-5-[4-[3-(3,5-dimethylphenoxy)propyl]piperazin-1-yl]1.4;3.6-dianhydro-L-iditol hydrochloride (Compound 109)

Compound 109 was obtained (yield: 80%) in a manner similar to Example 47 except that Compound a obtained in Reference Example 1 was used in place of Compound b.
Melting point: 242° C.
Elemental analysis: as C$_{21}$H$_{32}$N$_2$O$_4$·2HCl.
Calcd. (%); C, 56.12 H, 7.63 N, 6.23.
Found (%); C, 56.12 H, 7.81 N, 6.05.
IR (KBr) cm$^{-1}$: 3434(br), 2950(br), 2450(br), 1595, 1323, 1298, 1169, 1070
NMR (DMSO-d$_6$) δ (ppm): 11.81(1H, br), 6.58(1H, s), 6.56(2H, s), 5.00(1H, m), 4.37(1H, m), 3.94–4.12 (4H, m), 3.81–3.94(1H, m), 3.0–3.9(13H, m), 2.23 (6H, s), 2.17(2H, m)

EXAMPLE 80

5-Deoxy-5-[4-(2-methoxyphenyl)piperazin-1-yl]-1.4;3.6-dianhydro-L-iditol hydrochloride (Compound 110)

Compound 110 was obtained (yield: 5%) in a manner similar to Example 58 except that Compound a obtained in Reference Example 1 was used in place of Compound b.
Melting point: 209.0°–210.5° C.
MS (EI) m/z: 320 (M$^+$)
IR (KBr) cm$^{-1}$: 3416(br), 2994(br), 2370(br), 1607, 1457, 1265, 1063
NMR (DMSO-d$_6$) δ (ppm): 12.18(1H, br), 6.87–7.08(4H, m), 5.21(1H, m), 4.40(1H, m), 3.95–4.20(3H, m), 3.80 (3H, s), 2.95–3.90(11H, m)

EXAMPLE 81

5-Deoxy-5-[4-(2,3,4-trimethoxybenzyl)piperazin-1-yl]-1.4;3.6-dianhydro-L-iditol 2-nitrate (Compound 73)

5.0 g (4.34 mmols) of 2,3,4-trimethoxybenzyl alcohol was dropwise added to 10 ml of conc. hydrochloric acid under stirring at 0° C. The mixture was stirred at 0° C. for further 5 minutes. After the reaction, water was added to the mixture followed by extraction of the solution with diethyl ether. The diethyl ether layer was dried over anhydrous sodium sulfate, and the solvent was evaporated under reduced pressure to afford 4.80 g of 2,3,4-trimethoxybenzyl chloride as a crude product.

A mixture of 2.44 g of the crude product of 2,3,4-trimethoxybenzyl chloride described above, 1.73 g (6.67 mmols) of Compound b obtained in Reference Example 2 and 50 ml of methyl ethyl ketone was stirred at room temperature for 4 days. The mixture was concentrated under reduced pressure and to the residue an aqueous saturated sodium bicarbonate solution was added followed by extraction of the solution with chloroform. The chloroform layer was dried over anhydrous sodium sulfate. The solvent was evaporated under reduced pressure, and the residue was purified by silica gel column chromatography (eluent: chloroform/methanol =50/1) to afford 0.56 g (yield: 21%) of Compound 73.
MS (EI) m/z: 439 (M$^+$)
IR (nujol) cm$^{-1}$: 1648
NMR (DMSO-d$_6$) δ (ppm): 6.95(1H, d, J=8.6 Hz), 6.75(1H, d, J=8.6 Hz), 5.35(1H, m), 4.62(2H, m), 3.90–4.05 (3H, m), 3.77(6H, s), 3.73(3H, s), 3.56(1H, m), 2.79(1H, m), 2.15–3.90(10H, m)

EXAMPLE 82

5-[4-(5-Chlorobenzothiazol-2-yl)piperazin-1-yl]-5-deoxy-1.4;3.6-dianhydro-L-iditol 2-nitrate hydrochloride (Compound 74)

With stirring under ice cooling, 2.00 g (9.92 mmols) of 5-chloro-2-mercaptobenzothiazole was added gradually to 10 ml of a solution of 0.24 g (10.00 mmols) of sodium hydroxide in dimethylformamide (DMF). The mixture was dropwise added to 20 ml of a solution of 0.62 ml (9.96 mmols) of iodomethane in 20 ml of DMF with stirring under ice cooling and the mixture was stirred for further 30 minutes under ice cooling. The mixture was concentrated under reduced pressure, and to the residue was added an aqueous saturated sodium bicarbonate followed by extraction of the solution with chloroform. The chloroform layer was dried over anhydrous sodium sulfate. The solvent was evaporated under reduced pressure, and the residue was purified by silica gel column chromatography (eluent: chloroform/methanol =100/1) to afford 2.10 g (yield: 98%) of 5-chloro-2-methylthiobenzothiazole.

A mixture of 1.80 g (8.34 mmols) of 5-chloro-2-methylthiobenzothiazole, 1.80 g (11.39 mmols) of potassium permanganate and 45 ml of 50% aqueous acetic acid solution was stirred at room temperature for an hour. After the reaction, a 30.0 to 35.5% aqueous hydrogen peroxide solution was dropwise added to the mixture with stirring under ice cooling until to be colorless. An aqueous sodium thiosulfate was added to the mixture followed by extraction of the solution with chloroform. The chloroform layer was dried over anhydrous sodium sulfate, and the solvent was evaporated under reduced pressure to afford 2.05 g (yield: 100%) of 5-chloro-2-methanesulfonylbenzothiazole. A mixture of 1.64 g (6.62 mmols) of the above compound, 2.57 g (9.91 mmols) of Compound b obtained in Reference Example 2 and 40 ml of acetonitrile was heated under reflux for 20 hours. The mixture was concentrated under reduced pressure, and the residue was purified by silica gel column chromatography (eluent: chloroform/methanol = 100/1).

The product was dissolved in chloroform, and to this solution was added ethyl acetate saturated with hydrogen chloride. The mixture was poured into cold diethyl ether and the precipitated crystals were taken out by filtration and dried to afford 0.61 g (yield: 11%) of Compound 74.

MS (EI) m/z: 426 (M+)

IR (KBr) cm$^{-1}$: 2954(br), 2660(br), 2160(br), 1639,

NMR (DMSO-d$_6$) δ (ppm): 7.87(1H, d, J=8.4 Hz), 7.56(1H, d, J=2.0 Hz), 7.18(1H, dd, J=8.4, 2.0 Hz), 5.45(1H,

EXAMPLE 83

5-Deoxy-5-[4-(pyrido[3,2-d]thiazol-2-yl)piperazin-1-yl]-1.4;3.6-dianhydro-L-iditol 2-nitrate hydrochloride (Compound 75)

A mixture of 6.43 g (50.0 mmols) of 3-amino-2-chloropyridine, 50 ml of carbon disulfide and 50 ml of DMF was heated under reflux for 6 days. An excess of carbon disulfide was evaporated under reduced pressure, and the residue was poured into 300 ml of ice water with stirring. The precipitated crystals was taken out by filtration and dried to afford 7.57 g (yield: 90%) of pyrido[3,2-d]thiazo-line-2-thione.

Then, Compound 75 was obtained (yield: 93%, 94%, 21%) in the same manner as in Example 82 except that pyrido[3,2-d]thiazolin-2-one was used in place of 5-chloro-2-mercaptobenzothiazole.

Melting point: 166°–170° C.

MS (EI) m/z: 393 (M+)

IR (KBr) cm$^{-1}$: 2940(br), 2510(br), 1642, 1552, 1274

NMR (DMSO-d$_6$) δ (ppm): 8.24(1H, d, J=4.8 Hz), 7.87(1H, d, J=8.2 Hz), 7.39(1H, dd, J=8.2, 4.8 Hz), 5.45(1H, m), 5.35(1H, m), 3.1–5.1(14H, m)

EXAMPLE 84

5-[4-(Benzimidazol-2-yl)piperazin-1-yl]-5-deoxy-1.4;3.6-dianhydro-L-iditol 2-nitrate hydrochloride (Compound 76)

A mixture of 1.50 g [5.79 mmols) of Compound b obtained in Reference Example 2, 0.89 g (5.83 mmols) of 2-chlorobenzimidazole (Japanese Published Unexamined Patent Application No. 149263/80, U.S. Pat. No. 4,314,065 and EP-B No. 18080) and 40 ml of n-butanol was heated under reflux for 10 hours. The mixture was concentrated under reduced pressure, and to the residue was added an aqueous saturated sodium bicarbonate solution followed by extraction of the solution with chloroform. The chloroform layer was dried over anhydrous sodium sulfate. The solvent was evaporated under reduced pressure, and the residue was purified by silica gel column chromatography (eluent: chloroform/methanol =20/1). The product was dissolved in chloroform, and to this solution was added ethyl acetate saturated with hydrogen chloride. The mixture was poured into cold diethyl ether and the precipitated crystals were taken out by filtration and dried to afford 0.94 g (yield: 34%) of Compound 76.

Melting point: 223°–227° C.

MS (EI) m/z: 375 (M+)

IR (KBr) cm$^{-1}$: 2950(br), 1647, 1281

NMR (DMSO-d$_6$) δ (ppm): 13.81(1H, br), 7.44(2H, m), 7.30(2H, m), 5.44(1H, m), 5.20(1H, m), 4.85(2H, m), 2.6–4.5(13H, m)

EXAMPLE 85

5-[4-(2-Chloro-4-phenylthiazol-5-yl)piperazin-1-yl]-5-deoxy-1.4;3.6-dianhydro-L-iditol 2-nitrate hydrochloride (Compound 77)

With stirring at room temperature, 2.50 g (12.9 mmols) of 2-mercapto-4-phenylthiazole was added to 13.0 ml of sulfuryl chloride. The mixture was stirred at room temperature for further 30 minutes. After the reaction, water was gradually added with stirring under ice cooling and the mixture was extracted with methylene chloride. The methylene chloride layer was washed with water and then dried over anhydrous sodium sulfate. The solvent was evaporated under reduced pressure to afford 2,5-dichloro-4-phenylthiazole as a crude product.

A mixture of the crude product described above, 3.34 g (12.9 mmols) of Compound b obtained in Reference Example 2, 1.80 ml (12.9 mmols) of triethylamine and 30 ml of acetonitrile was heated under reflux for 15 hours. The mixture was concentrated under reduced pressure, and to the residue was added an aqueous saturated sodium bicarbonate solution followed by extraction of the solution with chloroform. The chloroform layer was dried over anhydrous sodium sulfate. The solvent was evaporated under reduced pressure and the residue was purified by silica gel column chromatography (eluent:-chloroform).

The product was dissolved in chloroform, and to the solution was added ethyl acetate saturated with hydrogen chloride. The mixture was poured into cold diethyl ether and the precipitated crystals were taken out by filtration and dried to afford 2.38 g (yield: 33%) of Compound 77.

Melting point: 125.0°–125.5° C.

MS (EI) m/z: 452 (M+)

IR (KBr) cm$^{-1}$: 2928(br), 2360(br), 1643, 1363, 1277, 1176

NMR (DMSO-d$_6$) δ (ppm): 7.96(2H, m), 7.45–7.63(3H, m), 5.43(1H, m), 5.18(1H, m), 4.81(1H, m), 3.05–4.25 (13H, m)

EXAMPLE 86

5-[4-(4-Amino-6,7-dimethoxyquinazolin-2-yl)piperazin-1-yl]-5-deoxy-1.4;3.6-dianhydro-L-iditol 2-nitrate hydrochloride (Compound 78)

A mixture of 1.00 g (3.87 mmols) of Compound b obtained in Reference Example 2, 0.95 g (3.96 mmols) of 4-amino-2-chloro-6,7-dimethoxyquinazoline, 0.53 ml (3.87 mmols) of triethylamine and 30 ml of n-butanol was heated under reflux for 3 hours. The mixture was concentrated under reduced pressure, and the residue was purified by silica gel column chromatography (eluent: chloroform/methanol =20/1). The product was dissolved in chloroform, and to the solution was added ethyl acetate saturated with hydrogen chloride. The mixture was poured into cold diethyl ether and the precipitated crystals were taken out by filtration and dried to afford 1.35 g (yield: 59%) of Compound 78.

Melting point: 253°-261° C.

MS (FAB) m/z: 463 (M++1) 30 IR (KBr) cm$^{-1}$: 3170(br), 2570(br), 1640, 1595, 1276

NMR (DMSO-d$_6$) δ (ppm): 9.04(1H, brs), 8.74(1H, brs), 7.80(1H, s), 7.68(1H, s), 5.45(1H, m), 5.30(1H, m), 4.87(1H, m), 3.88(3H, s), 3.86(3H, s), 3.0 4.3(13H, m)

EXAMPLE 87

5-[4-(4-Amino-6,7,8-trimethoxyquinazolin-2-yl)piperazin-1yl]-5-deoxy-1.4;3.6-dianhydro-L-iditol 2-nitrate hydrochloride (Compound 79)

A mixture of 4.94 g (21.7 mmols) of 3,4,5-trimethoxyanthranilic acid and 15.15 g (249.8 mmols) of urea was heated at 145° C for an hour with stirring. After cooling, water was added and the mixture was heated at the boiling point with stirring. The solid was taken out by filtration and dried to afford 2.47 g (yield: 45%) of 6,7,8-trimethoxyquinazoline-2,4-dione.

NMR (DMSO-d$_6$) δ (ppm): 11.18(1H, brs), 10.57(1H, brs), 7.18(1H, s), 3.88(3H, s), 3.84(3H, s), 3.81(3H, s)

A mixture of 2.17 g (8.60 mmols) of the compound described above, 0.69 ml (5.47 mmols) of N,N-dimethylaniline and 7.3 ml of phosphorus oxychloride was heated under reflux for an hour and a half. After cooling, the solution was poured into 55 ml of ice water and stirred. The precipitated solid was taken out by filtration and dried to afford 2.17 g (yield: 87%) of 2,4-dichloro-6,7,8-trimethoxyquinazoline.

NMR (CDCl$_3$) δ (ppm): 7.22(1H, s), 4.14(3H, s), 4.13 (3H, s), 4.04(3H, s)

A mixture of 2.17 g (7.51 mmols) of the compound described above, 50 ml of 25 to 28% aqueous ammonia solution and 50 ml of dioxan was stirred at room temperature for an hour and a half. The mixture was concentrated under reduced pressure, and the residue was purified by silica gel column chromatography (eluent: chloroform/methanol =40/1) to afford 1.61 g (yield: 84%) of 4-amino-2-chloro-6,7,8-trimethoxyquinazoline.

NMR (DMSO-d$_6$) δ (ppm): 8.06(2H-., brs), 7.47(1H, s), 3.94(3H, s), 3.89(6H, s)

Then, Compound 79 was obtained (yield: 45%) in the same manner as in Example 86 except that 4-amino-2-chloro- 6,7,8-trimethoxyquinazoline was used in place of 4-amino-2-chloro-6,7-dimethoxyquinazoline and the period for heating under reflux was changed from 3 hours to 6 hours.

Melting point: 104°-105° C.

MS (EI) m/z: 492 (M+)

IR (KBr) cm$^{-1}$: 2570(br), 1653, 1633, 1589, 1471, 1277

NMR (DMSO-d$_6$) δ (ppm): 9.01(2H, brs), 7.74(1H, s), 5.45(1H, m), 5.28(1H, m), 4.86(1H, m), 3.96(3H, s), 3.95(3H, s), 3.91(3H, s), 2.90-4.35(13H, m)

EXAMPLE 88

5-Deoxy-5-[4-(pyridin-3-yl)carbonylpiperazin-1-yl]-1.4;3.6-dianhydro-L-iditol 2-nitrate hydrochloride (Compound 80')

A mixture of 0.74 g (5.61 mmols) of nicotinic acid, 1.56 ml (11.2 mmols) of triethylamine and 12 ml of a solvent mixture of 2-butanol and acetonitrile (5/1) was stirred at 0° C., and to the solution was dropwise added 1.6 ml of a solution of 0.74 ml (5.64 mmols) of isobutyl chloroformate in a solvent mixture of 2-butanol and acetonitrile (5/1). The mixture was stirred at 0° C. for further 5 minutes. Then, 6 ml of a solution of 1.45 g (5.59 mmols) of Compound b obtained in Reference Example 2 in a solvent mixture of 2-butanol and acetonitrile (5/1) was dropwise added to the reaction mixture followed by stirring the solution at 0° C. for 2 hours. The mixture was concentrated under reduced pressure, and the residue was purified by silica gel column chromatography (eluent: chloroform/methanol =50/1).

The product was dissolved in chloroform and to the solution was added methanol saturated with hydrogen chloride. The mixture was poured into cold diethyl ether and the precipitated crystals were taken out by filtration and dried to afford 1.00 g (yield: 41%) of Compound 80'.

Melting point: 176.0°-180.0° C.

MS (EI) m/z: 364 (M+)

IR (KBr) cm$^{-1}$: 1643, 1440, 1280

NMR (DMSO-d$_6$) δ (ppm): 8.89(1H, s), 8.84(1H, d, J=5.3 Hz), 8.27(1H, d, J=7.9 Hz), 7.82(1H, dd, J=7.9, 5.3 Hz), 5.45(1H, m), 5.34(1H, m), 4.86(1H, m). 4.27(1H, m), 4.17(1H, m), 4.07(2H, m), 3.94(1H, m), 3.10-5.25(8H, m)

EXAMPLE 89

5-Deoxy-5-[4-(pyridin-2-yl)carbonylpiperazin-1-yl]-1.4;3.6-dianhydro-L-iditol 2-nitrate hydrochloride (Compound 81)

A mixture of 0.80 g (6.50 mmols) of picolinic acid and 8 ml of methylene chloride was stirred at 0° C., and to the solution were added 1.1 ml (13.60 mmols) of pyridine and 0.47 ml (6.48 ml) of thionyl chloride in succession. The mixture was stirred at 0° C. for further 30 minutes (solution e,crc/A/ ).

A mixture of 1.59 g (6.13 mmols) of Compound b obtained in Reference Example 2 and 15 ml of acetonitrile was stirred at 0° C. and solution e,crc/A/ was dropwise added thereto. The mixture was stirred at 0° C. for further an hour. The mixture was concentrated under reduced pressure, and to the residue was added an aqueous saturated sodium bicarbonate solution followed by extraction of the solution with chloroform. The chloroform layer was dried over anhydrous sodium sulfate. The solvent was evaporated under reduced pressure, and the residue was purified by silica gel column chromatography (eluent: chloroform/methanol =40/1).

The product was dissolved in chloroform, and to the solution was added ethyl acetate saturated with hydrogen chloride. The mixture was poured into cold diethyl ether and the precipitated crystals were taken out by filtration and dried to afford 0.95 g (yield: 35%) of Compound 81.

Melting point: 168°-169° C.

MS (EI) m/z: 364 (M+)

IR (KBr) cm$^{-1}$: 1652, 1455, 1279

NMR (DMSO-d$_6$) δ (ppm): 8.63(1H, d, J=5.6 Hz), 8.00(1H, dd, J=7.9, 7.8 Hz), 7.71(1H, d, J=7.8 Hz), 7.56(1H, dd, J=7.9, 5.6 Hz), 5.44(1H, m), 5.32(1H, m), 4.85 (1H, m), 3.0-4.8(13H, m)

EXAMPLE 90

5-Deoxy-5-[4-(pyridin-4-yl)carbonylpiperazin-1-yl]-1.4;3.6-dianhydro-L-iditol 2-nitrate hydrochloride (Compound 82)

Compound 82 was obtained (yield: 24%) in a manner similar to Example 89 except that isonicotinic acid was used in place of nicotinic acid.

Melting point: 164°–168° C.
MS (EI) m/z: 364 (M+)
IR (KBr) cm$^{-1}$: 1646, 1438, 1280
NMR (DMSO-d$_6$) δ (ppm): 8.92(2H, d, J=6.3 Hz), 7.90(2H, d, J=6.3 Hz), 5.45(1H, m), 5.34(1H, m), 4.95(1H, m), 4.27(1H, m), 4.16(1H, m), 4.07(2H, m), 3.93 (1H, m), 3.05–5.25(8H, m)

EXAMPLE 91

5-Deoxy-5-[4-(furan-2-yl)carbonylpiperazin-1-yl]-1.4;3.6-dianhydro-L-iditol 2-nitrate hydrochloride (Compound 83)

Compound 83 was obtained (yield: 31%) in a manner similar to Example 89 except that one molar equivalent of 2-furoyl chloride was used in place of solution (A) and one molar equivalent of triethylamine was added prior to adding 2-furoyl chloride.

Melting point: 183 185° C.
MS (EI) m/z: 353 (M+)
NMR (DMSO-d$_6$) δ (ppm): 7.87(1H, m), 7.10(1H, m), 6.65 (1H, m), 5.44(1H, m), 5.25(1H, m), 4.84(1H, m), 2.90–4.70(13H, m)

EXAMPLE 92

5-(4-Benzoylpiperazin-1-yl)-5-deoxy-1.4;3.6-dianhydro-L-iditol 2-nitrate hydrochloride (Compound 84)

Compound 84 was obtained (yield: 85%) in a manner similar to Example 89 except that one molar equivalent of benzoyl chloride was used in place of solution (A), one molar equivalent of triethylamine was added prior to adding benzoyl chloride and the stirring period was changed from an hour to 30 minutes.

MS (EI) m/z: 363 (M+)
IR (KBr) cm 1645, 1630, 1424, 1285
NMR (DMSO-d$_6$) δ (ppm): 7.47(5H, s), 5.44(1H, m), 5.27 (1H, m), 4.85(1H, m), 4.10–4.30(2H, m), 4.07(2H, m), 2.95–4.05(9H, m)

EXAMPLE 93

5-[4-(2-chIropyridin-3-yl)carbonylpiperazin-1-yl]-5-deoxy-1.4;3.6-dianhydro-L-iditol 2-nitrate hydrochloride (Compound 85)

Compound 85 was obtained (yield: 73%) in a manner similar to Example 89 except that 2-chloronicotinic acid was used in place of picolinic acid and the stirring period was changed from an hour to 3 hours and a half.

MS (EI) m/z: 398 (M+)
IR (KBr) cm$^{-1}$: 2300(br), 1642, 1615, 1434, 1406, 1300, 1283
NMR (DMSO-d$_6$) δ (ppm): 8.51(1H, d, J=4.9 Hz), 7.98(1H, d, J=7.6 Hz), 7.56(1H, dd, J=7.6, 4.9 Hz), 5.44(1H, m), 5.27(1H, m), 4.83(1H, m), 4.17(2H, m), 4.07 (2H, m), 2.90–4.05(9H, m)

EXAMPLE 94

5-Deoxy-5-[4-(pirazin-2-yl)carbonylpiperazin-1-yl]-1.4;3.6-dianhydro-L-iditol 2-nitrate hydrochloride (Compound 86)

Compound 86 was obtained (yield: 91%) in a manner similar to Example 89 except that pirazinecarboxylic acid was used in place of picolinic acid.

Melting point: 164° C.
Elemental analysis as C$_{15}$H$_{19}$N$_5$O$_6$·1.8 HCl.
Calcd. (%); C, 41.80 H, 4.86 N, 16.25.
Found (%); C, 42.02 H, 5.11 N, 15.97.
IR (KBr) cm$^{-1}$: 2440(br), 1667, 1643, 1428, 1279
NMR (DMSO-d$_6$) δ (ppm): 8.91(1H, s), 8.79(1H, d, J=2.6 Hz), 8.69(1H, d, J=2.6 Hz), 5.44(1H, m), 5.27 (1H, m), 4.84(1H, m), 4.17(2H, m), 4.06(2H, m), 2.85–4.05(9H, m)

EXAMPLE 95

5-Deoxy-5-[4-(2,3,4-trimethoxybenzoyl)piperazin-1-yl]-1.4;3.6-dianhydro-L-iditol 2-nitratehydrochloride (Compound Compound 87 was obtained (yield: 42%) in a manner similar to Example 89 except that 2,3,4-trimethoxybenzoic acid was used in place of picolinic acid and the stirring period was changed from an hour to 2 hours.

MS (EI) m/z: 453 (M+)
IR (KBr) cm$^{-1}$: 2350(br), 1644, 1598, 1466, 1429, 1292, 1275, 1096
NMR (DMSO-d$_6$) δ (ppm): 7.00(1H, d, J=8.6 Hz), 6.87(1H, d, J=8.6 Hz), 5.43(1H, m), 5.24(1H, m), 4.82(1H, m), 4.10–4.25(2H, m), 4.06(2H, m), 3.83(3H, s), 3.79(3H, s), 3.77(3H, s), 2.85–4.00(9H, m)

EXAMPLE 96

5-Deoxy-5-[4-(3,4,5-trimethoxybenzoyl)piperazin-1-yl]-1.4;3.6-dianhydro-L-iditol 2-nitrate hydrochloride (Compound 88)

Compound 88 was obtained (yield: 41%) in a manner similar to Example 89 except that 3,4,5-trimethoxybenzoic acid was used in place of picolinic acid and the stirring period was changed from an hour to 2 hours.

MS (EI) m/z: 453 (M+)
IR (KBr) cm$^{-1}$: 1642, 1584, 1463, 1417, 1278, 1125
NMR (DMSO-d$_6$) δ (ppm): 6.75(2H, s), 5.44(1H, m), 5.28 (1H, m), 4.84(1H, m), 4.10–4.30(2H, m), 4.07(2H, m), 3.81(6H, s), 3.70(3H, s), 2.95–4.00(9H, m)

EXAMPLE 97

5-[4-(6-Chloropyridin-3-yl)carbonylpiperazin-1-yl]-5-deoxy-1.4;3.6-dianhydro-L-iditol 2-nitrate hydrochloride (Compound 89)

Compound 89 was obtained (yield: 64%) in a manner similar to Example 89 except that 6-chloronicotinic acid was used in place of picolinic acid and the stirring period was changed from an hour to 2 hours.

Melting point: 145°–146° C.
MS (EI) m/z: 398 (M+)
IR (KBr) cm$^{-1}$: 1654, 1639, 1433, 1279
NMR (DMSO-d$_6$) δ (ppm): 8.54(1H, s), 7.98(1H, d, J=8.3 Hz), 7.64(1H, d, J=8.3 Hz), 5.45(1H, m), 5.30 (1H, m), 4.86(1H, m), 4.24(1H, m), 4.16(1H, m), 4.07(2H, m), 2.95–4.65(9H, m)

EXAMPLE 98

5-[4-(5-Bromopyridin-3-yl)carbonylpiperazin-1-yl]-5-deoxy-1.4;3.6-dianhydro-L-iditol 2-nitrate hydrochloride (Compound 90)

Compound 90 was obtained (yield: 79%) in a manner similar to Example 89 except that 5-bromonicotinic acid was used in place of picolinic acid and the stirring period was changed from an hour to 4 hours.
Melting point: 138.5°–139.0° C.
MS (EI) m/z: 442 (M+)
IR (KBr) cm$^{-1}$: 2580(br), 1653, 1643, 1439, 1280
NMR (DMSO-d$_6$) δ (ppm); 8.82(1H, s), 8.67(1H, s), 8.19 (1H, s), 5.45(1H, m), 5.32(1H, m), 4.86(1H, m), 2.95–4.65(13H, m)

EXAMPLE 99

5-Deoxy-5-[4-(2-methylpyridin-3-yl)carbonylpiperazin-1yl-]-1.4;3.6-dianhydro-L-iditol 2-nitrate hydrochloride (Compound 91)

Compound 91 was obtained (yield: 84%) in a manner similar to Example 89 except that 2-methylnicotinic acid was used in place of picolinic acid and the stirring period was changed from an hour to 4 hours.
Melting point: 188°–189° C.
MS (EI) m/z: 378 (M+)
IR (KBr) cm$^{-1}$: 1651, 1641, 1441, 1281
NMR (DMSO-d$_6$) δ (ppm): 8.75(1H, d, J=5.6 Hz), 8.35(1H, d, J=7.8 Hz), 7.79(1H, dd, J=7.8, 5.6 Hz), 5.45 (1H, m), 5.33(1H, m), 4.85(1H, m), 4.24(1H, m), 4.17(1H, m), 4.07(2H, m), 3.93(1H, m), 3.00–5.15 (8H, m), 2.64(3H, s)

EXAMPLE 100

5-Deoxy-5-[4-(quinolin-3-yl)carbonylpiperazin-1-yl]-1.4;3.6-dianhydro-L-iditol 2-nitrate hydrochloride (Compound 92)

Compound 92 was obtained (yield: 83%) in a manner similar to Example 89 except that 3-quinolinecarboxylic acid was used in place of picolinic acid and the stirring period was changed from an hour to 4 hours.
Melting point: 191°–192° C.
MS (EI) m/z: 414 (M+)
IR (KBr) cm$^{-1}$: 2570(br), 1641, 1439, 1279
NMR (DMSO-d$_6$) δ (ppm): 9.13(1H, s), 8.79(1H, s), 8.13–8.28(2H, m), 7.98(1H, m), 7.80(1H, m), 5.46 (1H, m), 5.35(1H, m, 4.87(1H, m), 4.29(1H, m), 4.18(1H, m), 4.08(2H, m), 3.96(1H, m), 3.10–5.20 (8H, m)

EXAMPLE 101

5-Deoxy-5-[4-(6-methylpyridin-3-yl)carbonylpiperazin-1-yl]-1.4;3.6-dianhydro-L-iditol 2-nitrate hydrochloride (Compound 93)

Compound 93 was obtained (yield: 85%) in a manner similar to Example 89 except that 6-methylnicotinic acid was used in place of picolinic acid.
Melting point: 166°–168° C.
MS (EI) m/z: 378 (M+)
IR (KBr) cm$^{-1}$: 1651, 1641, 1439, 1280
NMR (DMSO-d$_6$) δ (ppm): 8.80(1H, s), 8.24(1H, d, J=7.7 Hz), 7.75(1H, d, J=7.7 Hz), 5.45(1H, m), 5.32 (1H, m), 4.86(1H, m), 3.0–4.8(13H, m), 2.69(3H, s)

EXAMPLE 102

5-Deoxy-5-[4-(thiophen-3-yl)carbonylpiperazin-1-yl]-1.4;3.6-dianhydro-L-iditol 2-nitrate hydrochloride (Compound 94)

Compound 94 was obtained (yield: 56%) in a manner similar to Example 89 except that 3-thiophenecarboxylic acid was used in place of picolinic acid and the stirring period was changed from an hour to 2 hours.
MS (EI) m/z: 369 (M+)
IR (KBr) cm$^{-1}$: 1645, 1631, 1428, 1284
NMR (DMSO-d$_6$) δ (ppm): 7.88(1H, s), 7.64(1H, d, J=5.0 Hz), 7.25(1H, d, J=5.0 Hz), 5.44(1H, m), 5.26 (1H, m), 4.85(1H, m), 2.8–4.6(13H, m)

EXAMPLE 103

5-Deoxy-5-[4-(thiophen-2-yl)carbonylpiperazin-1-yl]-1.4;3.6-dianhydro-L-iditol 2-nitrate hydrochloride (Compound 111)

A mixture of 1.59 g (6.13 mmols) of compound b obtained in Reference Example 2 and 15 ml of acetonitrile was stirred at 0° C. After 0.86 ml (6.17 mmols) of triethylamine was added to the mixture, 0.90 g (6.14 mmols) of 2-thenoyl chloride was dropwise added thereto. The mixture was stirred at 0° C. for further 30 minutes. The mixture was concentrated under reduced pressure, and a saturated aqueous sodium bicarbonate was added to the residue. The solution was extracted with chloroform, and the chloroform layer was dried over anhydrous sodium sulfate. The solvent was evaporated under reduced pressure, and the residue was purified by silica gel column chromatography (eluent: chloroform/methanol =40/1) to give a free form of the desired product.

Compound 111 was obtained 1.74 g (yield: 70%) in a manner similar to Example 89 from the free form of the product.
Melting point: 180°–196° C.
MS (EI) m/z: 369 (M+)
IR (KBr) cm$^{-1}$: 1642, 1628, 1426, 1291
NMR (DMSO-d$_6$) δ (ppm): 7.80(1H, d, J=5.1 Hz), 7.50(1H, d, J=3.7 Hz), 7.15(1H, dd, J=5.1, 3.7 Hz), 5.44 (1H, m), 5.26(1H, m), 4.85(1H, m), 2.9–4.7(13H, m)

EXAMPLE 104

5-Deoxy-5-[4-(furan-3-yl)carbonylpiperazin-1-yl]-1.4;3.6-dianhydro-L-iditol 2-nitrate hydrochloride (Compound 112)

Compound 112 was obtained (yield: 50%) in a manner similar to Example 89 except that 3-furancarboxylic acid was used in place of picolinic acid.
Melting point: 213°–217° C.
IR (KBr) cm$^{-1}$: 1645, 1633, 1424, 1285
NMR (DMSO-d$_6$) δ (ppm): 8.10(1H, s), 7.76(1H, m), 6.70 (1H, m), 5.44(1H, m), 5.28(1H, m), 4.85(1H, m), 2.8–4 7(13H, m)

EXAMPLE 105

5-Deoxy-5-[4-(pyridin-3-yl)carbonylpiperazin N$^1$-oxid-1-yl]-1.4;3.6-dianhydro-L-iditol 2-nitrate hydrochloride (Compound 113)

A mixture of 0.80 g (2.20 mmols) of Compound 80 obtained in Example 88, 0.38 g (2.20 mmols) of m-chloroperbenzoic acid, 26 ml of methylene chloride and 26 ml of an aqueous saturated sodium bicarbonate solution was ..rred at 0° C. for 2 hours. After the reaction, the mixture was extracted with chloroform and the chloroform layer was dried over anhydrous sodium sulfate. The solvent was evaporated under reduced pressure, and the residue was purified by silica gel column chromatography (eluent: chloroform/methanol =5/1). The product was dissolved in chloroform, and to this solution was added methanol saturated with hydrogen chloride. The mixture was poured into cold ethyl acetate and the precipitated crystals were taken out by filtration and dried to afford 0.92 g (yield: 100%) of Compound 113.

Melting point: 79.5°-82.0° C. MS (FAB) m/z: 381 (M$^+$+1)

IR (KBr) cm$^{-1}$: 1658, 1641, 1443, 1277, 1090, 855

NMR (DMSO-d$_6$) δ (ppm): 8.89(1H, s), 8.83(1H, d, J=5.5 Hz), 8.24(1H, d, J=7.6 Hz), 7.79(1H, m), 5.55 (1H, m), 5.48(1H, m), 4.89(1H, m), 3.2-5.2(13H, m)

EXAMPLE 106

5-Deoxy-5-[4-(6-hydroxypyridin-3-yl)carbonylpiperazin-1-yl]-1.4;3.6-dianhydro-L-iditol 2-nitrate hydrochloride (Compound 114)

Compound 114 was obtained (yield: 10%) in a manner similar to Example 88 except that 6-hydroxynicotinic acid was used in place of nicotinic acid, the stirring period was changed from 2 hours to 5 hours and an eluent was methanol (20/1).

Melting point: 185.0°-187.0° C.
MS (FAB) m/z: 381 (M$^+$+1)
IR (KBr) cm$^{-1}$: 3420(br), 1673, 1634, 1446, 1281
NMR (DMSO-d$_6$) δ (ppm): 7.66(1H, s), 7.53(1H, d, J=9.5 Hz), 6.37(1H, d, J=9.5 Hz), 5.45(1H, m), 5.30(1H, m), 4.85(1H, m), 2.8-4.6(13H, m)

EXAMPLE 107

5-Deoxy-5-[4-(2-hydroxypyridin-3-yl)carbonylpiperazin-1-yl-]-1.4;3.6-dianhydro-L-iditol 2-nitrate hydrochloride (Compound 115)

Compound 115 was obtained (yield: 32%) in a manner similar to Example 88 except that 2-hydroxynicotinic acid was used in place of nicotinic acid, the stirring period was changed from 2 hours to 4 hours and an eluent was changed from chloroform/methanol (50/1) to chloroform/methanol (20/1).

MS (FAB) m/z: 381 (M$^+$+1)
IR (KBr) cm$^{-1}$: 3430(br), 1726, 1670, 1640, 1280
NMR (DMSO-d$_6$) δ (ppm): 9.52(1H, brs), 7.60(1H, d, J=6.8 Hz), 7.53(1H, d, J=6.5 Hz), 6.30(1H, m), 5.43 (1H, m), 5.28(1H, m), 4.83(1H, m), 2.7-4.7(13H, m)

EXAMPLE 108

5-Deoxy-5-[4-(2-methylthiazol-4-yl)carbonylpiperazin-1-yl]-1.4;3.6-dianhydro-L-iditol 2-nitrate hydrochloride (Compound 116)

Compound 116 was obtained (yield: 29%) in a manner similar to Example 89 except that 2-methylthiazole-4-carboxylic acid (EP-A No. 300400) was used in place of picolinic acid.

Melting point: 87.0°-88.0° C.
MS (EI) m/z: 384 (M$^+$)
IR (KBr) cm$^{-1}$: 1658, 1642, 1436, 1277, 846
NMR (DMSO-d$_6$) δ (ppm): 8.06(1H, s), 5.44(1H, m), 5.31 (1H, m), 4.85(1H, m), 2.9-5.0(13H, m), 2.70(3H, s)

EXAMPLE 109

5-Deoxy-5-[4-(pyridin-3-yl)carbonylpiperazin-1-yl]-1.4;3.6-dianhydro-L-iditol 2-nitrate (Compound 80)

The free form of Compound 80' obtained in Example 88 was recrystallized two times from isopropyl alcohol and dried to afford Compound 80 in good purity.

[α]$_{589}^{15°C.}$=+229.46 (c=0.998, acetone)
Melting point: 134.2°-135.3° C.
Elemental analysis: as C$_{16}$H$_{20}$N$_4$O$_6$.
Calcd. (%); C, 52.74 H, 5.53 N, 15.38.
Found (%); C, 52.73 H, 5.54 N, 15.32.
IR (KBr) cm$^{-1}$: 1656, 1636, 1616, 1450, 1273, 1008, 876
NMR (CDCl$_3$) δ (ppm): 8.63-8.76(2H, m), 7.76(1H, d, J=7.7 Hz), 7.37(1H, dd, J=7.7, 4.8 Hz), 5.32(1H, m), 4.70(1H, m), 4.56(1H, m), 3.95-4.20(3H, m), 3.71 (1H, m), 3.3-4.0(4H, m), 2.93(1H, m), 2.2-2.8 (4H, m)
MS (EI) m/z: 364 (M$^+$)

EXAMPLE 110

5-Deoxy-5-[4-(pyridin-3-yl)carbonylpiperazin-1-yl]-1.4;3.6-dianhydro-L-iditol (Compound 117)

A mixture of 0.80 g (6.50 mmols) of nicotinic acid and 8 ml of methylenechloride was stirred at 0° C., and 1.1 ml (13.60 mmols) of pyridine and 0.47 ml (6.48 m) of thionylchloride were dropwise added to the solution in succession. The mixture was stirred at 0° C. for further 30 minutes (solution A mixture of 1.59 g (6.13 mmols) of compound a obtained in Reference Example 1 and 15 ml of acetonitrile was stirred at 0° C. Solution e,crc/A/ ' was dropwise added thereto and the mixture was stirred at room temperature for one day. The mixture was concentrated under reduced pressure, and an aqueous saturated sodium bicarbonate was added to the residue. The solution was extracted with chloroform, and the chloroform layer was dried over anhydrous sodium sulfate. The solvent was evaporated under reduced pressure, and the residue was purified by silica gel column chromatography (eluent: chloroform/methanol =5/1) to give the desired product.

The product was dissolved in isopropyl alcohol by heating, and the mixture was poured into n-hexane and the precipitated crystals were taken out by filtration and dried to afford 0.56 g of Compound 117 (yield: 25%).

Melting point: 140.5°-141.0° C.
MS (EI) m/z: 319 (M$^+$)
IR (KBr) cm$^{-1}$: 3410(br), 1622, 1593, 1440, 1295, 1264, 1074, 1044
NMR (DMSO-d$_6$) δ (ppm): 8.64(1H, d, J=4.9 Hz), 8.60(1H, s), 7.82(1H, d, J=8.1 Hz), 7.47(1H, m), 5.09(1H, m), 4.57(1H, m), 4.22(1H, m), 4.03(1H, m), 3.88 (1H, m), 3.70(1H, m), 2.2-3.8(11H, m)

EXAMPLE 111

5-Deoxy-5-[4-(pyridin-3-yl)carbonylpiperazin-1-yl]-1.4;3.6-dianhydro-D-glucitol 2-nitrate (Compound 118)

Compound 118 was obtained in a manner similar to Example 89 except that nicotinic acid was used in place of picolinic acid and Compound d obtained in Reference Example 4 was used in place of Compound b. The product was recrystallized from isopropyl alcohol/n-hexane system and dried to afford Compound 118 in good purity (yield: 60%).

Melting point: 162.0°-164.0° C.

Elemental analysis: as $C_{16}H_{20}N_4O_6$.
Calcd. (%); C, 52.74 H, 5.53 N, 15.38.
Found (%); C, 52.98 H, 5.76 N, 15.22.
IR (KBr) cm$^{-1}$: 1626, 1589, 1443, 1274, 1009, 861
NMR (CDCl$_3$) δ (ppm): 8.50–8.65(2H, m), 7.76(1H, d, J=7.9 Hz), 7.37(1H, m), 5.35(1H, m), 4.70(1H, m), 4.63(1H, m), 4.30(1H, m), 4.11(1H, m), 4.01(1H, m), 3.72(1H, m), 2.84(1H, m), 2.2–4.0(8H, m)

EXAMPLE 112

2-Deoxy-2-[4-(pyridin-3-yl)carbonylpiperazin-1-yl]-1.4;3.6-dianhydro-D-glucitol 5-nitrate (Compound 119)

Compound 119 was obtained in a manner similar to Example 89 except that nicotinic acid was used in place of picolinic acid and Compound c obtained in Reference Example 3 was used in place of Compound b. The product was recrystallized from isopropyl alcohol/n-hexane system and dried to afford Compound 119 in good purity (yield: 30%).
Melting point: 136.0°–137.0° C.
MS (EI) m/z: 364 (M$^+$)
IR (KBr) cm$^{-1}$: 1633, 1586, 1440, 1278, 1095, 1009, 876, 853
NMR (CDCl$_3$) δ (ppm): 8.60–8.75(2H, m), 7.75(1H, d, J=7.7 Hz), 7.36(1H, m), 5.34(1H, m), 4.93(1H, m), 4.44(1H, m), 4.20(1H, m), 4.07(1H, m), 2.3–4.0 (11H, m)

EXAMPLE 113

5-Deoxy-5-[4-(1,2,3-thiadiazol-5-yl)carbonylpiperazin-1-yl]-1.4;3.6-dianhydro-L-iditol 2-nitrate hydrochloride (Compound 120)

Compound 120 was obtained (yield: 53%) in a manner similar to Example 89 except that 1,2,3-thiadiazole-5-carboxylic acid [J. Pharmaceutical Sci., 65, 304 (1976)] was used in place of picolinic acid and the stirring condition at 0° C. for an hour was changed to the stirring condition at room temperature for an hour.
Melting point: 128.0°–133.0° C.
MS (EI) m/z: 371 (M+)
IR (KBr) cm$^{-1}$: 1659, 1642, 1487, 1432, 1278, 1097, 856
NMR (DMSO-d$_6$) δ (ppm): 9.23(1H, s), 5.45(1H, m), 5.24 (1H, m), 4.85(1H, m), 2.8–4.7(13H, m)

EXAMPLE 114

5-Deoxy-5-[4-(1,2,3-thiadiazol-4-yl)carbonylpiperazin-1-yl]-1.4;3.6-dianhydro-L-iditol 2-nitrate hydrochloride (Compound 121)

Compound 121 was obtained (yield: 46%) in a manner similar to Example 89 except that 1,2,3-thiadiazole-4-carboxylic acid [J. Am. Chem. Soc., 77, 5359 (1955)] was used in place of picolinic acid and the stirring condition at 0° C. for an hour was changed to the stirring condition at room temperature for 3 hours.
Melting point: 118.0°–121.0° C.
MS (EI) m/z: 371 (M+)
IR (KBr) cm$^{-1}$: 1658, 1640, 1420, 1277, 971, 852, 750
NMR (DMSO-d$_6$) δ (ppm): 9.63(1H, s), 5.44(1H, m), 5.26 (1H, m), 4.84(1H, m), 2.9–4.7(13H, m)

EXAMPLE 115

5-Deoxy-5-[4-(2-aminothiazol-4-yl)carbonylpiperazin-1-yl]-1.4;3.6-dianhydro-L-iditol 2-nitrate hydrochloride (Compound 122)

Compound 122 was obtained (yield: 34%) in a manner similar to Example 89 except that 2-aminothiazole-4-carboxylic acid (EP-A No. 300400) was used in place of picolinic acid.
MS (FAB) m/z: 386 (M$^+$ +1)
IR (KBr) cm$^{-1}$: 1658, 1640, 1429, 1278, 849
NMR (DMSO-d$_6$) δ (ppm): 7.24(1H, s), 5.44(1H, m), 5.32 (1H, m), 4.85(1H, m), 2.9–5.3(13H, m)

Pharmaceutical Preparation 1 : Tablet

A tablet comprising the following components was prepared by a known method.

| Compound 80 | 50 mg |
|---|---|
| Lactose | 150 mg |
| Potato starch | 75 mg |
| Polyvinyl alcohol | 7.5 mg |
| Magnesium stearate | 2.5 mg |

Pharmaceutical Preparation 2 : Powder

A powder comprising the following components was prepared by a known method.

| Compound 80 | 50 mg |
|---|---|
| Lactose | 750 mg |

Pharmaceutical Preparation 3 : Syrup

A syrup comprising the following components was prepared by a known method.

| Compound 80 | 50 mg |
|---|---|
| Purified white sugar | 75 mg |
| Ethyl p-hydroxybenzoate | 100 mg |
| Propyl p-hydroxybenzoate | 25 mg |
| Strawberry flavour | 0.25 cc |

Water is added thereto until the total volume is 100 cc

Pharmaceutical Preparation 4 : Capsule

A capsule comprising the following components was prepared by a known method.

| Compound 80 | 50 mg |
|---|---|
| Lactose | 500 mg |
| Magnesium Stearate | 12.5 mg |

The components were blended and encapsulated into a gelatin capsule.

Pharmaceutical Preparation 5 : Injection

An injection comprising the following components was prepared by a known method.

| Compound 80 | 20 mg |
|---|---|
| Sodium Chloride | 45 mg |

Water is added thereto until the total volume is 5 ml (one ampule unit).

The water was previously distilled and sterilized in an autoclave.

TABLE 3

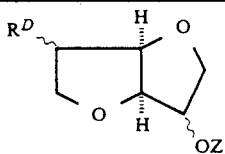

| Compound No. (Reference Example) | R$^D$~ | ~OZ |
|---|---|---|
| a (1) | HN⌒N— (piperazinyl) | ·····OH |
| b (2) | " | ·····ONO$_2$ |
| c (3) | " | ONO$_2$ |
| d (4) | HN⌒N (piperazinyl) | ·····ONO$_2$ |
| e (5) | HN⌒N— (with extra substitution) | " |

REFERENCE EXAMPLE 1

5-Deoxy-5-(piperazin-1-yl)-1.4;3.6-dianhydro-L-iditol (Compound a)

A mixture of 20.2 g (90.1 mmols) of 1.4;3.6-dianhydro-D-glucitol 5-methansulfonate (Japanese Published Unexamined Patent Application No. 58792/82 [U.S. Pat. No. 4,542,137 and EP-B No. 44927]), 84.8 g (984.4 mmols) of piperazine and 240 ml of n-butanol was heated under reflux for 36 hours. The mixture was concentrated under reduced pressure, and the residue was azeotropically evaporated with toluene several times to remove piperazine as much as possible. Thus, Compound a methanesulfonate was obtained as a crude product.

The crude product described above was purified by chromatography of DIAION SP 207 (manufactured by Mitsubishi Kasei Corporation) (eluent: water ~30% aqueous methanol solution). After azeotropic distillation with isopropyl alcohol, crystallization was performed with the residue from ethyl acetate to afford purified Compound a.

NMR (DMSO-d$_6$) δ (ppm): 5.35(1H, m), 4.50(1H, m), 4.19 (1H, m), 2.2–4.1(14H, m)

REFERENCE EXAMPLE 2

5-Deoxy-5-(piperazin-1-yl)-1.4;3.6-dianhydro-L-iditol 2-nitrate (Compound b)

To 37.8 g of the crude Compound a methanesulfonate obtained in Reference Example 1 was added 10.6 ml of water. Then, with cooling, 5.6 ml of conc. sulfuric acid was dropwise added to the mixture to obtain a solution (solution B).

A solution of 2.47 g (41.1 mmols) of urea in 55.6 ml of conc. sulfuric acid was dropwise added to 37 ml of fumed nitric acid (86%) at −15° C. with stirring. Then, solution B was dropwise added thereto at −15° C. over 30 minutes to an hour. The mixture was stirred at the same temperature for further 2 hours. The reaction mixture was gradually poured into 300 ml of water with stirring. With cooling, a mixture of 120 g (3.00 mols) of sodium hydroxide and 370 ml of water was gradually added to the system for neutralization followed by extraction of the solution with chloroform 5 to 10 times. The chloroform layer was dried over anhydrous sodium sulfate. The solvent was evaporated under reduced pressure, and the residue was purified by silica gel column chromatography (eluent: chloroform/methanol = 10/1–0/1) to afford 8.9 g (yield: 38%) of Compound b.

IR (KBr) cm$^{-1}$: 3420(br), 1634, 1278

REFERENCE EXAMPLE 3

2-Deoxy-2-(piperazin-1-yl)-1.4;3.6-dianhydro-D-glucitol 5-nitrate (Compound c)

To a mixture of 4.36 g (23.2 mmols) of 5-O-acetyl-1.4;3.6-dianhydro-D-glucitol [Synthesis, 174 (1987)], 15 ml of pyridine and 0.85 g (6.96 mmols) of dimethylaminopyridine was dropwise added 2.7 ml (34.9 mmols) of methanesulfonyl chloride with stirring under ice cooling. The mixture was stirred at room temperature for further an hour. The mixture was concentrated under reduced pressure, and then water was added to the residue followed by extraction of the solution with methylene chloride. The methylene chloride layer was washed twice with a 10% aqueous hydrochloric acid solution, and then sequentially with aqueous saturated sodium bicarbonate solution and an aqueous saturated sodium chloride solution, and then dried over anhydrous sodium sulfate. The solvent was evaporated under reduced pressure to afford 5.78 g (yield: 94%) of 5-0-acetyl-1.4;3.6-dianhydro-D-glucitol 2-methanesulfonate.

NMR (CDCl$_3$) δ (ppm): 5.03–5.30(2H, m), 4.87(1H, m), 4.66(1H, m), 3.61–4.27(4H, m), 3.07(3H, s), 2.12 (3H, s)

A mixture of 6.65 g (25.0 mmols) of the compound described above, 1.04 g (7.50 mmols) of potassium carbonate, 30 ml of methanol and 30 ml of chloroform was stirred at room temperature for 3 hours. After the reaction, insoluble matters were filtered off and the filtrate was concentrated under reduced pressure. The residue was recrystallized from chloroform to afford 2.90 g (yield: 52%) of 1.4;3.6-dianhydro-D-glucitol 2-methanesulfonate.

NMR (DMSO-d$_6$) δ (ppm): 5.07(1H, m), 4.57(1H, m), 4.47 (1H, m), 4.15(1H, m), 4.03(1H, m), 3.90(3H, m), 3.76(1H, m), 3.35(1H, m), 3.27(3H, s)

Thereafter, Compound c was obtained (yield: 35%) in a manner similar to Reference Examples 1 and 2 except that the compound described above was used in place of 1.4;3.6-dianhydro-D-glucitol 5-methanesulfonate in Reference Example 1.

NMR (CDCl$_3$) δ (ppm): 5.32(1H, m), 4.90(1H, m), 4.43 (1H, m), 2.2–4.3(14H, m)

REFERENCE EXAMPLE 4

5-Deoxy-5-(piperazin-1-yl)-1.4;3.6-dianhydro-D-glucitol 2-nitrate (Compound d)

With stirring a mixture of 20.0 g (89.3 mmols) of 1.4;3.6-dianhydro-D-glucitol 2-methanesulfonate obtained in Reference Example 3, 46.8 g (178.4 mmols) of triphenylphosphine, 21.8 g (178.5 mmols) of benzoic acid and 1.3 liter of absolute tetrahydrofuran at room temperature, 100 ml of a solution of 27.5 ml (178.4 mmols) of diethyl azodicarboxylate in absolute tetrahydrofuran was dropwise added to the solution. The mixture was stirred at room temperature overnight. The mixture was concentrated under reduced pressure, and the residue was purified by silica gel column chromatography (eluent: chloroform) to afford 20.0 g (yield: 68%) of 5-O-benzoyl-1.4;3.6-dianhydro-L-iditol 2-methanesulfonate.

NMR (CDCl$_3$) δ (ppm): 8.03(2H, d, J=8.0 Hz), 7.60(1H, dd, J=7.5, 7.5 Hz), 7.46(2H, dd, J=8.0, 7.5 Hz), 5.47(1H, m), 5.18(1H, m), 4.90(1H, m), 4.84(1H, m), 4.16(1H, m), 4.08(2H, m), 4.03(1H, m), 3.10 (3H, s)

A mixture of 30.0 g (91.5 mmols) of the compound described above, 1.83 g (45.7 mmols) of sodium hydroxide and 1 liter of methanol was stirred at room temperature for 2 hours. After the reaction, an aqueous dil. hydrochloric acid was added to the mixture to neutralize the mixture. The solvent was evaporated under reduced pressure, and the residue was purified by silica gel column chromatography (eluent: chloroform/methanol =25/1) and then tritylated with diethyl ether to afford 19.9 g (yield: 97%) of 1.4;3.6-dianhydro-L-iditol 2-methanesulfonate.

NMR (DMSO-d$_6$/CDCl$_3$) δ (ppm): 5.08(1H, m), 4.83(1H, m), 4.60(1H, m), 4.30(1H, m), 4.07(1H, m), 3.86-3.98 (2H, m), 3.81(1H, m), 3.09(3H, s)

Thereafter, Compound d was obtained (yield: 25%) in a manner similar to Reference Examples 1 and 2 except that the compound described above was used in place of 1.4;3.6-dianhydro-D-glucitol 5-methanesulfonate in Reference Example 1 and the reaction under reflux for 36 hours was changed to a reaction at 160° C. in a sealed tube for 22 hours.

NMR (CDCl$_3$) 6 (ppm): 5.33(1H, m), 4.50-4.75(2H, m), 2.2-4.5(14H, m)

REFERENCE EXAMPLE 5

5-Deoxy-5-(homopiperazin-1-yl)-1.4;3.6-dianhydro-L-iditol 2-nitrate (Compound e)

Compound e was obtained (yield: 11%) in a manner similar to Reference Examples 1 and 2 except that homopiperazine was used in place of piperazine in Reference Example 1 and the period for heating under reflux was changed from 36 hours to 7 days.

REFERENCE EXAMPLE 6

1-Chloro-3-phenylthiopropane

A mixture of 54.0 g (490 mmols) of thiophenol, 160.0 g (1016 mmols) of 1-bromo-3-chloropropane and 250 ml of a 2.2 M aqueous sodium hydroxide solution was heated under reflux for 30 hours. After cooling, the reaction mixture was extracted with methylene chloride. The methylene chloride layer was washed with an aqueous dil. sodium hydroxide solution and then with water and dried over anhydrous sodium sulfate. The solvent was evaporated under reduced pressure, and the residue was distilled under reduced pressure (138 -140° C./13 mmHg) to afford 51.9 g (yield: 57%) of the title compound.

NMR (CDCl$_3$) δ (ppm): 7.0-7.7(5H, m), 3.60(2H, t, J=6.0 Hz), 3.03(2H, t, J=7.0 Hz), 2.03(2H, m)

REFERENCE EXAMPLE 7

1-Chloro-3-(4-methoxyphenylthio)propane

With stirring at room temperature, 5.6 g (39.9 mmols) of 4-methoxythiophenol was added by small portions to 20 ml of a solution of 0.98 g (40.8 mmols) of sodium hydride in dimethylformamide. The solution was dropwise added to 40 ml of a solution of 6.3 g (40.0 mmols) of 1-bromo-3-chloropropane in dimethylformamide with stirring under ice cooling. The mixture was stirred under ice cooling for further an hour. After the reaction, an aqueous saturated sodium bicarbonate solution was added to the mixture followed by extraction of the solution with ethyl acetate 3 times. The ethyl acetate layer was dried over anhydrous sodium sulfate. The solvent was evaporated under reduced pressure, and the residue was purified by silica gel column chromatography (eluent: chloroform) to afford 7.8 g (yield: 90%) of the title compound.

NMR (CDCl$_3$) δ (ppm): 7.35(2H, d, J=8.9 Hz), 6.84(2H, d, J=8.9 Hz), 3.78(3H, s ), 3.63(2H, t, J=6.4 Hz), 2.95(2H, t, J=6.9 Hz), 1.99(2H, m)

REFERENCE EXAMPLE 8

1-Chloro-3-(2-ethoxycarbonylphenylthio)propane

With stirring at room temperature, 15.4 g (99.9 mmols) of thiosalicylic acid was added by small portions to 50 ml of a solution of 2.44 g (101.7 mmols) of sodium hydride in dimethylformamide. The solution was dropwise added to 100 ml of a solution of 15.7 g (99.7 mmols) of 1-bromo-3-chloropropane in dimethylformamide with stirring under ice cooling. The mixture was stirred under ice cooling for further an hour and a half. After the reaction, an aqueous saturated sodium bicarbonate solution was added to the mixture followed by extraction of the solution with ethyl acetate 10 times. The ethyl acetate layer was dried over anhydrous sodium sulfate. The solvent was evaporated under reduced pressure, and the residue was purified by silica gel column chromatography (eluent: chloroform/methanol =50/1) to afford 9.0 g (yield: 39%) of 1-chloro-3-(2-hydroxycarbonylphenylthio)propane.

NMR (CDCl$_3$) δ (ppm): 8.10(1H, m), 7.05-7.60(3H, m), 3.71(2H, t, J=6.3 Hz), 3.11(2H, t, J=7.0 Hz), 2.18 (2H, m)

A mixture of 2.13 g (9.23 mmols) of the compound described above, 100 ml of ethanol and 1 ml of conc. sulfuric acid was heated under reflux for 18 hours. After cooling to 0° C., the mixture was neutralized with a 2 normal aqueous sodium hydroxide solution. The solvent was evaporated under reduced pressure, and then water was added to the residue followed by extraction of the solution with chloroform. The chloroform layer was washed with an aqueous saturated sodium bicarbonate solution and then with an aqueous saturated sodium chloride solution and dried over anhydrous sodium sulfate. The solvent was evaporated under reduced pressure, and the residue was dried to afford 2.09 g (yield: 87%) of the title compound.

NMR (CDCl$_3$) δ (ppm): 7.94(1H, m), 7.00-7.60(3H, m), 4.39(2H, q, J=7.1 Hz), 3.70(2H, t, J=6.3 Hz), 3.10 (2H, t, J=7.0 Hz), 2.17(2H, m), 1.40(3H, t, J=7.1 Hz)

REFERENCE EXAMPLE 9

1-Chloro-3-(4-ethoxycarbonylmethylphenylthio)propane

A mixture of 54.7 g (228 mmols) of sodium sulfide nonahydrate, 7.0 g (218 mmols) of sulfur and 60 ml of water was heated until sodium sulfide nonahydrate was dissolved. A solution of 8.83 g of sodium hydroxide in 24 ml of water was added thereto and the mixture was cooled to 5° C. (solution C).

Under ice cooling, 40.0 ml of conc. hydrochloric acid was added to a mixture of 30.3 g (200 mmols) of 4- aminophenylacetic acid and 100 ml of water. Then, a solution of 13.8 g (200 mmols) of sodium sulfite was dropwise added thereto with stirring while adding ice so that the inner temperature was not higher than 5° C. Furthermore, solution C was added thereto so that the inner temperature was not higher than 5° C. Then the temperature was slowly raised to room temperature with stirring and 35.9 ml of conc. hydrochloric acid was added to the mixture followed by filtration. To the solid taken by filtration was added 1500 ml of an aqueous 10% sodium carbonate solution. The mixture was stirred at 80° C. and insoluble matters were filtered off. Conc. hydrochloric acid was added to the filtrate to render acidic. The precipitated crystals were taken out by filtration and dried to afford 18.3 g of crude 4,4'-dithiobis(phenylacetic acid).

A mixture of 3.34 g of the crude 4,4'-dithiobis(phenylacetic acid), 350 ml of ethanol and 7 ml of conc. sulfuric acid was heated under reflux for 3 hours. After cooling to 0° C., the mixture was neutralized with a 2 normal aqueous sodium hydroxide solution. The solvent was evaporated under reduced pressure, and then water was added to the residue followed by extraction of the solution with chloroform. The chloroform layer was washed with an aqueous saturated sodium bicarbonate solution and then with an aqueous saturated sodium chloride solution and dried over anhydrous sodium sulfate. The solvent was evaporated under reduced pressure, and the residue was dried to afford 2.18 g of 4,4'-dithiobis(diethyl phenylacetate).

NMR (CDCl$_3$) δ (ppm): 7.45(4H, d, J=8.6 Hz), 7.20(4H, d, J=8.6 Hz), 4.14(4H, q, J=7.2 Hz), 3.57(4H, s), 1.24 (6H, t, J=7.2 Hz)

With stirring under ice cooling, 0.88 g (22.47 mmols) of sodium borohydride was added by small portions to 20 ml of a solution of 2.18 g (5.58 mmols) of the compound described above in dimethylformamide. The mixture was stirred under ice cooling for further 30 minutes. The solution was dropwise added to 20 ml of a solution of 1.79 g (11.37 mmols) of 1-bromo-3-chloropropane in dimethylformamide with stirring under ice cooling. The mixture was stirred for further 50 minutes under ice cooling. After the reaction, an aqueous saturated sodium bicarbonate solution was added to the mixture followed by extraction of the solution with ethyl acetate 3 times. The ethyl acetate layer was dried over anhydrous sodium sulfate. The solvent was evaporated under reduced pressure, and the residue was purified by silica gel column chromatography (eluent: chloroform) to afford 2.0 g (yield: 66%) of the title compound.

NMR (CDCl$_3$) δ (ppm): 7.32(2H, d, J=8.6 Hz), 7.19(2H, d, J=8.6 Hz), 4.15(2H, q, J=7.1 Hz), 3.65(2H, t, J=6.4 Hz), 3.57(2H, s), 3.05(2H, t, J=6.9 Hz), 2.06(2H, m), 1.25(3H, t, J=7.0 Hz)

REFERENCE EXAMPLE 10

1-(Benzotriazol-1-yl)-3-chloropropane (Compound f) and 1-(benzotriazol-2-yl)-3-chloropropane (Compound g)

With stirring at room temperature, 10.0 g (83.9 mmols) of benzotriazole was added by small portions to 40 ml of a solution of 2.01 g (83.8 mmols) of sodium hydride in dimethylformamide. The solution was dropwise added to 80 ml of a solution of 13.2 g (-83.8 mmols) of 1-bromo-3-chloropropane in dimethylformamide with stirring under ice cooling. The mixture was stirred under ice cooling for further 4 hours. After the reaction, an aqueous saturated sodium bicarbonate solution was added to the mixture followed by extraction of the solution with ethyl acetate 3 times. The ethyl acetate layer was dried over anhydrous sodium sulfate. The solvent was evaporated under reduced pressure, and the residue was purified by silica gel column chromatography (eluent: hexane/ethyl acetate =3/1) to afford 7.48 g (yield: 46%) of Compound g from the first fraction and 6.16 g (yield: 38%) of Compound f from the next fraction. Compound f:

NMR (CDCl$_3$) δ (ppm): 8.06(1H, m), 7.20–7.70(3H, m), 4.82(2H, t, J=6.5 Hz), 3.54(2H, t, J=6.0 Hz), 2.50 (2H, m)

Compound g:

NMR (CDCl$_3$) δ (ppm): 7.65–7.95(2H, m), 7.15–7.45(2H, m), 4.91(2H, t, J=6.5 Hz), 3.60(2H, t, J=6.3 Hz), 2.57(2H, m)

REFERENCE EXAMPLE 11

1-Chloro-3-(indazol-1-yl)propane (Compound h) and 1-chloro-3-(indazol-2-yl)propane (Compound i)

With stirring at room temperature, 5.00 g (42.3 mmols) of indazole was added by small portions to 25 ml of a solution of 1.03 g (42.9 mmols) of sodium hydride in dimethylformamide. The solution was dropwise added to 50 ml of a solution of 6.67 g (42.4 mmols) of 1-bromo-3-chloropropane in dimethylformamide with stirring under ice cooling. The mixture was stirred under ice cooling for further an hour and a half. After the reaction, an aqueous saturated sodium bicarbonate solution was added to the mixture followed by extraction of the solution with ethyl acetate 3 times. The ethyl acetate layer was dried over anhydrous sodium sulfate. The solvent was evaporated under reduced pressure, and the residue was purified by silica gel column chromatography (eluent: hexane/ethyl acetate =3/1) to afford 4.94 g (yield: 60%) of Compound h from the first fraction and 1.93 g (yield: 23%) of Compound i from the next fraction.

Compound h:

NMR (CDCl$_3$) δ (ppm): 8.01(1H, s), 7.73(1H, d, J=7.9 Hz), 6.95–7.60(3H, m), 4.56(2H, t, J=6.4 Hz), 3.50 (2H, t, J=6.2 Hz), 2.40(2H, m)

Compound i:

NMR (CDCl$_3$) δ (ppm): 7.96(1H, s), 7.53–7.77(2H, m), 6.93–7.38(2H, m), 4.62(2H, t, J=6.4 Hz), 3.47(2H, t, J=6.0 Hz), 2.47(2H, m)

REFERENCE EXAMPLE 12

3-Ethoxycarbonylmethylindole

A mixture of 5.0 g (28.5 mmols) of indole-3acetic acid, 250 ml of ethanol and 5 ml of conc. sulfuric acid was heated under reflux for 2 hours. After cooling to 0° C., the mixture was neutralized with a 2 normal aqueous sodium hydroxide solution. The solvent was evaporated under reduced pressure, and then water was added to the residue followed by extraction of the solution with chloroform. The chloroform layer was washed with an aqueous saturated sodium chloride solution and dried over anhydrous sodium sulfate. The solvent was evaporated under reduced pressure, and the residue was dried to afford 5.2 g (yield: 90%) of the title compound.

NMR (CDCl$_3$) δ (ppm): 8.10(1H, brs), 7.0–7.7(4H, m), 6.97(1H, s), 4.15(2H, q, J=7.1 Hz), 3.73(2H, s), 1.23(3H, t, J=7.1 Hz)

REFERENCE EXAMPLE 13

4,5-Bis(ethoxycarbonyl)imidazole

A mixture of 4.0 g (25.6 mmols) of imidazole-4,5-dicarboxylic acid, 600 ml of ethanol and 16 ml of conc. sulfuric acid was heated under reflux for 7 hours. After cooling to 0° C., the mixture was neutralized with a 2 normal aqueous sodium hydroxide solution. The solvent was evaporated under reduced pressure, and then water was added to the residue followed by extraction of the solution with chloroform. The chloroform layer was washed with an aqueous saturated sodium bicarbonate solution and then with an aqueous saturated sodium chloride solution and dried over anhydrous sodium sulfate. The solvent was evaporated under reduced pressure, and the residue was dried to afford 2.5 g (yield: 46%) of the title compound.

NMR (CDCl$_3$) δ (ppm): 7.83(1H, s), 7.26(1H, s), 4.41 (4H, q, J=7.2 Hz), 1.38(6H, t, J=7.2 Hz)

REFERENCE EXAMPLE 14

1-Methanesulfonyl-2-(2-methanesulfonyloxyethyl)benzimidazole

A mixture of 3.17 g (29.3 mmols) of o-phenylenediamine, 3.75 g (36.0 mmols) of 3-methoxypropionic acid [J. Am. Chem. Soc., 70, 1004 (1948)] and 32 ml of a 4 normal aqueous hydrochloric acid solution was heated under reflux for 14 hours. After cooling, the mixture was neutralized with a 28-30% aqueous ammonia solution. The mixture was concentrated under reduced pressure, and the residue was purified by silica gel column chromatography (eluent: chloroform/methanol =20/1) to afford 4.74 g (yield: 92%) of 2-(2-methoxyethyl)benzimidazole.

NMR (CDCl$_3$) δ (ppm): 7.35-7.60(2H, m), 7.05-7.30(2H, m), 3.79(2H, t, J=5.7 Hz), 3.41(3H, s), 3.19(2H, t, J=5.7 Hz)

A mixture of 4.74 g (26.9 mmols) of the compound described above and 100 ml of a 47-49% aqueous hydrobromic acid solution was heated under reflux for 50 minutes. After cooling, the mixture was neutralized with a 2 normal aqueous sodium hydroxide solution. The mixture was concentrated under reduced pressure, and the residue was purified by silica gel column chromatography (eluent: chloroform/methanol =10/1) to afford 3.18 g (yield: 73%) of 2-(2-hydroxyethyl)benzimidazole.

NMR (CDCl$_3$-CD$_3$OD) δ (ppm): 7.30-7.65(2H, m), 7.00-7.30 (2H, m), 4.01(2H, t, J=5.9 Hz), 3.09(2H, t, J=5.9 Hz)

With stirring under ice cooling, a 1.46 ml (18.48 mmols) of methanesulfonyl chloride was dropwise added to a mixture of 1.50 g (9.25 mmols) of the compound described above and 15 ml of pyridine. The mixture was stirred at 0° C. for further an hour and a half. Then, a 4 normal aqueous hydrochloric acid solution was added to the mixture followed by extraction of the solution with chloroform. The chloroform layer was dried over anhydrous sodium sulfate. The solvent was evaporated under reduced pressure, and the residue was purified by silica gel column chromatography (eluent: chloroform/methanol =50/1) to afford 1.32 g (yield: 45%) of the title compound.

NMR (CDCl$_3$) δ (ppm): 7.55-7.95(2H, m), 7.25-7.50(2H, m), 4.81(2H, t, J=6.3 Hz), 3.63(2H, t, J=6.3 Hz), 3.29(3H, s), 3.05(3H, s)

REFERENCE EXAMPLE 15 o-[N,N-Bis(chloroethyl)amino]anisole

A mixture of 7.38 g (59.9 mmols) of o-anisidine, 10 ml (202.3 mmols) of ethylene oxide and 150 ml of a solvent mixture of acetic acid and water (9/1) was stirred at room temperature for 40 hours. The mixture was concentrated under reduced pressure, and the residue was purified by silica gel column chromatography (eluent: chloroform/methanol =30/1) to afford o-[N,N-bis(hydroxyethyl)amino]anisole.

NMR (CDCl$_3$) δ (ppm): 6.75-7.30(4H, m), 3.86(3H, s), 3.51(4H, t, J=5.0 Hz), 3.19(4H, t, J=5.0 Hz)

To the compound described above were added 5.35 g (126.2 mmols) of lithium chloride, 9.6 ml (118.7 mmols) of pyridine and 100 ml of dimethylformamide. With stirring at 0° C., 9.3 ml (120.2 mmols) of methanesulfonyl chloride was dropwise added to the mixture, and the mixture was stirred at room temperature for further 60 hours. The mixture was concentrated under reduced pressure, and the residue was purified by silica gel column chromatography (eluent: hexane/ethyl acetate =4/1) to afford 5.47 g (yield: 37%) of the title compound.

NMR (CDCl$_3$) δ (ppm): 6.70-7.25(4H, m), 3.84(3H, s), 3.50(8H, s)

REFERENCE EXAMPLE 16

4-Cyano-5-methyl-4-(3,4,5-trimethoxyphenyl)hexyl chloride

With stirring under ice cooling, 20.25 g (97.7 mmols) of 3,4,5-trimethoxyphenylacetonitrile was added by small portions to 50 ml of a solution of 2.45 g (102.1 mmols) of sodium hydride in dimethylformamide. The solution was dropwise added to 100 ml of a solution of 12.45 g (101.2 mmols) of 2-bromopropane in dimethylformamide with stirring under ice cooling. The mixture was stirred under ice cooling for further 3 hours. After the reaction, an aqueous saturated sodium bicarbonate solution was added to the mixture followed by extraction of the solution with ethyl acetate. The ethyl acetate layer was dried over anhydrous sodium sulfate. The solvent was evaporated under reduced pressure, and the residue was purified by silica gel column chromatography (eluent: hexane/ethyl acetate =4/1) to afford 13.2 g (yield: 54%) of 3-methyl-2-(3,4,5-trimethoxyphenyl)butyronitrile.

NMR (CDCl$_3$) δ (ppm): 6.49(2H, s), 3.87(6H, s), 3.84 (3H, s), 3.57(1H, d, J=6.4 Hz), 2.13(1H, m), 1.06 (6H, d, J=6.6 Hz)

With stirring, a mixture of 9.71 g (38.9 mmols) of the compound described above and 30 ml of toluene at 40° C., 10.08 g (179.7 mmols) of potassium hydroxide, 100 mg (0.27 mmols) of tetrabutyl ammonium iodide and 30 ml of a solution of 6.48 g (41.2 mmols) of 1-bromo-3-chloropropane in toluene were successively added thereto. The mixture was heated at 90° C. for 2 hours with stirring. The mixture was concentrated under reduced pressure, and the residue was purified by silica gel column chromatography (eluent: hexane/ethyl acetate =5/1) to afford 7.10 g (yield: 56%) of the title compound.

NMR (CDCl$_3$) δ (ppm): 6.58(2H, s), 3.87(6H, s), 3.86 (3H, s), 3.51(2H, t, J=5.8 Hz), 1.30-2.30(5H, m), 1.21(3H, d, J=6.8 Hz), 0.84(3H, d, J=6.8 Hz)

REFERENCE EXAMPLE 17

1-(3-Chloropropyl)-7-hydroxy-4,6-dimethylbenzimidazole and
1-(3-chloropropyl)-4-hydroxy-5,7-dimethylbenzimidazole A mixture of 2.50 g (10.3 mmols) of 3-benzyloxy-4,6-dimethyl-1,2-phenylenediamine [J. Med. Chem., 30, 2216 (1987)] and 20 ml of formic acid was heated under reflux for 30 minutes. The mixture was concentrated under reduced pressure, and then an aqueous saturated sodium bicarbonate solution was added to the residue followed by extraction of the solution with chloroform. The chloroform layer was dried over anhydrous sodium sulfate. The solvent was evaporated under reduced pressure, and the residue was purified by silica gel column chromatography (eluent: chloroform/methanol =40/1) to afford 1.59 g (yield: 61%) of 7-benzyloxy-4,6-dimethylbenzimidazole.

NMR (CDCl$_3$) δ (ppm): 7.84(1H, s), 7.10–7.60(5H, m), 6.86(1H, s), 5.28(2H, s), 2.47(3H, s), 2.33(3H, s)

With stirring under ice cooling, 1.57 g (6.26 mmols) of the compound described above was added by small portions to 50 ml of a solution of 0.15 g (6.25 mmols) of sodium hydride in dimethylformamide. The solution was dropwise added to 100 ml of a solution of 0.99 g (6.29 mmols) of 1-bromo-3-chloropropane in dimethylformamide with stirring under ice cooling. The mixture was stirred at room temperature overnight. After the reaction, an aqueous saturated sodium bicarbonate solution was added to the mixture followed by extraction of the solution with ethyl acetate. The ethyl acetate layer was dried over anhydrous sodium sulfate. The solvent was evaporated under reduced pressure, and the residue was purified by silica gel column chromatography (eluent: chloroform/methanol =50/1) to afford 1.76 g (yield: 86%) of a mixture of 7-benzyloxy-1-(3-chloropropyl)-4,6-dimethylbenzimidazole and 4-benzyloxy-1-(3-chloropropyl)-5,7-dimethylbenzimidazole.

NMR (CDCl$_3$) δ (ppm): 7.79 and 7.74(1H, s), 7.10–7.60 (5H, m), 6.90 and 6.78(1H, s), 5.60 and 4.96(2H, s), 4.50 and 4.26(2H, t, J=6.7 Hz), 3.50 and 3.24 (2H, t, J=6.0 Hz), 1.90–2.70(8H, m)

A mixture of 1.76 g (5.35 mmols) of the mixture described above and 45 ml of a 5 normal aqueous hydrochloric acid solution was heated at 80° C. for 15 minutes with stirring. After cooling, the mixture was neutralized with an aqueous saturated sodium bicarbonate solution followed by extraction of the solution with chloroform. The chloroform layer was dried over anhydrous sodium sulfate, the solvent was evaporated under reduced pressure, and the residue was purified by silica gel column chromatography (eluent: chloroform/methanol =30/1) to afford 1.00 g (yield: 78%) of the title compound mixture.

NMR (CDCl$_3$) δ (ppm): 7.74 and 7.71(1H, s), 7.32 and 7.28(1H, s), 6.79(1H, brs), 4.25–4.70(2H, m), 3.25–3.60(2H, m), 1.90–2.65(8H, m)

REFERENCE EXAMPLE 18

1-Bis(chloroethyl)amino-3-phenylthiopropane

A mixture of 8.30 g (44.5 mmols) of 1-chloro-3-phenylthiopropane, 100 ml of diethanolamine, 13.3 g (88.7 mmols) of sodium iodide and 250 ml of dioxan was heated under reflux for 15 hours. The mixture was concentrated under reduced pressure, and an aqueous saturated sodium bicarbonate solution was added to the mixture followed by extraction of the solution with chloroform 5 times. The chloroform layer was drided over anhydrous sodium sulfate. The solvent was evaporated under reduced pressure, and the residue was purified by silica gel column chromatography (eluent: chloroform/methanol =25/1) to afford 6.46 g (yield: 57%) of 1-bis(hydroxyethyl)amino-3-phenylthiopropane.

NMR (CDCl$_3$) δ (ppm): 6.9–7.6(5H, m), 3.61(4H, t, J=5.4 Hz), 2.98(2H, t, J=6.9 Hz), 2.20–2.85(6H, m), 1.80(2H, m)

With stirring a mixture of 6.46 g (25.4 mmols) of the compound described above, 2.15 g (50.8 mmols) of lithium chloride, 4.02 g (50.8 mmols) of pyridine and 160 ml of dimethylformamide at 0° C., 5.63 g (50.8 mmols) of methanesulfonyl chloride was dropwise added thereto. The mixture was stirred at room temperature for further 50 hours. The mixture was concentrated under reduced pressure, and then an aqueous saturated sodium bicarbonate solution was added to the mixture followed by extraction of the solution with chloroform. The chloroform layer was dried over anhydrous sodium sulfate. The solvent was evaporated under reduced pressure, and the residue was purified by silica gel column chromatography (eluent: hexane/ethyl acetate =8/1) to afford 3.82 g (yield: 44%) of the title compound.

NMR (CDCl$_3$) δ (ppm): 6.9–7.6(5H, m), 3.50(4H, t, J=

What is claimed is:

1. A hexitol derivative represented by the formula (I)

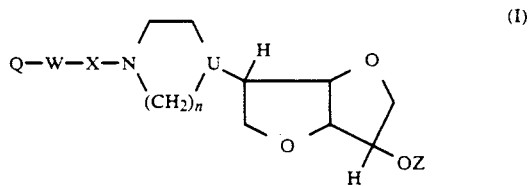

wherein

Q represents a formula selected from the group consisting of

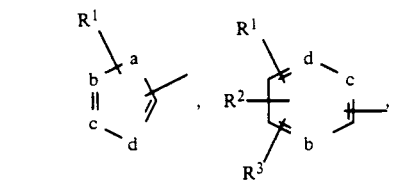

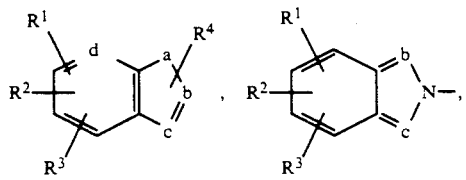

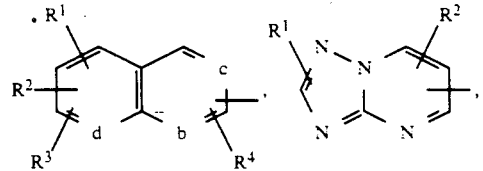

-continued

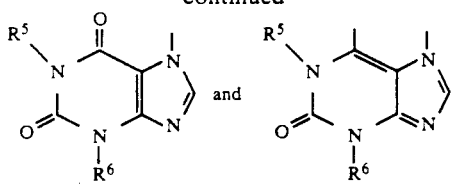

and wherein
a represents NH, O or S;
each of b, c and d independently represents CH or N;
each of $R^1$, $R^2$, $R^3$ and $R^4$ independently represents hydrogen, lower alkyl, trifluoromethyl, phenyl, naphthyl lower alkanoyloxy, amino, lower alkylamino, lower alkanoylamino, lower alkanoyl, benzoyl, naphthoyl, halogen, nitro, $(CH_2)_mOR^7$, $(CH_2)_mSR^7$, $(CH_2)_mCO_2R^7$ where $R^7$ represents hydrogen or lower alkyl and m represents an integer of 0 to 3;
each of $R^5$ and $R^6$ independently represents hydrogen or lower alkyl;
U represents >N— or

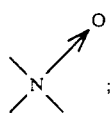

W represents a single bond, —O— or —S—
X represents

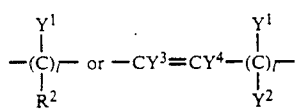

wherein each of $Y^1$ and $Y^2$ independently represents hydrogen, lower alkyl, hydroxyl, lower alkanoyloxy, nitrile or phenyl; or $Y^1$ and $Y^2$ are combined together to form oxygen; each of $Y^3$ and $Y^4$ independently represents hydrogen or lower alkyl; and l is an integer of 0 to 6, and where l is an integer of 2 to 6, each

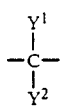

°may be the same or different;
Z represents hydrogen or nitro; and
n is 2 or 3;
or a pharmaceutically acceptable salt thereof.

2. A compound according to claim 1, wherein U is >N—.

3. A compound according to claim 2, wherein Q is

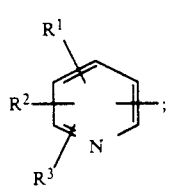

W is single bond; and X is

4. A compound according to claim 3, wherein each of $R^1$, $R^2$ and $R^3$ independently represents hydrogen, methyl, hydroxyl, chlorine or bromine.

5. A compound according to claim 4, which is selected from the group consisting of 5-deoxy-5-[4-(pyridin-3-yl)carbonylpiperazin-1-yl]-1.4;3.6-dianhydro-L-iditol 2nitrate, and hydrochloride thereof.

6. A compound according to claim 2, wherein Q is

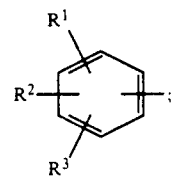

W is single bond; and X

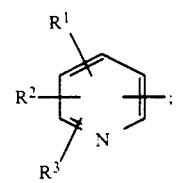

7. A compound according to claim 6, wherein each of $R^1$, $R^2$ and $R^3$ independently represents hydrogen or methoxy.

8. A compound according to claim 2, wherein Q is

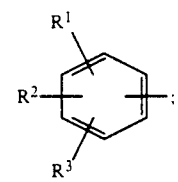

W is —S—; and X is —(CH$_2$)$_l$— where l is 2 to 4.

9. A compound according to claim 8, wherein each of $R^1$, $R^2$ and $R^3$ independently represents hydrogen, methoxy, chlorine, ethoxycarbonylmethyl, carboxymethyl or ethoxycarbonyl.

10. A compound according to claim 2, wherein Q is

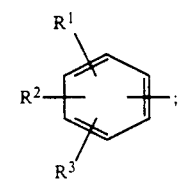

W is —O—; and X is —(CH$_2$)$_l$— where l is 2 or 3.

11. A compound according to claim 10, wherein each of $R^1$, $R^2$ and $R^3$ independently represents hydrogen, methyl or methoxy.

12. A compound according to claim 2, wherein Q is

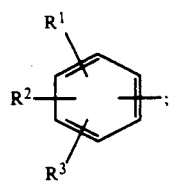

W is single bond; and X is

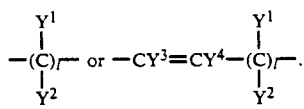

13. A compound according to claim 2, wherein Q is

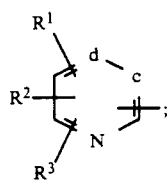

W is sulfur; and X is —(CH$_2$)$_3$—.

14. A compound according to claim 2, wherein Q is

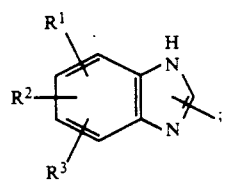

W is single bond; and X is —(CH$_2$)$_l$— where l is 0 to 3.

15. A compound according to claim 2, wherein Q is

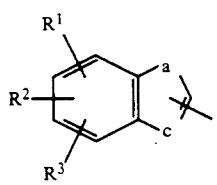

where a is NH or S; c is N or CH; W is single bond; and X is —(CH$_2$)$_l$— where l is 0 to 3.

16. A compound according to claim 2, wherein Q is

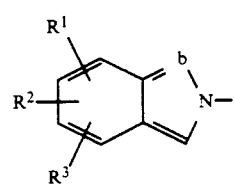

where b represents —CH or N; W is single bond; and X is —(CH$_2$)$_3$—.

17. A compound according to claim 2, wherein Q is

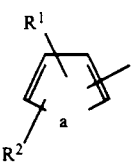

where a is O or S; W is single bond; and X is

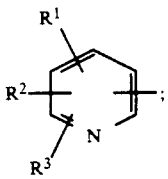

18. A compound according to claim 2, wherein Q is

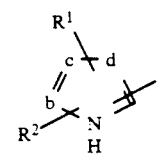

where b, c and d are CH or N; W is single bond; and X is —(CH$_2$)$_l$— where l is 0 to 3.

19. A compound according to claim 2, wherein Q is

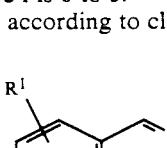

where b, c and d are CH or N; W is single bond; and X is —(CH$_2$)$_l$— where l is 0.

20. A compound according to claim 1, which is represented by formula (Ia):

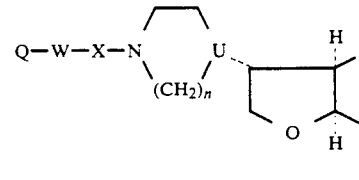

(Ia)

wherein Q, U, W, X, Z and n have the same significances as defined in claim 1.

21. A compound according to claim 1, which is represented by formula (Ib):

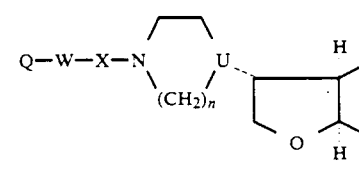

(Ib)

wherein Q, U, W, X, Z and n have the same significances as defined in claim 1.

22. A compound according to claim 1, which is represented by formula (Ic):

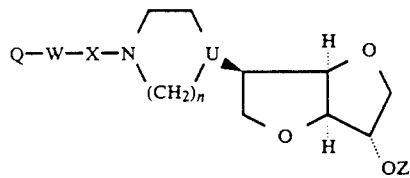

wherein Q, U, W, X, Z and n have the same significances as defined in claim 1.

23. A compound according to claim 1, which is represented by formula (Id):

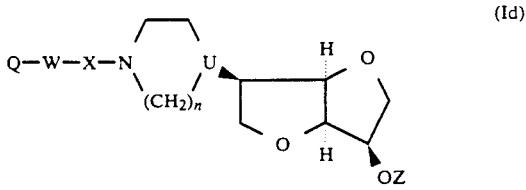

wherein Q, U, W, X, Z and n have the same significances as defined in claim 1.

24. A compound according to claim 1, wherein said salt is selected from the group consisting of acid addition salt, metal salt, ammonium salt, organic amino addition salt and amino acid addition salt.

25. A coronary vasodilative composition which comprises a pharmaceutically acceptable carrier and as active ingredient, an effective amount of the compound as defined by claim 1.

26. The coronary vasodilative composition according to claim 1, wherein the effective amount is a dosage of 1 to 50 mg/kg/day.

* * * * *

UNITED STATES PATENT AND TRADEMARK OFFICE
CERTIFICATE OF CORRECTION

PATENT NO. : 5,053,408

DATED : October 1, 1991

INVENTOR(S) : FUMIO SUZUKI, ET AL.

Page 1 of 12

It is certified that error appears in the above-identified patent and that said Letters Patent is hereby corrected as shown below:

On the title page:

Item: [56] REFERENCES CITED

Insert:   --         U.S. PATENT DOCUMENTS
    4,363,805   12/82     Klessing et al. ..... 424/230--.

Under PUBLICATIONS, insert:
    --The Merck Index 10th Edition (1983) p. 823--.

IN [57] ABSTRACT

In Column 1,

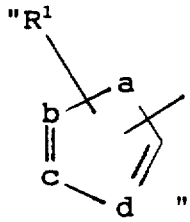     should read    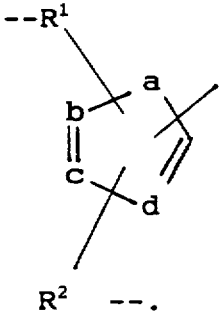

In Column 2, line 32:

"$(CH_2)_mOR7$," should read $--(CH_2)_mOR^7,--$;
"U represents >N- or t,20" should read
--U represents >N- or >N→O;--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

It is certified that error appears in the above-identified patent and that said Letters Patent is hereby corrected as shown below:

IN [57] ABSTRACT

In Column 2,

" 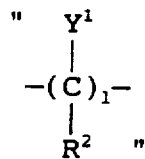    should read    -- 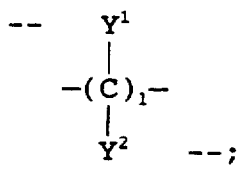 --;

"$Y^1$ and $Y^2$" should read --$Y^1$ and $Y^2$--; and
"3 or" should read --3; or--.

COLUMN 1

Lines 60-67,

"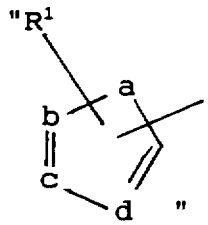    should read    --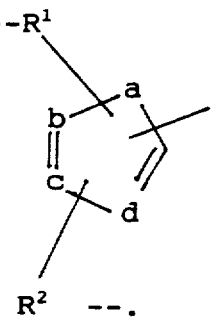--.

UNITED STATES PATENT AND TRADEMARK OFFICE
CERTIFICATE OF CORRECTION

PATENT NO. : 5,053,408

DATED : October 1, 1991

INVENTOR(S) : FUMIO SUZUKI, ET AL.

It is certified that error appears in the above-identified patent and that said Letters Patent is hereby corrected as shown below:

COLUMN 2

Lines 48-53,

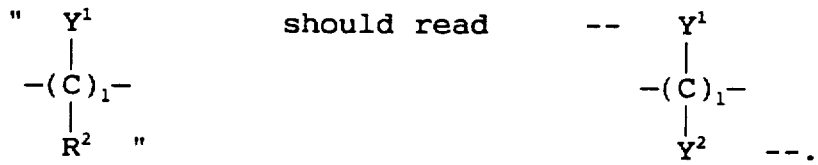

COLUMN 7

Line 25, "us" should read --U--.

COLUMN 13

Line 35, Example 51(45), "$CH_2O$" should read --$CH_3O$--.

COLUMN 26

Line 56, "$cm^{311}$:" should read --$cm^{-1}$--.

COLUMN 27

Line 8, "($DMSO$-$d_6\delta$ ppm)" should read --($DMSO$-$d_6$) $\delta$ (ppm)--.
Line 10, "4.02 4.10(2H," should read --4.02-4.10(2H,--.
Line 32, "4.07" should read --4.07- --.
Line 34, "2.8-4" should read --2.8-4.--.
Line 35, "1" should read --1.--.
Line 39, "yl;" should read --yl)--.
Line 65, "($DMSO$-$d_6\delta$ ppm)" should read --($DMSO$-$d_6$) $\delta$ (ppm)--.

UNITED STATES PATENT AND TRADEMARK OFFICE
CERTIFICATE OF CORRECTION

PATENT NO. : 5,053,408

DATED : October 1, 1991

INVENTOR(S) : FUMIO SUZUKI, ET AL.

It is certified that error appears in the above-identified patent and that said Letters Patent is hereby corrected as shown below:

COLUMN 28

Line 25, "5.45 J=5.2, 2.3 Hz), 5.25-6.10 (1H, m), 5.36(1H, dd," should read --5.45(1H, m), 5.36(1H, dd, J=5.2, 2.3Hz), 5.26-6.10--.

Line 47, "(DMSO-$d_6$$\delta$ ppm): 7.55-8- 15" should read --(DMSO-$d_6$) $\delta$ (ppm): 7.55-8.15--.

Line 49, "2.70 4.25" should read --2.70-4.25--.

COLUMN 29

Line 3, "6" should read --$\delta$--.

Line 16, "m-1" should read --ml--.

Line 54, "6" should read --$\delta$--.

COLUMN 30

Line 27, "85 m)" should read --m)--.

Line 45, "(DMSO-$d_6$$\delta$ ppm)" should read --(DMSO-$d_6$) $\delta$ (ppm)--.

Line 51, "4-Deoxy" should read --5-Deoxy--.

Line 66, "(DMSO-$d_6$$\delta$ ppm)" should read --(DMSO-$d_6$) $\delta$ (ppm)--.

COLUMN 31

Line 38, "(DMSO-$d_6$$\delta$ ppm)" should read --(DMSO-$d_6$) $\delta$ (ppm)--.

Line 66, "6" should read --$\delta$--.

COLUMN 32

Line 23, "4.00 4.09" should read --4.00-4.09--.

Line 40, "8.9" should read --8.97--.

Line 43, "(DMSO-$d_6$$\delta$ ppm)" should read --(DMSO-$d_6$) $\delta$ (ppm)--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

It is certified that error appears in the above-identified patent and that said Letters Patent is hereby corrected as shown below:

COLUMN 33

Line 16, "(DMSO-$d_6\delta$ ppm)" should read --(DMSO-$d_6$) $\delta$ (ppm)--.
   Line 33, "1642" should read --1642,--.

COLUMN 34

Line 8, "(DMSO-$d_6\delta$ ppm)" should read --(DMSO-$d_6$) $\delta$ (ppm)--.
   Line 36, "J=6 8" should read --J=6.8--.
   Line 58, "4" should read --4.--.

COLUMN 35

Line 8, "(KBr)" should read --IR (KBr)--.
   Line 31, "(DMSO-d ) 6 (ppm)" should read
       --(DMSO-$d_6$) $\delta$ (ppm)--.
   Line 50, "(DMSO-$d_6\delta$ ppm)" should read --(DMSO-$d_6$) $\delta$ (ppm)--.

COLUMN 36

Line 3, "(DMSO-$d_6\delta$ ppm)" should read --(DMSO-$d_6$) $\delta$ (ppm)--.
   Line 40, "cm)" should read --$cm^{-1}$)--.
   Line 41, "[DMSO-$d_6\delta$ ppm)" should read --(DMSO-$d_6$) $\delta$ (ppm)--.
   Line 52, "-lyl)" should read -- -1-yl)--.

COLUMN 37

Line 2, "(DMSO-$d_6\delta$ ppm)" should read --(DMSO-$d_6$) $\delta$ (ppm)--.
   Line 28, "(DMSO-$d_6\delta$ ppm)" should read --(DMSO-$d_6$) $\delta$ (ppm)--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

It is certified that error appears in the above-identified patent and that said Letters Patent is hereby corrected as shown below:

COLUMN 38

Line 23, "(DMSO-$d_6$δ ppm)" should read --(DMSO-$d_6$) δ (ppm)--.
Line 49, "(DMSO-$d_6$δ ppm)" should read --(DMSO-$d_6$) δ (ppm)--.

COLUMN 39

Line 7, "(Compound 3)" should read --(Compound 43)--.
Line 35, "cm" should read --$cm^{-1}$:--.
Line 47, "-lyl]-" should read -- -1-yl]- --.

COLUMN 40

Line 39, "46.," should read --46.13 H,--.

COLUMN 41

Line 3, "(DMSO-$d_6$δ ppm)" should read --(DMSO-$d_6$) δ (ppm)--.
Line 33, "lyl" should read --1-yl--.
Line 46, "(DMSO-$d_6$δ ppm)" should read --(DMSO-$d_6$) δ (ppm)--.

COLUMN 42

Line 29, "480 (M-1)" should read --480 ($M^++1$)--.
Line 53, "(CDCl3δ ppm)" should read --($CDCl_3$) δ (ppm)--.

COLUMN 43

Line 30, "(DMSO-d δ ppm)" should read --(DMSO-$d_6$) δ (ppm)--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

It is certified that error appears in the above-identified patent and that said Letters Patent is hereby corrected as shown below:

COLUMN 44

Line 8, "(DMSO-d $\delta$ ppm)" should read --(DMSO-$d_6$) $\delta$ (ppm)--.
Line 51, "(DMSO-d $\delta$ ppm)" should read --(DMSO-$d_6$) $\delta$ (ppm)--.

COLUMN 45

Line 45, "1506" should read --1506, 1277--.
Line 47, "(1H, s)," should read --(1H, m), 4.03-4.10 (2H, m), 3.88-3.99(1H,m), 3.77(6H, s),--.

COLUMN 46

Line 4, "(DMSO-$d_6\delta$ ppm)" should read --(DMSO-$d_6$) $\delta$ (ppm)--.
Line 42, "(DMSO-d $\delta$ ppm)" should read --(DMSO-$d_6$) $\delta$ (ppm)--.
Line 65, "(DMSO-$d_6\delta$ ppm)" should read --(DMSO-$d_6$) $\delta$ (ppm)--.

COLUMN 49

Line 40, "3.1 4.3" should read --3.1-4.3--.
Line 56, "3.99 4.13" should read --3.99-4.13--.

COLUMN 53

Line 24, "1639," should read --1639, 1280--.
Line 27, "5.45(1H," should read --5.45(1H, m), 5.34(1H, m), 3.15-5.20(14H, m)--.

COLUMN 55

Line 8, "($M^++1$) 30 IR (KBr)" should read --($M^++1$) ¶ IR (KBr)--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

It is certified that error appears in the above-identified patent and that said Letters Patent is hereby corrected as shown below:

COLUMN 55

Line 12, "3.0 4.3" should read --3.0-4.3--.
Line 15, "lyl" should read --l-yl--.
Line 45, "(2H-.," should read --(2H,--.

COLUMN 56

Line 40, "e,crc/A/)." should read -- Ⓐ ).--.
Line 42, "e,crc/A/) " should read -- Ⓐ ).--.

COLUMN 57

Line 31, Insert: --IR (KBr) $cm^{-1}$: 1644, 1629, 1480, 1426, 1297, 1276--.
Line 46, "cm" should read --$cm^{-1}$:--.

COLUMN 58

Line 23, "(Compound" should read --(Compound 87)--.
Line 29, "2 hours" should read
-- 2 hours
  Melting point: 152.0-152.5°C.--.

COLUMN 59

Line 52, "m," should read --m),--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

Page 9 of 12

It is certified that error appears in the above-identified patent and that said Letters Patent is hereby corrected as shown below:

COLUMN 60

Line 9, "2 hours" should read
    --            2 hours
      Melting point: 198-200°C.--.
Line 57, "2.8-4 7" should read --2.8-4.7--.

COLUMN 61

Line 12, "82.0°C. MS" should read --82.0°C. ¶ MS--.

COLUMN 62

Line 30, "(solution" should read --(solution Ⓐ').--.
Line 33, "e,crc/A/'" should read -- Ⓐ' --.

COLUMN 65

TABLE 3, "c(3)         "          ONO₂ d(4)       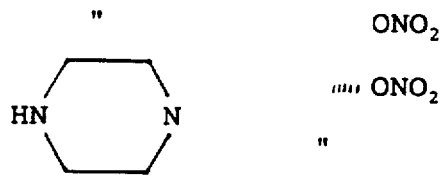     ᴵᴵᴵᴵ ONO₂

"

should read

--c(3)        "                  ≊ ONO₂ d(4)          ᴵᴵᴵᴵ ONO₂

--.

UNITED STATES PATENT AND TRADEMARK OFFICE
CERTIFICATE OF CORRECTION

PATENT NO. : 5,053,408

DATED : October 1, 1991

INVENTOR(S) : FUMIO SUZUKI, ET AL.

It is certified that error appears in the above-identified patent and that said Letters Patent is hereby corrected as shown below:

COLUMN 65

Line 34, "5-methansulfonate" should read --5-methanesulfonate--.

COLUMN 67

Line 33, "6" should read --δ--.

COLUMN 68

Line 62, "nonahydrate" should read --nonanhydrate--.
Line 63, "nonahydrate" should read --nonanhydrate--.

COLUMN 69

Line 65, "(-83.8" should read --(83.8--.

COLUMN 70

Line 54, "indole-3acetic" should read --indole-3-acetic--.

COLUMN 74

Line 1, "drided" should read --dried--.
Line 28, "J=" should read --J=7.0 Hz), 2.40-3.15(8H, m), 1.75(2H, m)--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

It is certified that error appears in the above-identified patent and that said Letters Patent is hereby corrected as shown below:

COLUMN 74

Lines 47-52,

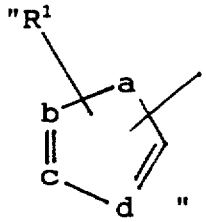   should read   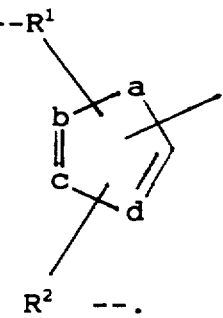

COLUMN 75

Line 30, "or -S-" should read --or -S-;--.

Lines 34-38,

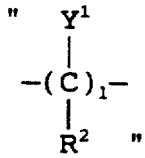   should read   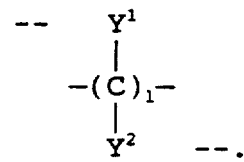

Line 51, "°may" should read --may--.

UNITED STATES PATENT AND TRADEMARK OFFICE
CERTIFICATE OF CORRECTION

PATENT NO. : 5,053,408
DATED : October 1, 1991
INVENTOR(S) : FUMIO SUZUKI, ET AL.

It is certified that error appears in the above-identified patent and that said Letters Patent is hereby corrected as shown below:

COLUMN 76

Line 12, "2nitrate" should read --2-nitrate--.

Line 24, "and X" should read --and X is $-\overset{\overset{O}{\|}}{C}-$.--.
Lines 25-33, structural formula should be deleted.

COLUMN 78

Line 9, "and X" should read --and X is $-\overset{\overset{O}{\|}}{C}-$.--.
Lines 10-18, structural formula should be deleted.

COLUMN 80

Line 21, "claim 1," should read --claim 25,--.

Signed and Sealed this

Twenty-second Day of November, 1994

BRUCE LEHMAN

Commissioner of Patents and Trademarks